US012642797B2

(12) United States Patent
Jia et al.

(10) Patent No.: US 12,642,797 B2
(45) Date of Patent: Jun. 2, 2026

(54) COATED GRANULE, SOLID DISPERSION, AND PREPARATION CONTAINING VORTIOXETINE HYDROBROMIDE FOR ORAL TASTE MASKING

(71) Applicant: Seasons Biotechnology (Taizhou) Co., Ltd., Taizhou (CN)

(72) Inventors: Qiang Jia, Taizhou (CN); Fa Huang, Taizhou (CN); Ru Wang, Taizhou (CN); Jinjin Yang, Taizhou (CN); Youbing Wei, Taizhou (CN); Tianhua Ma, Taizhou (CN); Yunzhong Wang, Taizhou (CN); Yanyun Hu, Taizhou (CN); Changhu Chu, Taizhou (CN)

(73) Assignee: Seasons Biotechnology (Taizhou) Co., Ltd., Zhejiang (CN)

( * ) Notice: Subject to any disclaimer, the term of this patent is extended or adjusted under 35 U.S.C. 154(b) by 804 days.

(21) Appl. No.: 17/617,805

(22) PCT Filed: Sep. 3, 2020

(86) PCT No.: PCT/CN2020/113341
§ 371 (c)(1),
(2) Date: Dec. 9, 2021

(87) PCT Pub. No.: WO2021/043227
PCT Pub. Date: Mar. 11, 2021

(65) Prior Publication Data

US 2022/0249466 A1 Aug. 11, 2022

(30) Foreign Application Priority Data

Sep. 4, 2019 (CN) ........................ 201910571194.3

(51) Int. Cl.

| | |
|---|---|
| ***A61K 31/495*** | (2006.01) |
| ***A61K 9/20*** | (2006.01) |
| ***A61K 47/32*** | (2006.01) |
| ***A61K 47/34*** | (2017.01) |
| ***A61K 47/36*** | (2006.01) |

(52) U.S. Cl.
CPC .............. *A61K 31/495* (2013.01); *A61K 9/20* (2013.01); *A61K 47/32* (2013.01); *A61K 47/34* (2013.01); *A61K 47/36* (2013.01)

(58) Field of Classification Search
None
See application file for complete search history.

(56) References Cited

U.S. PATENT DOCUMENTS

| | | | | |
|---|---|---|---|---|
| 9,562,024 | B2 | 2/2017 | Song et al. | |
| 2004/0241235 | A1 | 12/2004 | Lebon et al. | |
| 2015/0025084 | A1* | 1/2015 | Jeong | A61K 9/70 514/252.16 |
| 2016/0200698 | A1* | 7/2016 | Song | C07D 295/096 544/398 |
| 2016/0214950 | A1 | 7/2016 | Song et al. | |
| 2019/0142753 | A1* | 5/2019 | Sun | A61K 9/5089 424/490 |
| 2020/0147222 | A1 | 5/2020 | Fujisawa et al. | |

FOREIGN PATENT DOCUMENTS

| | | | | |
|---|---|---|---|---|
| CN | 1525852 | A | | 9/2004 |
| CN | 1744881 | A | | 3/2006 |
| CN | 103989650 | A | * | 8/2014 |
| CN | 104586756 | A | | 5/2015 |
| CN | 104736526 | A | | 6/2015 |
| CN | 105030713 | A | | 11/2015 |
| CN | 105111167 | A | | 12/2015 |
| CN | 104736526 | B | | 4/2016 |
| CN | 105534933 | A | | 5/2016 |
| CN | 106491604 | A | | 3/2017 |
| CN | 106580901 | A | | 4/2017 |
| CN | 107412183 | A | | 12/2017 |
| CN | 107638425 | A | | 1/2018 |
| CN | 108069925 | A | | 5/2018 |
| CN | 108498459 | A | | 9/2018 |
| CN | 109589314 | A | | 4/2019 |
| EP | 3184104 | A1 | | 6/2017 |
| WO | 2007144005 | A1 | | 12/2007 |
| WO | 2015035802 | A1 | | 3/2015 |
| WO | 2015044963 | A1 | | 4/2015 |
| WO | 2017159585 | A1 | | 9/2017 |
| WO | 2018042168 | A1 | | 3/2018 |
| WO | 2018065348 | A1 | | 4/2018 |

OTHER PUBLICATIONS

Breslin PA, Beauchamp GK. Suppression of bitterness by sodium: variation among bitter taste stimuli. Chem Senses. Dec. 20, 1995(6):609-23. doi:10.1093/chemse/20.6.609. (Year: 1995).*
Zhang et al. Formulation and Technology Study on the Taste Masking Granules, Advanced Materials Research, vol. 1088, pp. 526-529 2015-02-10, https://doi.org/10.4028/www.scientific.net/AMR.1088.526 (Year: 2015).*
Gokhale et al., "Orally Disintegrating Tablets Novel Controlled Release Formulation for Orally Disintegrating Tablets using Ion Exchange Resins," Drug Development & Delivery, Jun. 1, 2013, vol. 13(5), pp. 40-45, XP055810704.
"Methacrylic Acid—Methyl Methylcrylate Copolymer (1:1)", European Pharmacopoeia, Jan. 2008, 2 pages.
"Methacrylic Acid Copolymer", U.S. Pharmacopeia, downloaded from the internet Nov. 22, 2021, www.pharmacopeia.cn/v29240/usp29nf24s0_m49850.html, 2 pages.
"USP 40-NF 35", downloaded from the internet Nov. 22, 2021, https://www.uspnf.com/official-text/proposal-statuscommentary/usp-40-nf-35, 4 pages.

(Continued)

*Primary Examiner* — Sahana S Kaup
*Assistant Examiner* — Ashlee E Wertz
(74) *Attorney, Agent, or Firm* — Buchanan Ingersoll & Rooney PC

(57) ABSTRACT

A coated granule, a solid dispersion, a composition, and a preparation for oral masking, which improve the taste masking effect of vortioxetine hydrobromide, and improve the patient adherence and compliance.

10 Claims, 13 Drawing Sheets

(56) References Cited

OTHER PUBLICATIONS

Ge et al., (Non Official Translation: Common Flavor Technology), (Non-Official Translation: New Clinical Pharmacology), dated Mar. 31, 2018, 5 pages.
International Search Report and Written Opinion for International Application No. PCT/CN2020/113341, dated Dec. 9, 2020, 10 pages.
"Polyacrylic Resin II", Chinese Parmacopoeia 2020 Edition, 2 pages.
"Polyacrylic Resin IV", Chinese Parmacopoeia 2020 Edition, 1 page.
Vasanthavada, et al., "Development of Solid Dispersion for Poorly Water-Soluble Drugs", Water-Insoluble Drug Formulation, Third Edition, Edited by Ron Liu, Chapter 18, pp. 542-543, 2018.

* cited by examiner

| No. | P/V | Wavelength | Abs. | Description |
|---|---|---|---|---|
| 1 | | 225.4 | 0.5989 | |
| 2 | | 202.2 | 1.3751 | |
| 3 | | 219.0 | 0.5868 | |

| No. | P/V | Wavelength | Abs. | Description |
|---|---|---|---|---|
| 1 | ↑ | 204.6 | 0.0661 | |
| 2 | ↑ | 193.0 | 9.0538 | |
| 3 | ⊗ | 195.4 | 0.0499 | |
| 4 | ⊗ | 192.0 | 9.0476 | |

| No. | P/V | Wavelength | Abs. | Description |
|---|---|---|---|---|
| 1 | ↑ | 225.2 | 0.6657 | |
| 2 | ↑ | 202.2 | 1.4215 | |
| 3 | ⊗ | 219.0 | 0.6541 | |

| No. | P/V | Wavelength | Abs. | Description |
|---|---|---|---|---|
| 1 | (P) | 225.2 | 0.5353 | |
| 2 | (P) | 202.0 | 1.1495 | |
| 3 | (V) | 219.2 | 0.5276 | |

| No. | P/V | Wavelength | Abs. | Description |
|---|---|---|---|---|
| 1 | (P) | 225.4 | 0.6683 | |
| 2 | (P) | 202.2 | 1.4319 | |
| 3 | (V) | 218.8 | 0.6516 | |

| No. | P/V | Wavelength | Abs. | Description |
|---|---|---|---|---|
| 1 | ⊕ | 224.2 | 0.8420 | |
| 2 | ⊕ | 202.2 | 1.7779 | |
| 3 | ⊗ | 219.8 | 0.8376 | |

| No. | P/V | Wavelength | Abs. | Description |
|---|---|---|---|---|
| 1 | ⊕ | 224.0 | 0.8427 | |
| 2 | ⊕ | 202.2 | 1.7807 | |
| 3 | ⊗ | 219.8 | 0.8382 | |

| No. | P/V | Wavelength | Abs. | Description |
|---|---|---|---|---|
| 1 | ⊕ | 203.6 | 0.0710 | |

| No. | P/V | Wavelength | Abs. | Description |
|---|---|---|---|---|
| 1 | ⊕ | 224.6 | 0.6826 | |
| 2 | ⊕ | 202.2 | 1.4383 | |
| 3 | ◆ | 220.0 | 0.6784 | |

| No. | P/V | Wavelength | Abs. | Description |
|-----|-----|-----------|------|-------------|
| 1 | ⬆ | 223.6 | 0.7381 | |
| 2 | ⬆ | 202.4 | 1.5306 | |
| 3 | ⬇ | 220.8 | 0.7372 | |

COATED GRANULE, SOLID DISPERSION, AND PREPARATION CONTAINING VORTIOXETINE HYDROBROMIDE FOR ORAL TASTE MASKING

CROSS-REFERENCE TO RELATED APPLICATION

This application is a U.S. national phase application of International Application No. PCT/CN2020/113341, filed Sep. 3, 2020, which claims the benefit of Chinese Patent Application No. CN 201910571194.3, filed on Sep. 4, 2019, the contents of each of which are incorporated herein in their entireties for all purposes.

FIELD OF THE INVENTION

The present invention relates to technical field of pharmaceutical preparations, in particular to a coated granule, solid dispersion, combination and composition for oral taste masking.

BACKGROUND OF THE INVENTION

Vortioxetine is a multi-target antidepressant with both 5-$HT_3$ receptor antagonism and 5-$HT_{1A}$ receptor agonism, and is used for the treatment of major depressive disorder. At present, vortioxetine hydrobromide is used clinically as its active ingredient, which was jointly developed by Takeda and H. Lundbeck. It was approved by FDA in Sep. 30, 2013 for marketing under the trade name Brintellix. The approved four strengths are 5 mg, 10 mg, 15 mg and 20 mg, and the dosage form is film-coated tablets.

The chemical name of vortioxetine hydrobromide is 1-[2-(2,4-dimethyl-phenylsulfanyl)-phenyl]piperazine hydrobromide. Its English name is vortioxetine hydrobromide with molecular formula $C_{18}H_{22}N_2S{\cdot}HBr$. In addition, U.S. Pat. No. 9,562,024B2 disclosed the compound Vortioxetine hemihydrobromide, that is, every two vortioxetine molecules share one hydrobromic acid molecule, and the molecular formula is $C_{18}H_{22}N_2S{\cdot}\frac{1}{2}HBr$. The structural formulas of $C_{18}H_{22}N_2S{\cdot}HBr$ and $C_{18}H_{22}N_2S{\cdot}\frac{1}{2}HBr$ are as follows:

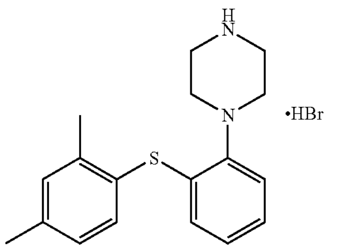

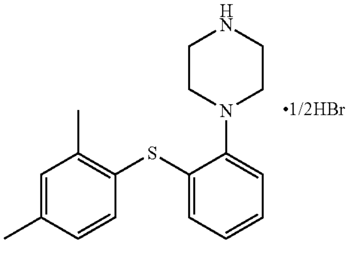

Depressive disorder is a common disease, with strong clinical demand. However, during the onset of depression, patients often refuse or do not cooperate with treatment, and spit out the pills they have taken when medical staff and home nursing staff are not paying attention. Ordinary tablets and capsules are "integral tablets", so mental patients, the elderly, and long-term bedridden patients (the tablets are stuck in the esophagus) are still dangerous to take. Therefore, there is a clinical need for more suitable dosage forms to improve patients' medication adherence or compliance. Orally dispersible drug product enables the drug to exist in the oral cavity in the state of particulate compositions (such as granules, powders, suspensions, dry suspensions) or liquid compositions (such as oral suspensions), or to be able to quickly in the oral cavity change to a particulate state or a liquid state (for example, orally disintegrating tablets, orally dispersible tablets). Orally dispersible dosage form is the most suitable technical means to improve the compliance of patients with depression. Among them, orally disintegrating tablet is the best dosage form because of its convenient use, convenient carrying, convenient transportation and stable quality, such as alprazolam orally disintegrating tablets, olanzapine orally disintegrating tablets and risperidone orally disintegrating tablets and so on.

Due to the physical and chemical properties and clinical compliance of vortioxetine API, very few other dosage forms have been marketed so far.

Both the vortioxetine lactate marketed in Europe and vortioxetine hydrobromide and are very irritating to the oral mucosa, and will cause discomfort to the user when exposed to the mouth, especially to the tongue surface, even after rinsing, this irritation still lasted for half a day or even longer. This will affect drug compliance and limit the application of oral compositions exposed to the oral cavity. Therefore, it is necessary to prepare orally dispersible dosage forms other than film-coated tablets to overcome the problem of mucosal irritation.

Two methods are usually used to overcome the unpleasant taste of drugs. The first method is to reduce the solubility of the drug to reduce the exposure of the drug in the oral cavity. The other method is to change the ability of the drug to interact with taste receptors, affecting the taste-related receptors, which will have potentially unknown side effects. Therefore, the first method is safer for patients. In order to reduce the irritation of the drug in the oral cavity, it is necessary to reduce the exposure of the drug in the oral cavity and reduce the dissolution of the drug. However, while reducing the dissolution of the drug, it will also slow down the absorption of the drug, thereby affecting the absorption and metabolism of the immediate-release dosage form, and affecting the efficacy and safety of the drug. This technical contradiction is also the main technical obstacle for the product to be marketed without oral taste-masking immediate-release dosage form. Especially when the patient's condition improves and he is willing to cooperate with the medication and switch to ordinary immediate-release coated tablets, the two dosage forms have different dissolution and absorption rates of metabolism, leading to potential physiological and pathological problems after the patient's medication switch.

The use of flavoring agents to adjust the taste is also a method to adjust the unfavorable taste such as the bitterness and astringency of the API, but the effect of the flavoring agent on the irritation improvement of vortioxetine is very poor.

The approved oral solution of vortioxetine lactate has not been accepted by the market for many years due to its strong irritation. Therefore, there is an urgent need to develop new taste masking oral exposure-type immediate-release compositions suitable for depressed patients to meet clinical personalized medicine.

SUMMARY OF THE INVENTION

In view of the problems of vortioxetine on the oral mucosa and tongue surface irritation and poor taste, one or more embodiments of the present invention provide taste masking immediate-release dosage compositions of vortioxetine, which can improve patient adherence and compliance by using appropriate excipients and preparation methods.

One or more embodiments of the present invention provide orally dispersible compositions of vortioxetine hemihydrobromide, which comprise vortioxetine hemihydrobromide and pharmaceutically acceptable excipients.

In one or more embodiments of the present invention, the orally dispersible compositions of the present application are tablets, granules, capsules, powders, suspensions, dry suspensions, or solutions.

In one or more embodiments of the present invention, the tablets are orally disintegrating tablets or dispersible tablets.

One or more embodiments of the present invention provide orally dispersible taste masking composition of vortioxetine hemihydrobromide or vortioxetine hydrobromide, which comprises vortioxetine hemihydrobromide or vortioxetine hydrobromide and pharmaceutically acceptable taste masking excipients.

In one or more embodiments of the present invention, and in the orally dispersible taste masking composition of the present invention, wherein vortioxetine hemihydrobromide or vortioxetine hydrobromide is coated with the taste masking excipients to form coated granules.

In one or more embodiments of the present invention, wherein the taste masking excipients in the coated granules are cellulose acetate, ethyl cellulose, hydroxypropyl cellulose, methacrylic acid copolymer, chitosan, copovidone, or polyvinyl alcohol.

In one or more embodiments of the present invention, the taste-masking excipients in the coated granule include alkaline excipients.

In one or more embodiments of the present invention, wherein the coated granules comprise an anticaking agent.

In one or more embodiments of the present invention, vortioxetine hemihydrobromide or vortioxetine hydrobromide in the orally dispersible taste masking composition is dispersed in the taste masking excipient to form a solid dispersion.

In one or more embodiments of the present invention, wherein the taste masking excipients in the solid dispersions are cellulose acetate, ethyl cellulose, hydroxypropyl cellulose, methacrylic acid copolymer, chitosan, copovidone, povidone, poly vinyl alcohol, or polyethylene glycol. In one or more embodiments of the present invention, taste masking excipients in the mentioned solid dispersions include alkaline excipients.

In one or more embodiments of the present invention, wherein vortioxetine hemihydrobromide or vortioxetine hydrobromide in the solid dispersions is mixed with alkaline excipients.

In one or more embodiments of the present invention, wherein vortioxetine hemihydrobromide or vortioxetine hydrobromide in the solid dispersions is mixed with at least one of trisodium phosphate, disodium hydrogen phosphate, dipotassium hydrogen phosphate, potassium carbonate, sodium carbonate, sodium bicarbonate, potassium citrate, sodium acetate, calcium hydroxide, sodium hydroxide, potassium hydroxide, or meglumine to form a composition.

One or more embodiments of the present invention provide taste masking coated granule of vortioxetine hemihydrobromide or vortioxetine hydrobromide, wherein the taste masking coating excipients of the taste masking coated granules are cellulose acetate, ethyl cellulose, hydroxypropyl cellulose, methacrylic acid copolymer, chitosan, copovidone, or polyvinyl alcohol.

In one or more embodiments of the present invention, wherein the taste masking coating excipients comprise alkaline excipients.

In one or more embodiments of the present invention, wherein the taste masking coating excipients comprise anticaking agents.

One or more embodiments of the present invention provide solid dispersion of vortioxetine hemihydrobromide or vortioxetine hydrobromide, wherein the taste masking coating excipients are cellulose acetate, ethyl cellulose, hydroxypropyl cellulose, methacrylic acid copolymer, chitosan, copovidone, povidone, polyvinyl alcohol, or polyethylene glycol.

In one or more embodiments of the present invention, wherein the taste masking excipients comprise alkaline excipients. One or more embodiments of the present invention provide a taste masking composition of vortioxetine hemihydrobromide or vortioxetine hydrobromide, which comprises vortioxetine hemihydrobromide or vortioxetine hydrobromide and alkaline excipients.

In one or more embodiments of the present invention, wherein, the alkaline excipients in the taste masking composition are at least one of trisodium phosphate, disodium hydrogen phosphate, dipotassium hydrogen phosphate, potassium carbonate, sodium carbonate, sodium bicarbonate, potassium citrate, sodium acetate, calcium hydroxide, sodium hydroxide, potassium hydroxide, or meglumine.

In one or more embodiments of the present invention, the methacrylic acid copolymers in the orally dispersible taste masking composition, taste masking coated granule, or taste masking solid dispersion are polyacrylic resins.

In one or more embodiments of the present invention, the polyacrylic resin in the orally dispersible taste masking composition, taste masking coated granule, or taste masking solid dispersion is polyacrylic resin II or polyacrylic resin IV.

In one or more embodiments of the present invention, vortioxetine hemihydrobromide or vortioxetine hydrobromide in the orally dispersible taste masking composition or taste masking coated granule is coated with taste masking excipients to form a coated granule, and wherein the said coated granule is further dispersed in the taste masking excipients to form a solid dispersion; in addition, the formed solid dispersion can be further mixed with alkaline excipients.

In one or more embodiments of the present invention, wherein the said vortioxetine hemihydrobromide or vortioxetine hydrobromide in the orally dispersible taste masking composition or solid dispersion is dispersed in taste masking excipients to form a solid dispersion, wherein the solid dispersion is further coated with taste masking excipients to form a coated granule; in addition, the formed coated granule can be further mixed with alkaline excipients.

In one or more embodiments of the present invention, vortioxetine hemihydrobromide or vortioxetine hydrobromide in the orally dispersible taste masking composition or taste masking coated granule is coated with taste masking excipients to form a coated granule, wherein the coated granule can be further mixed with alkaline excipients.

In one or more embodiments of the present invention, wherein the said vortioxetine hemihydrobromide or vortioxetine hydrobromide in the orally dispersible taste masking composition or solid dispersion is dispersed in taste masking excipients to form a solid dispersion, wherein the solid dispersion is further mixed with alkaline excipients.

In one or more embodiments of the present invention, taste masking coated excipients in the orally dispersible taste masking composition or taste masking coated granule are cellulose acetate, ethyl cellulose, hydroxypropyl cellulose, methacrylic acid copolymer, chitosan, copovidone, or polyvinyl alcohol.

In one or more embodiments of the present invention, taste masking excipients in the orally dispersible taste masking composition or taste masking solid dispersion are cellulose acetate, ethyl cellulose, hydroxypropyl cellulose, methacrylic acid copolymer, chitosan, copovidone, povidone, polyvinyl alcohol, or polyethylene glycols.

In one or more embodiments of the present invention, the alkaline excipients in the orally dispersible taste masking composition or taste masking composition are at least one of trisodium phosphate, disodium hydrogen phosphate, dipotassium hydrogen phosphate, potassium carbonate, sodium carbonate, sodium bicarbonate, potassium citrate, sodium acetate, calcium hydroxide, sodium hydroxide, potassium hydroxide, or meglumine.

In one or more embodiments of the present invention, the weight ratio of vortioxetine hemihydrobromide or vortioxetine hydrobromide in the orally dispersible taste masking composition, taste masking coated granule, taste masking solid dispersion or taste masking composition to pharmaceutically acceptable taste masking excipient used to form coatings or solid dispersions is 1:0.1-1:5. For example, 1:0.3-1:3, 1:0.5-1:1.5, and for example, 1:0.1, 1:0.2, 1:0.3, 1:0.4, 1:0.5, 1:0.6, 1:0.7, 1:0.8, 1:0.9, 1:1, 1:2, 1:3, 1:4 or 1:5.

In one or more embodiments of the present invention, the weight ratio of vortioxetine hemihydrobromide or vortioxetine hydrobromide to pharmaceutically acceptable alkaline excipient is amorphous 1:0.01-1:1.1. For example, 1:0.01-1:1, and for example, 1:0.01, 1:0.02, 1:0.03, 1:0.04, 1:0.05, 1:0.06, 1:0.07, 1:0.08, 1:0.09, 1:0.1, 1:0.5, 1:1, 1:1.1.

In one or more embodiments of the present invention, the orally dispersible taste masking composition, taste masking coated granule, taste masking solid dispersion, or taste masking composition of the present invention is crystalline or amorphous substance.

In one or more embodiments of the present invention, the orally dispersible taste masking composition, taste masking coated granule, taste masking solid dispersion, or taste masking composition of the present invention also comprises a filler, a flavoring agent, a release regulator agent, a plasticizer, an anticaking agent and/or a disintegrate agent.

In one or more embodiments of the present invention, the anticaking agent is talc, which accounts for 5%-25% of the total weight of the taste masking coated granule, for example, 10%-20%, and for example, 10%, 11%, 12%, 13%, 14%, 15%, 16%, 17%, 18%, 19%, or 20%.

In one or more embodiments of the present invention, the flavoring agent is neotame, which accounts for 0.05%-0.5% of the total weight of the orally dispersible taste masking composition, for example, 0.1%, 0.2%, or 0.3%.

In one or more embodiments of the present invention, the release regulator agent is polyethylene glycol or alkaline excipient.

In one or more embodiments of the present invention, the disintegrant agent is sodium starch glycolate, croscarmellose sodium, crospovidone, and combinations thereof, which accounts for 1%-8% of the total weight of the orally dispersible taste masking composition, preferably, 2%-6%.

In one or more embodiments of the present invention, the orally dispersible taste masking composition, taste masking coated granule, taste masking solid dispersion, or taste masking combination is (or is prepared) as tablets, granules, capsules, powders, suspensions, dry suspensions, solutions. In one or more embodiments of the present invention, wherein the tablets are orally disintegrating tablets or dispersible tablets.

In one or more embodiments of the present invention, vortioxetine hemihydrobromide or vortioxetine hydrobromide in the orally dispersible taste masking composition, taste masking coated granule, taste masking solid dispersion, or taste masking combination is amorphous or crystal.

One or more embodiments of the present invention provide the use of vortioxetine hemihydrobromide in the preparation of orally dispersible composition, orally dispersible taste masking composition, taste masking coated granule, taste masking solid dispersion, or taste masking combination. In one or more embodiments of the present invention, wherein the oral dispersions or dispersible taste masking compositions are tablets, granules, capsules, powders, suspensions, dry suspensions, and solutions. In one or more embodiments of the present invention, wherein the tablets are orally disintegrating tablets or dispersible tablets.

One or more embodiments of the present invention provide the use of vortioxetine hydrobromide in the preparation of orally dispersible composition, orally dispersible taste masking composition, taste masking coated granule, taste masking solid dispersion, or taste masking combination. In one or more embodiments of the present invention, wherein the oral dispersions or dispersible taste masking compositions are tablets, granules, capsules, powders, suspensions, dry suspensions, and solutions. In one or more embodiments of the present invention, wherein the tablets are orally disintegrating tablets or dispersible tablets.

One or more embodiments of the present invention provide a method for preparing taste masking coated granules of vortioxetine hemihydrobromide or vortioxetine hydrobromide or their compositions thereof, which comprises:

(1) milling vortioxetine hemihydrobromide or vortioxetine hydrobromide to obtain vortioxetine hydrobromide half salt or one salt powder;

(2a) dispersing the taste masking excipients in a solvent, coating the vortioxetine hemihydrobromide or vortioxetine hydrobromide powder with the taste masking excipients through a fluid bed and removing the solvent to obtain the vortioxetine hemihydrobromide or vortioxetine hydrobromide coated with the taste masking excipients; or (2b) adding the vortioxetine hemihydrobromide or vortioxetine hydrobromide powder and taste masking excipients to a solvent to form a suspension, removing the solvent through a fluid bed, spray drying or evaporation, then the vortioxetine hemihydrobromide or vortioxetine hydrobromide coated with the taste masking excipients is obtained;

(3) optionally, the coated vortioxetine hemihydrobromide or vortioxetine hydrobromide is prepared as a composition.

In one or more embodiments of the present invention, sieve of materials through a 20-300 mesh sieve after milling, for example, 100, 150, or 200 mesh sieve.

In one or more embodiments of the present invention, disperse the taste masking excipient and release regulator agent in solvent. In one or more embodiments of the present invention, wherein the release regulator agent is polyethylene glycol or alkaline excipient. In one or more embodiments of the present invention, wherein the solvent is water, ethanol or dichloromethane.

Preferably, wherein the vortioxetine hemihydrobromide or vortioxetine hydrobromide, taste masking excipient, release regulator agent and plasticizer are added to solvent to form suspension of vortioxetine hemihydrobromide or vortioxetine hydrobromide; more preferably, wherein the plasticizer is polyethylene glycol or triethyl citrate; preferably, wherein the solvent is water, ethanol or dichloromethane.

One or more embodiments of the present invention provide a method for preparing solid dispersion of vortioxetine hemihydrobromide or vortioxetine hydrobromide or their compostions thereof, which comprises:

(1) milling vortioxetine hemihydrobromide or vortioxetine hydrobromide to obtain vortioxetine hydrobromide half salt or one salt powder;

(2a) mixing the vortioxetine hemihydrobromide or vortioxetine hydrobromide powder with taste masking excipients, heating at 50-150° C. to soften or liquefy, cooling to solidify, and crushing to obtain powder; or (2b) dissolving the vortioxetine hemihydrobromide or vortioxetine hydrobromide powder and taste masking excipients in a solvent, and removing the solvent by distillation, fluid bed or spray drying to obtain powder;

(3) optionally, the powder obtained in step (2a) or (2b) is prepared as a composition.

In one or more embodiments of the present invention, sieve of materials through a 20-300 mesh sieve after milling, for example, 100, 150, or 200 mesh sieve.

In one or more embodiments of the present invention, wherein the vortioxetine hemihydrobromide or vortioxetine hydrobromide powder, the taste masking excipient and release regulator agent are mixed.

In one or more embodiments of the present invention, wherein the solvent is water, ethanol or dichloromethane.

In one or more embodiments of the present invention, wherein the taste masking excipients are cellulose acetate, ethyl cellulose, hydroxypropyl cellulose, methacrylic acid copolymer, chitosan, copovidone, povidone, polyvinyl alcohol, or polyethylene glycols.

In one or more embodiments of the present invention, wherein the methacrylic acid copolymer is a polyacrylic resin.

In one or more embodiments of the present invention, the polyacrylic resin is polyacrylic resin II or polyacrylic resin IV.

One or more embodiments of the present invention provide a method for preparing taste masking combination of vortioxetine hemihydrobromide or vortioxetine hydrobromide or their compositions thereof, which comprises:

(1) milling vortioxetine hemihydrobromide or vortioxetine hydrobromide to obtain vortioxetine hydrobromide half salt or one salt powder;

(2) mixing the vortioxetine hemihydrobromide or vortioxetine hydrobromide powder with the alkaline excipients to obtain taste masking combination;

(3) optionally, the taste masking combination is prepared as a composition.

Preferably, sieve of materials through a 50-300 mesh sieve after milling, more preferably, 100-200 mesh sieve.

Preferably, wherein the alkaline excipients are trisodium phosphate, disodium hydrogen phosphate, dipotassium hydrogen phosphate, potassium carbonate, sodium carbonate, sodium bicarbonate, potassium citrate, sodium acetate, calcium hydroxide, sodium hydroxide, potassium hydroxide, or meglumine.

In one or more embodiments of the present invention, wherein the powder can be prepared into a conventional composition using conventional methods in the field.

In one or more embodiments of the present invention, the weight ratio of vortioxetine hemihydrobromide or vortioxetine hydrobromide to pharmaceutically acceptable taste masking excipient is 1:0.1-1:5, for example, 1:0.5-1:1.5, 1:0.3-1:1.5, 1:0.3-1:1.3, and for example, 1:0.1, 1:0.2, 1:0.3, 1:0.4, 1:0.5, 1:0.6, 1:0.7, 1:0.8, 1:0.9, 1:1, 1:2, 1:3, 1:4, or 1:5; the weight ratio of vortioxetine hemihydrobromide or vortioxetine hydrobromide to pharmaceutically acceptable alkaline excipient is 1:0.01-1:1.1, preferably, 1:0.01-1:1. One or more embodiments of the present invention provide a solid dispersion comprising vortioxetine hemihydrobromide and polyacrylic resin IV, wherein the weight ratio of vortioxetine hemihydrobromide to polyacrylic resin IV is 1:0.1-1:5, for example, 1:0.3-1:2, 1:0.5-1:1.5, and for example, 1:0.1, 1:0.2, 1:0.3, 1:0.4, 1:0.5, 1:0.6, 1:0.7, 1:0.8, 1:0.9, 1:1, 1:2, 1:3, 1:4, or 1:5.

One or more embodiments of the present invention provide a solid dispersion comprising vortioxetine hydrobromide and polyacrylic resin IV, wherein the weight ratio of vortioxetine hydrobromide to polyacrylic resin IV is 1:0.1-1:5, for example, 1:0.3-1:2, 1:0.5-1:1.5, and for example, 1:0.1, 1:0.2, 1:0.3, 1:0.4, 1:0.5, 1:0.6, 1:0.7, 1:0.8, 1:0.9, 1:1, 1:2, 1:3, 1:4, or 1:5.

In one or more embodiments of the present invention, the solid dispersion comprising vortioxetine hemihydrobromide and polyacrylic resin IV has characteristic peaks as shown in FIG. 20.

In one or more embodiments of the present invention, the solid dispersion comprising vortioxetine hydrobromide and polyacrylic resin IV has characteristic peaks as shown in FIG. 22.

In one or more embodiments of the present invention, for the solid dispersion comprising vortioxetine hemihydrobromide and polyacrylic resin IV, or the solid dispersion formed by vortioxetine hydrobromide and polyacrylic resin IV, using Cu-Kα radiation, the X-ray powder diffraction pattern expressed at 2θ angles has characteristic peaks at the following positions: 4.2±0.2°, 14.5±0.2°, 17.4±0.2°, 19.2±0.2°, and 22.6±0.2°.

In one or more embodiments of the present invention, for the solid dispersion comprising vortioxetine hemihydrobromide and polyacrylic resin IV, or the solid dispersion formed by vortioxetine hydrobromide and polyacrylic resin IV, using Cu-Kα radiation, the X-ray powder diffraction pattern expressed at 2θ angles has characteristic peaks at the following positions: 4.2±0.2°, 14.5±0.2°, 16.6±0.2°, 17.4±0.2°, 19.2±0.2°, 21.5±0.2°, 22.6±0.2°, 24.4±0.2°, 26.0±0.2°, 28.2±0.2°, and 29.0±0.2°.

In one or more embodiments of the present invention, the solid dispersion comprising vortioxetine hemihydrobromide and polyacrylic resin IV, or the solid dispersion formed by vortioxetine hydrobromide and polyacrylic resin IV, also include at least one of PEG 4000, PEG 6000 and PEG 8000. In one or more embodiments of the present invention, wherein the weight ratio of polyacrylic resin IV to at least one of PEG 4000, PEG 6000, and PEG 8000 is 1:0.05-1:2, for example, 1:0.05, 1:0.1, 1:0.5, 1:1, 1:1.5, or 1:2.

One or more embodiments of the present invention provide the use of vortioxetine hemihydrobromide or vortioxetine hydrobromide orally dispersible taste masking composition, taste masking coated granule, taste masking solid dispersion and taste masking combination in the preparing antidepressant drug.

One or more embodiments of the present invention provide vortioxetine hemihydrobromide or vortioxetine hydrobromide orally dispersible taste masking composition, taste masking coated granule, taste masking solid dispersion and taste masking combination, which are used for the treatment of depression disorder or preparing antidepressant drug.

One or more embodiments of the present invention provide a method for the treatment of depression disorder, the method comprising administering the vortioxetine hemihydrobromide or vortioxetine hydrobromide orally dispersible taste masking composition, taste masking coated granule, taste masking solid dispersion, or taste masking combination to a subject in need.

DETAILED DESCRIPTION OF THE INVENTION

In one or more embodiments of the present invention, orally dispersible compositions enable the drug to exist in the oral cavity in the state of particulate compositions (e.g. granules, powders, suspensions, dry suspensions) or liquid compositions (e.g. oral suspensions), or they can be quickly transformed to the state of particulate or liquid (e.g. orally disintegrating tablets, orally dispersible tablets) in the oral cavity.

In one or more embodiments of the present invention, coat vortioxetine hydrobromide powder with suitable taste masking polymer excipients to obtain coated granules, then prepare orally dispersible compositions according to the known method of oral compositions.

In one or more embodiments of the present invention, the orally dispersible composition of vortioxetine hydrobromide comprises vortioxetine hydrobromide, one of polymer selected from taste masking polymer, chitosan and deacetylated chitosan, and other excipients. The weight ratio is vortioxetine hydrobromide:polymer containing dimethylaminoethyl unit, chitosan, or deacetylated chitosan=1:0.1-1:5, for example: 0.3-1:3.

In one or more embodiments of the present invention, the orally dispersible composition of vortioxetine hydrobromide also comprises anticaking agent to prevent adhesion during the preparation of the taste masking coated granules, and the ratio (accounting for the total weight of the taste masking granules) is 5%-25%. The anticaking agent can be talc.

In one or more embodiments of the present invention, the orally dispersible composition of vortioxetine hydrobromide also comprises a flavoring agent, and the ratio (the ratio of the total weight of the composition) is 0.05%-0.5%. The flavoring agent can be Neotame.

The second solution provided by one or more embodiments of the present invention make vortioxetine hydrobromide and suitable polymer excipients into a crystalline or amorphous solid dispersion, and then prepare orally dispersible compositions according to the known method of oral compositions.

In one or more embodiments of the present invention, the orally dispersible taste masking composition of vortioxetine hydrobromide comprises vortioxetine hydrobromide, one of polymer selected from taste masking polymer, chitosan and deacetylated chitosan, and other excipients. The weight ratio is vortioxetine hydrobromide:polymer containing dimethylaminoethyl unit, chitosan, or deacetylated chitosan=1:0.3-1:5.

In one or more embodiments of the present invention, the orally dispersible taste masking composition of vortioxetine hydrobromide also comprises a flavoring agent, and the ratio (the ratio of the total weight of the composition) is 0.05%-0.5%. The flavoring agent can be Neotame.

The third solution provided by one or more embodiments of the present invention uses weak alkaline excipients to temporarily change the pH environment where the drug is dispersed in the oral cavity, causing the drug dissolution in oral cavity below the stimulation threshold and then return to acidic pH environment in the gastric juice, while solving the problems of oral exposure and dissolution and absorption metabolism in the gastrointestinal tract.

In one or more embodiments of the present invention, the orally dispersible taste masking composition of vortioxetine hydrobromide comprises vortioxetine hydrobromide, alkaline or weak alkaline taste masking agent and flavoring agent. The weight ratio is vortioxetine hydrobromide ($C_{18}H_{22}N_2S{\cdot}\frac{1}{2}HBr$ or $C_{18}H_{22}N_2S{\cdot}HBr$):alkaline or weak alkaline taste masking agent and flavoring agent=1:(0.0001-0.01), for example, 1:(0.0009-0.009).

In one or more embodiments of the present invention, the taste masking excipients in the orally dispersible taste masking composition of vortioxetine hydrobromide are pharmaceutically alkaline excipients, including but not limited to trisodium phosphate, disodium hydrogen phosphate, dipotassium hydrogen phosphate, potassium carbonate, sodium carbonate, sodium bicarbonate, potassium citrate, sodium acetate, calcium hydroxide, sodium hydroxide, potassium hydroxide, or meglumine.

In one or more embodiments of the present invention, the flavoring agent in orally dispersible taste masking composition of vortioxetine hydrobromide is pharmaceutically acceptable flavoring agent, including but not limited to Neotame.

In one or more embodiments of the present invention, the taste masking coated particles or taste masking solid dispersion of vortioxetine hydrobromide can be prepared as an oral composition of vortioxetine hydrobromide for oral dispersion.

In one or more embodiments of the present invention, the oral exposure or dispersion compositions of taste masking coated granules or taste masking solid dispersions of vortioxetine hydrobromide include, but are not limited to, compositions that can be exist in particulate compositions (e.g. granules, powders, suspensions, dry suspensions) or solution compositions (e.g. oral solutions) in the oral cavity, or can quickly transform into a particulate or solution state in the oral cavity (e.g. orally disintegrating tablets, orally dispersible tablets).

One or more embodiments of the present invention provide methods for preparing taste masking compositions of vortioxetine hydrobromide, which include at least three preparation methods.

Preparation Method 1:

(1) milling vortioxetine hydrobromide to obtain vortioxetine hydrobromide powder; preferably, sieving of material through a 20-300 mesh sieve after milling, more preferably, 100-200 mesh sieve;

(2a) dispersing the taste masking excipients in a solvent, coat the vortioxetine hydrobromide powder with the taste masking excipients through a fluid bed and removing the solvent to obtain the vortioxetine hydrobromide coated with the taste masking excipients;

preferably, dispersing the taste masking excipients and release regulator agent in a solvent; more preferably, wherein the release regulator agent is polyethylene glycol or alkaline excipients; preferably, wherein the solvent is water, ethanol or dichloromethane; or (2b) adding the vortioxetine hydrobromide powder and taste masking excipients to a solvent to form a suspension, removing the solvent through a fluid bed, spray drying or evaporation, then obtaining the vortioxetine hydrobromide coated with the taste masking excipients; preferably, wherein the vortioxetine hydrobromide, taste masking excipient, release regulator agent and plasticizer are added to the solvent to form suspension of vortioxetine hydrobromide; preferably, wherein the plasticizer is polyethylene glycol or triethyl citrate; preferably, wherein the solvent is water, ethanol or dichloromethane;

(3) optionally, the coated vortioxetine hydrobromide is prepared as a composition.

Preparation Method 2:

(1) milling vortioxetine hydrobromide to obtain vortioxetine hydrobromide powder; preferably, sieving of material through a 20-300 mesh sieve after milling, more preferably, 100-200 mesh sieve;

(2a) mixing the vortioxetine hydrobromide powder with the taste masking excipients, heating at 50-150° C. to soften or liquefy, cooling to solidify, and milling to obtain powder; preferably, wherein the vortioxetine hydrobromide powder, the taste masking excipient and release regulator agent are mixed; or (2b) dissolving the vortioxetine hydrobromide powder and taste masking excipients in a solvent, and removing the solvent by distillation, fluid bed or spray drying to obtain powder; preferably, wherein the solvent is water, ethanol or dichloromethane;

(3) optionally, the powder obtained in step (2a) or (2b) is prepared as a composition.

Preparation Method 3:

(1) milling vortioxetine hemihydrobromide or vortioxetine hydrobromide to obtain powder; preferably, sieving of material through a 50-300 mesh sieve after milling, more preferably, 100-200 mesh sieve;

(2) mixing the vortioxetine hemihydrobromide or vortioxetine hydrobromide powder with alkaline excipients to obtain taste masking composition; preferably, wherein the alkaline excipients are trisodium phosphate, disodium hydrogen phosphate, dipotassium hydrogen phosphate, potassium carbonate, sodium carbonate, sodium bicarbonate, potassium citrate, sodium acetate, calcium hydroxide, sodium hydroxide, potassium hydroxide, or meglumine;

(3) optionally, the taste masking combination is prepared as a composition.

In one or more embodiments of the present invention, in the above-mentioned methods, vortioxetine hemihydrobromide or vortioxetine hydrobromide can be used, and an amorphous or crystalline vortioxetine hemihydrobromide or vortioxetine hydrobromide can be used.

In one or more embodiments of the present invention, the three preparation methods mentioned above can be implemented independently or in combination with each other, or implemented in combination according to known preparation process.

In one or more embodiments of the present invention, the release regulator agent in the above preparation methods include, but are not limited to, mannitol, sorbitol, xylitol, polyethylene glycol, hydroxypropyl cellulose, and/or hydroxypropyl methyl cellulose.

In one or more embodiments of the present invention, the plasticize in the above preparation methods include, but are not limited to polyethylene glycol and/or triethyl citrate.

In one or more embodiments of the present invention, the preparation methods orally dispersible taste masking composition of vortioxetine hydrobromide adopt one or more pharmaceutically acceptable resins and vortioxetine hydrobromide to co-dissolve in one or more pharmaceutically acceptable solvents to obtain a true solution; after the solvent is removed by rotary evaporation, spray drying or fluid bed granulation, the microcrystalline vortioxetine hydrobromide solid dispersion is obtained in the confined space of the polymer; according to the conventional preparation process, add other known excipients in the prescribed amount, and then using the small molecule alkaline material to mask the taste, the oral exposure type vortioxetine hydrobromide oral dispersion and taste masking composition can also be prepared.

In one or more embodiments of the present invention, polyacrylic resin IV and vortioxetine hemihydrobromide or vortioxetine hydrobromide are dissolved in solvent, and the weight ratio of vortioxetine hemihydrobromide or vortioxetine hydrobromide to polyacrylic resin IV is 1:0.1-1:5, preferably, 1:0.3-1:2, more preferably, 1:0.5-1:1.5. Then remove the solvent to obtain solid dispersion, and the characteristic peaks of X-ray powder diffraction pattern: 4.2±0.2°, 14.5±0.2°, 17.4±0.2°, 19.2±0.2°, and 22.6±0.2°; furthermore, the characteristic peaks of X-ray powder diffraction pattern: 4.2±0.2°, 14.5±0.2°, 16.6±0.2°, 17.4±0.2°, 19.2±0.2°, 21.5±0.2°, 22.6±0.2°, 24.4±0.2°, 26.0±0.2°, 28.2±0.2°, and 29.0±0.2°. The solid dispersion has been proved to be stable in dissolution, stable on impurities and stable in crystalline state through stability studies.

In one or more embodiments of the present invention, the preparation methods orally dispersible taste masking composition of vortioxetine hydrobromide adopt one or more pharmaceutically acceptable resins and vortioxetine hydrobromide to co-dissolve in one or more pharmaceutically acceptable solvents, and then reduce the solubility of the solution or remove the solvent, the vortioxetine and resin form a solid dispersion and its granule; according to the conventional preparation process, add other known excipients in the prescribed amount can prepare orally dispersible taste masking composition of vortioxetine hydrobromide; wherein vortioxetine exists in the resin in the state of ions or molecules, and interacts with the functional groups in the resin, so that the dissociation slows down in the oral environment, and after passing through the gastric juice environment, it can quickly dissociate into vortioxetine in gastrointestinal tract.

In one or more embodiments of the present invention, the preparation methods orally dispersible taste masking composition of vortioxetine hydrobromide adopt one or more pharmaceutically acceptable resins and vortioxetine hydrobromide to co-dissolve in one or more pharmaceutically acceptable solvents, and then reduce the solubility (e.g. add poor solvents, or lower the temperature) of the solution or remove the solvent, obtain an amorphous solid dispersion of vortioxetine hydrobromide; according to the conventional preparation process, add other known excipients in the prescribed amount, selectively, add alkaline excipients to the external excipients. The alkaline excipients can change the microenvironment of the receptors on the mucosa and taste buds and reduce the irritation; wherein, vortioxetine hydrobromide exists in an amorphous aggregate state.

In one or more embodiments of the present invention, resins include but are not limited to these linear polymer materials:polyacrylic resins (type L, S or type II, III, IV), methacrylic acid containing functional groups —$NH_2$, $NR_2$, —COOH, —COO—, —$SO_3H$, or —$SO_3$—, divinylbenzene resins and polystyrene resins.

In one or more embodiments of the present invention, the preparation methods of vortioxetine hydrobromide orally dispersible taste masking compositions, mix one or more pharmaceutically acceptable taste masking excipients, one or more pharmaceutically acceptable release regulator agent with vortioxetine hydrobromide, after preparing the solid dispersion by hot-melt granulation and hot-melt extrusion processes, according to the conventional preparation process, add other known excipients in the prescribed amount, then the solid dispersion can be mixed with alkaline taste masking excipients or further coated with taste masking excipients. The vortioxetine hydrobromide orally dispersible taste masking composition release slowly or do not release in the oral environment, and can be rapidly dissociated into vortioxetine hydrobromide in the gastrointestinal tract after passing through the environment of gastric juice, which is absorbed by the gastrointestinal tract.

In one or more embodiments of the present invention, alkaline linear polymer materials include, but are not limited to, polyacrylic resins (e.g. type II or IV), chitosan, or amino sugar polymers.

In one or more embodiments of the present invention, wherein the release regulator agent includes, but is not limited to, mannitol, sorbitol, xylitol, polyethylene glycol, hydroxypropyl cellulose, or hydroxypropyl methylcellulose.

The inventor unexpectedly discovered that Vortioxetine hemihydrobromide ($C_{18}H_{22}N_2S \cdot \frac{1}{2}HBr$) is significantly less irritating than vortioxetine hydrobromide ($C_{18}H_{22}N_2S \cdot HBr$), even if converted to the same amount of $C_{18}H_{22}N_2S$. There is little difference in solubility between the two salts in sodium acetate medium that simulates the oral environment pH 6.8 (using the USP method, the solubility of vortioxetine hydrobromide is 0.15 mg/ml and the solubility of Vortioxetine hemihydrobromide is 0.14 mg/ml), but the irritation of Vortioxetine hemihydrobromide is significantly reduced.

Because Vortioxetine hemihydrobromide has lower oral and tongue irritation, it can be prepared into a solid dosage form with polymer excipients, which greatly improves the dissolution rate and total dissolution rate of vortioxetine in the gastrointestinal tract, while maintaining none oral irritation.

Disintegration speed is an important clinical indicator of orally disintegrating tablets, which is recommended by pharmacopoeias in various countries to be less than 1 minute. In clinical practice, the faster the better, especially for drugs with patient compliance problems. Freeze-dried orally disintegrating tablets can adopt freeze-drying technology, in which the drug active ingredients are evenly dispersed into the skeleton material solution in the state of micro powder or solution, and the dispersed mixture are quantitative packed for each dose, and after freeze-drying, the finished formulation can disintegrate within 5 seconds; but the process is complex and difficult to be industrialized. The compressed orally disintegrating tablet are prepared using a general tablet preparation technology and can also achieve a disintegration time of 1 minute by using a highly efficient disintegrating agent and reducing the tablet pressure. However, reducing pressure of pressing tablet will greatly affect the strength of the tablets, and there will be a lot of inconveniences due to wear and tear during production, transportation and use. Researchers use a variety of disintegrants to obtain a composite disintegrant. It has been able to ensure that the finished product is within the normal strength range of the tablet, and the disintegration is controlled within 10 seconds.

In one or more embodiments of the present invention, the composite disintegrants include but are not limited to carboxymethyl starch sodium, croscarmellose sodium and crospovidone.

In one or more embodiments of the present invention, the weight ratio of carboxymethyl starch sodium, croscarmellose sodium and crospovidone is 1:1:1, and the weight ratio in the composition is 1%-8% respectively, for example, 2%-6%.

In one or more embodiments of the present invention, this invention uses polymers recognized as safe. The currently known molded products of this type of polymer mainly include polyacrylic resin type II and polyacrylic resin type IV (Eudragit E), among which Eudragit E is the English trade name, and the general name is Amino Methacrylate Copolymer. It is included in the USP40-NF35 edition of the United States Pharmacopoeia. The FDA has specified that the maximum daily dosage of the polymer is 214.28 mg when used in orally disintegrating tablets for taste masking, which can meet the needs of vortioxetine hydrobromide for taste masking. Its analogs E100 has the same chemical structure, physical and chemical properties and quality standards, and can also meet the needs of preparation.

In one or more embodiments of the present invention, taste is further improved through the selective addition of flavoring agent, while providing a variety of taste portions. One of the flavoring agents used in this technology is Neotame, which has been included in the USP40-NF35 edition of the United States Pharmacopoeia. Neotame has been widely used as a food additive.

In one or more embodiments of the present invention, the use of alkaline excipients as a taste masking agent can significantly reduce the irritation to the tongue, and the irritation can be reduced to a level acceptable for clinical medication.

In one or more embodiments of the present invention, the taste masking agent used is a pharmaceutically acceptable excipient.

The composition provided by one or more embodiments of the present invention can improve patient adherence and compliance, improve the dissolution of vortioxetine hydrobromide, potentially improve the bioavailability of the drug, and it solves the shortcomings of vortioxetine oral composition in the prior art that the dosage form is single and does not meet the needs of clinical differentiation and individualized administration.

The inventor of the present invention has conducted research on commercially available vortioxetine hydrobromide film-coated tablets: after a single dose of 20 mg, 10 mg and 5 mg strengths, there was obvious bitterness and long-term strong delayed irritation after oral dispersion. Oral irritation limits the development and clinical application of oral compositions other than film-coated tablets.

EXAMPLES

Figure 1:
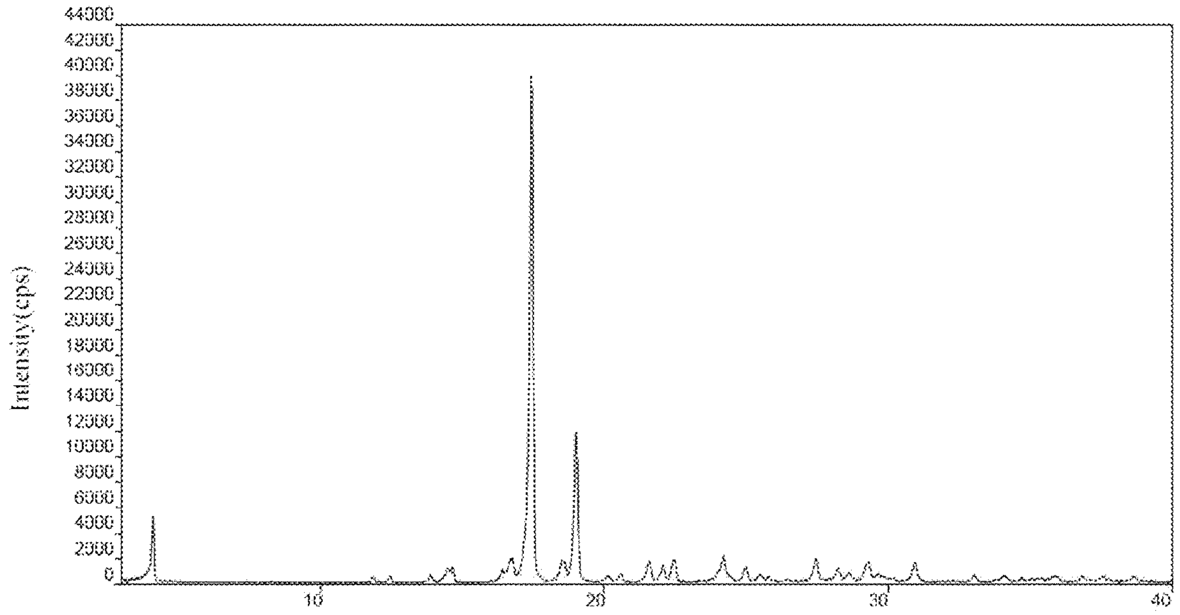
FIG. 1: X-ray powder diffraction pattern of vortioxetine hemihydrobromide.
Figure 2:
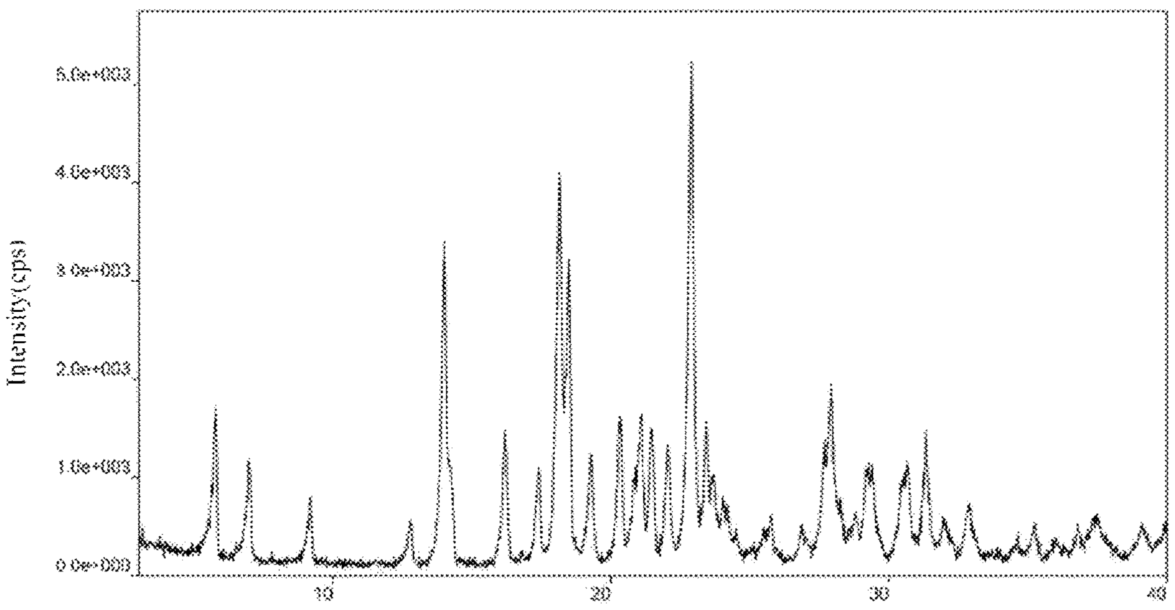
FIG. 2: X-ray powder diffraction pattern of vortioxetine hydrobromide form α.
Figure 3:
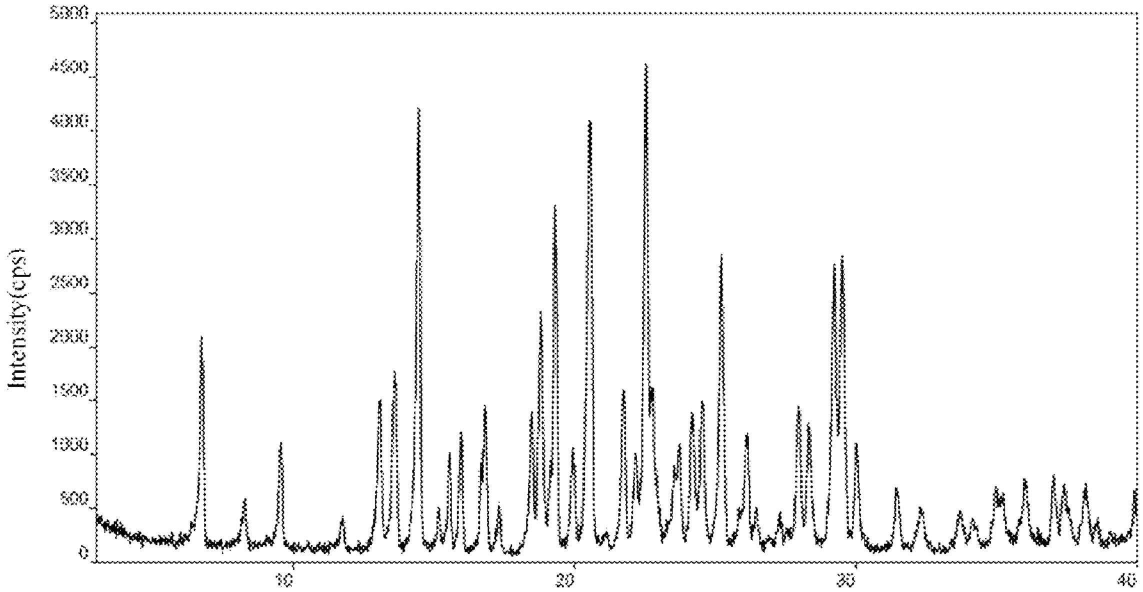
FIG. 3: X-ray powder diffraction pattern of vortioxetine hydrobromide form β.

The following describes the embodiments of the invention in detail with reference to specific examples, but those skilled in the art should understand that the examples are only used to illustrate the invention, and should not be regarded as limiting the scope of the invention.

If specific conditions are not indicated in the examples, it shall be carried out in accordance with the conventional conditions and the conditions recommended by the manufacturer or supplier. Those reagents or instruments that do not indicate the manufacturer and specific model are all conventional products that can be purchased commercially.

For the polyacrylic resin II in this invention, it is named Methyl methacrylate-methacrylic acid copolymer (1:1) in the European Pharmacopoeia and Methacrylic Acid Copolymer Type A in the U.S. Pharmacopoeia, and named polyacrylic resin II in the Chinese Pharmacopoeia. For example, it can be purchased from the supplier Evonik Rohm GmbH Company (for example, the trade name is Eudragit L, Eudragit L100, and Eudmgit L PO) or Anhui Shanhe Pharmaceutical Excipients Co., Ltd. (for example, the product name is polyacrylic resin II).

For the polyacrylic resin IV in this invention, it is named Amino Methacrylate Copolymer in the U.S. Pharmacopoeia, and named polyacrylic resin IV in the Chinese Pharmacopoeia. For example, it can be purchased from the supplier Evonik Röhm GmbH Company (for example, the trade name is Eudragit E100, Eudragit E PO), Guangzhou Maofeng Pharmaceutical Excipients Co., Ltd. (for example, the product name is Urelease E, Urelease E100), or Anhui Shanhe Pharmaceutical Excipients Co., Ltd. (for example, the product name is polyacrylic resin IV).

For other polyacrylic resins, they can be purchased from, for example, Evonik Rohm GmbH Corporation, for example, under the trade names Eudragit RL100, Eudragit L100, Eudragit RS PO, and Eudragit 5100. The excipients used in the examples are not associated with this invention, while when preparing compositions using this invention, other known common and functional pharmaceutical excipients can be used according to the dosage form, stability of the composition and the needs of clinical use. In the examples, vortioxetine hydrobromide does not indicate the specific crystal form used, which means that the crystal form α, β or γ is acceptable.

Instruments Used in the Experiment:

X-ray powder diffraction (XPRD): The instrument is D/max-2200/pc equipped with θ-2θ goniometer RINT2000 Vertical goniometer, MO monochromator and Scintillation counter detector. The acquisition software is XG operation. The instrument is calibrated with the single crystal silicon standard that comes with the instrument. The detection conditions: 2θ angle scan range: 3-40° or 3-50°, step size: 0.02°, speed: 6°/min. Detection process: Using Cu target with a wavelength of 1.54 nm Kα X-rays, K (α1) energy of 40 kV, current intensity of 20 Ma. Samples are tested at room temperature, and the required samples are placed on the Si P non-reflective plate. Samples are sieved before testing.

Ultraviolet visible spectrophotometer: UV-2600, Shimadzu, Japan.

Analytical balance: AUW120D, SHIMADZU.

Rotary evaporator: R205, Taizhou Xinli Electronic Equipment Co., Ltd.

Hot air circulation oven: DHG-9070A, Shanghai Yiheng Scientific Instrument Co., Ltd.

Vortex mixer: Vortex-2, Shanghai Huxi Industrial Co., Ltd.

Multifunctional fluid bed: BWF-1G, Chongqing Enger Granulation Coating Technology Co., Ltd.

Vacuum freeze dryer: FD-2D, Beijing Boyikang Experimental Instrument Co., Ltd.

Rotary tablet press: ZP8, Shanghai Xinyuan Pharmaceutical Machinery Co., Ltd.

High-efficiency coating machine: Labcoating IV, Shenzhen Xinyite Technology Co., Ltd.

Dry granulator: GL-5B, Zhejiang Future Machinery Co., Ltd.

Granulator: P100, Shenzhen Xinyite Technology Co., Ltd.

Portable pH meter: STARTER 300.

Freeze dryer: SCIENT2-30F, Ningbo Scientz Biotechnology Co., Ltd.

Flat blister packaging machine: Zhejiang Future Machinery Co., Ltd.

Related Data Collection Methods:

Test method for pH and exposure (calculated as vortioxetine): Take a tablet of this product (or powder equivalent to 20 mg of vortioxetine), add 5.0 g of purified water, incubate for 5 minutes at 36±2° C. with airtight shaking and disperse, then cool to room temperature, and check the pH of the suspension. Filter through a 0.22 um microporous membrane, take 2.0 ml of the filtrate and dilute to 10 ml with purified water as the test solution, and take the solution quantitatively diluted with purified water to 10 ug/ml (based on vortioxetine) as the reference solution, UV method detects the absorption value at 226 nm wavelength respectively, and calculates the concentration and relative dissolution of vortioxetine.

$$\text{Relative dissolution} = \frac{\begin{array}{c}UV \text{ absorbance of sample} \times \\ \text{Concentration of reference solution} \times 1000 \times 25\end{array}}{UV \text{ aborbance of } \textit{refenence} \text{ solution} \times 20} \times 100\%.$$

Titration Test Method to Determine the Assay of Bromine in Vortioxetine Hydrobromide:

Prepare 0.1 mol/L silver nitrate titrant first, and then prepare 5 mg/ml Eosin Y test solution. Dissolve 0.3 g of sample in 60 mL of methanol. Add 20 mL of water, 20 mL of glacial acetic acid, and 8 drops of eosin Y TS. Titrate with 0.1 N silver nitrate VS to a pink endpoint. Carry out a blank titration.

Calculation Formula:

$$Br\% = \frac{(Vs - Vb) \times N \times 7.990}{0.1 \times W \times (1 - \text{water }\%)} \times 100\%$$

Where, $V_s$=Volume of 0.1 mol/mL silver nitrate consumed for sample, mL $V_b$=Volume of 0.1N silver nitrate consumed for blank, mL N=Normality of silver nitrate volumetric solution W=Weight of the sample, mg Water %=Water of sample 7.990=Each 7.990 mg of Br is equivalent to 1 mL of 0.1 mol/mL silver nitrate.

In the examples, the taste masking effects of test samples were evaluated by the subject's perception of the bitterness and irritation of the oral cavity and tongue.

The Taste and Irritation Classification Tested by the Subjects:

| 0-1 minute instantaneous irritation | Delayed irritation | Bitterness |
|---|---|---|
| + + + Strong irritation, intolerable | Delayed 1-15minutes | Acceptable |
| + + Irritating, tolerable | Delayed 15-30minutes | |
| +Almost no irritation | Delayed more than 30 minutes | Unacceptable |
| Tried by 5-10 subjects and take the average value | | |

Preparation Example 1: Preparation of Vortioxetine Free Base

Vortioxetine was synthesized with reference to the preparation method of Example 24 in Patent Document WO2007/144005A1. The detail process: 40.76 g of $NaOBu^t$, 0.33 g of $Pddba_2$ and 0.68 g of rac-BINAP were stirred with 200 ml of toluene. 42 g of 2-bromo-iodobenzene and 19.54 g of 2,4-dimehtylthiophenol were added with 50 ml toluene. The suspension was heated to reflux and reflux continued for 5 hours. The reaction mixture was cooled to room temperature and filtered through filter aid. The filtrate was added to a mixture of 40.76 g of $NaOBu^t$, 42.2 g of piperazine, 0.33 g of $Pddba_2$ and 0.68 g of rac-BINAP and heated to reflux for 2 hours.

The reaction mixture was cooled down to room temperature. 100 ml of water was added and the water phase was separated off. The organic phase was filtered through filter aid and the filtrate was then washed with 3×80 ml of brine. The organic phase was heated to 70° C. and followed by addition of 16.50 ml of 48%-wt % HBr (145.9 mmol) and 8.3 ml of water. The mixture was stirred for about 30 minutes, then cooled to room temperature, and kept at room temperature for 2 hours. The final product (1-[2-(2,4-Dimethyl-phenylsulfanyl)-phenyl]-piperazine hydrobromide) was collected by filtration and was washed with toluene, dried at 50° C. for 10 hours, producing 40.18 g of off-white powder with molar yield 75%.

The 40.18 g of vortioxetine hydrobromide (obtained in the previous step) was dissolved in 200 mL of water. 200 mL of dichloromethane was added, the pH was adjusted to 9-10 with 15% sodium hydroxide aqueous solution, then the solution was kept for 30 minutes. The solution was stood still and separated off water phase. The water phase was extracted once with 100 mL of dichloromethane. The combined organic phase was washed with 100 mL of water, and the separated organic phases, was added 5 g of anhydrous sodium sulfate to thy. The organic phase was filtered, and then was concentrated to obtain 29.7 g of off-white crystals 1-[2-(2,4-Dimethyl-phenylsulfanyl)-phenyl]-piperazine hydrobromide, which was vortioxetine free base, with molar yield of 94.0%.

Preparation Example 2: Preparation of Vortioxetine Hemihydrobromide

Vortioxetine hemihydrobromide was synthesized with reference to the preparation method of Example 1 in Patent Document U.S. Pat. No. 9,562,024B2. The detail process: 8.00 g (26.8 mmol) vortioxetine was dissolved in 122 ml of ethanol by sonication in a 250 ml of round-bottom flask; 2.70 g of hydrobromic acid (40% w/w, 13.3 mmol) was dissolved in 16 ml of ethanol by sonication; with stirring, the hydrobromic acid solution was slowly added dropwise to the vortioxetine solution; solids precipitated out during the dropwise-addition process; the solvent was removed by rotary evaporation at 40° C.; after drying under vacuum at 40° C. for 24 h, 8.91 g (13.1 mmol) of white solids of the vortioxetine hemihydrobromide were obtained. The percent yield was 98.5%. The bromine assay measured by the titration method was 11.60%.

Preparation Example 3: Preparation of Vortioxetine Hydrobromide Form α

Vortioxetine hydrobromide form α was synthesized with reference to the preparation method of Example 4a in Patent Document WO2007/144005A1. The detail process: 2.0 g of 1-[2-(2,4-Dimethyl-phenylsulfanyl)-phenyl]-piperazine was dissolved in hot 30 ml of ethyl acetate and added 0.73 ml of 48%-wt HBr (aq). This addition caused formation of a thick slurry and addition 10 ml of ethyl acetate was added in order to have proper stirring. The slurry was stirred at room temperature for one hour. Filtration and drying in vacuum (20° C.) overnight produced 2.0 g of the product as a white solid (yield 80%). The product was the α crystal form of vortioxetine hydrobromide. The bromine assay measured by the titration method was 20.76%.

Preparation Example 4: Preparation of Vortioxetine Hydrobromide Form β

Vortioxetine hydrobromide form β was synthesized with reference to the preparation method of Example 4c in Patent Document WO2007/144005A1. The detail process: 49.5 g of 1-[2-(2,4-Dimethyl-phenylsulfanyl)-phenyl]-piperazine was dissolved in 500 ml of ethyl acetate and added 18.5 ml of 48%-wt HBr (aq). This addition caused formation of a thick slurry which was stirred over night at room temperature. Filtration and drying in vacuum (50° C.) overnight produced the product in 29.6 g as white solid (yield 47%). The bromine assay measured by the titration method was 20.69%.

Preparation Example 5: Preparation of Vortioxetine Hydrobromide Form γ

Vortioxetine hydrobromide form γ was synthesized with reference to the preparation method of Example 4e in Patent Document WO2007/144005A1. The detail process: 1 g of 1-[2-(2,4-dimethyl-phenylsulfanyl)-phenyl]-piperazine hydrobromide was dissolved in 20 ml of water and heated to 85° C. The solution was almost clear. Addition of 1 drop of HBr made it clear. HBr was added until cloud point was observed. The solution was cooled to room temperature and dried. The product was the γ crystal form of vortioxetine hydrobromide. The bromine assay measured by the titration method was 20.73%.

Example 1: Vortioxetine Hydrobromide+Coating Material Taste Masking Powder Preparation 1a) Vortioxetine Hemihydrobromide:UreleaseE100: PEG6000=1:0.3:0.07 Taste Masking Powder Preparation 30.00 g of UreleaseE100 and 7.00 g of PEG6000 were added to 470.02 g of medicinal ethanol, stirred to dissolve, set aside.

100.00 g of 100-200 mesh vortioxetine hemihydrobromide and 10.00 g of talc with particle size less than 325 mesh were added to the BWF-1G multifunctional fluid bed installed in the bottom spray coating mode. The air inlet volume and the height of the guide tube were adjusted to make the materials in a fluidized state, and the air inlet temperature was set 50-55° C., peristaltic pump speed was 5 rpm and atomization pressure was 1.0-1.5 atm. The prepared special coating liquid was sprayed into the fluid bed. After spraying, the materials were continued to fluidize for 30 minutes, then stopped heating, and waited until the temperature of the materials was cooled to room temperature. The materials were collected, and the powder with particle size 60-150 mesh was collected by sieving. 125.79 g of taste masking powder with yield 85.57% was obtained. The assay (calculated as vortioxetine) of powder was 60.14%.

If the materials were bonded during the preparation process, an appropriate amount of talcum powder could be added after the machine was stopped to ensure that the materials were in a fluidized state.

The taste masking powder equivalent to 20 mg of vortioxetine and the 100-mesh powder of vortioxetine hemihydrobromide equivalent to 20 mg vortioxetine were tasted and compared by 5 subjects. The irritation of taste masking powder was ameliorated.

Self-made sample: Instantaneous irritation ++, disappeared within 1-15 minutes after delayed irritation, and the bitterness was acceptable.

Reference sample: Instantaneous irritation +++, disappear after more than 30 minutes after delayed irritation, and the bitterness was unacceptable.

Detailed Information is Listed in Table 1:

TABLE 1

Comparison test of taste of vortioxetine hemihydrobromide taste masking powder

| | Instantaneous irritation | | Delayed irritation (min) | | Bitterness | | Grittiness | |
|---|---|---|---|---|---|---|---|---|
| Subject | Self-made sample | Reference sample | Self-made sample | Reference sample | Self-made sample | Reference sample | Self-made sample | Reference sample |
| Subject 1 | + | ++ | 1-15 | >30 | acceptable | unacceptable | N/A | N/A |
| Subject 2 | ++ | +++ | 1-15 | >30 | acceptable | unacceptable | N/A | N/A |
| Subject 3 | ++ | +++ | 1-15 | >30 | acceptable | unacceptable | N/A | N/A |
| Subject 4 | + | ++ | 1-15 | 15-30 | acceptable | acceptable | N/A | N/A |
| Subject 5 | ++ | +++ | 1-15 | >30 | acceptable | unacceptable | N/A | N/A |

Figure 5:
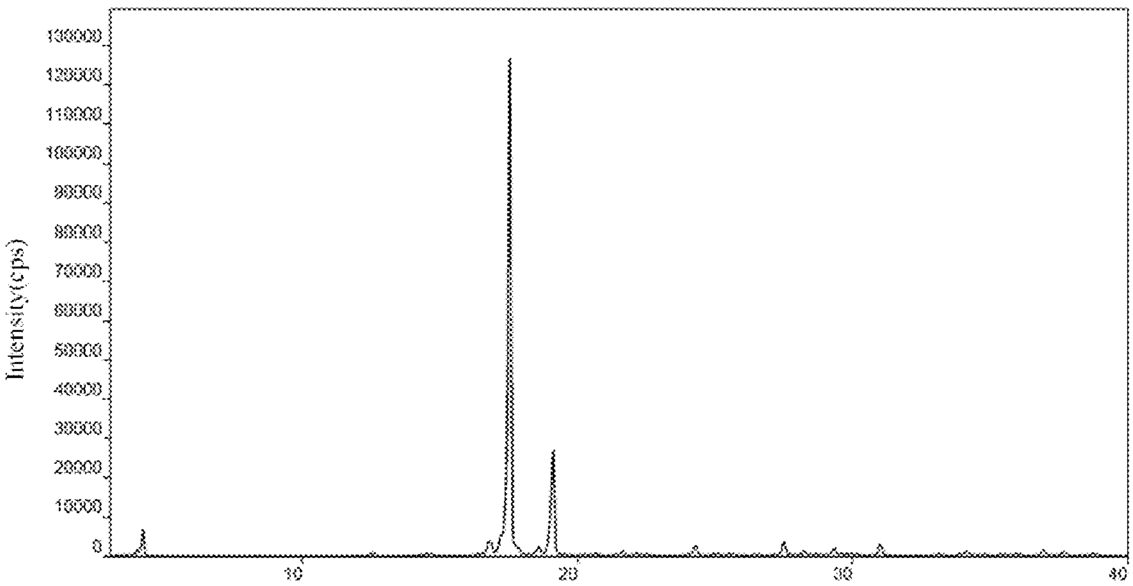
FIG. 5: X-ray powder diffraction pattern of taste masking powder (vortioxetine hemihydrobromide:UreleaseE100:PEG 6000=1:0.3:0.07).

X-ray powder diffraction pattern of Vortioxetine hemihydrobromide:Urelease E100:PEG 6000=1:0.3:0.07 taste masking powder is shown in FIG. 5.

Figure 4:
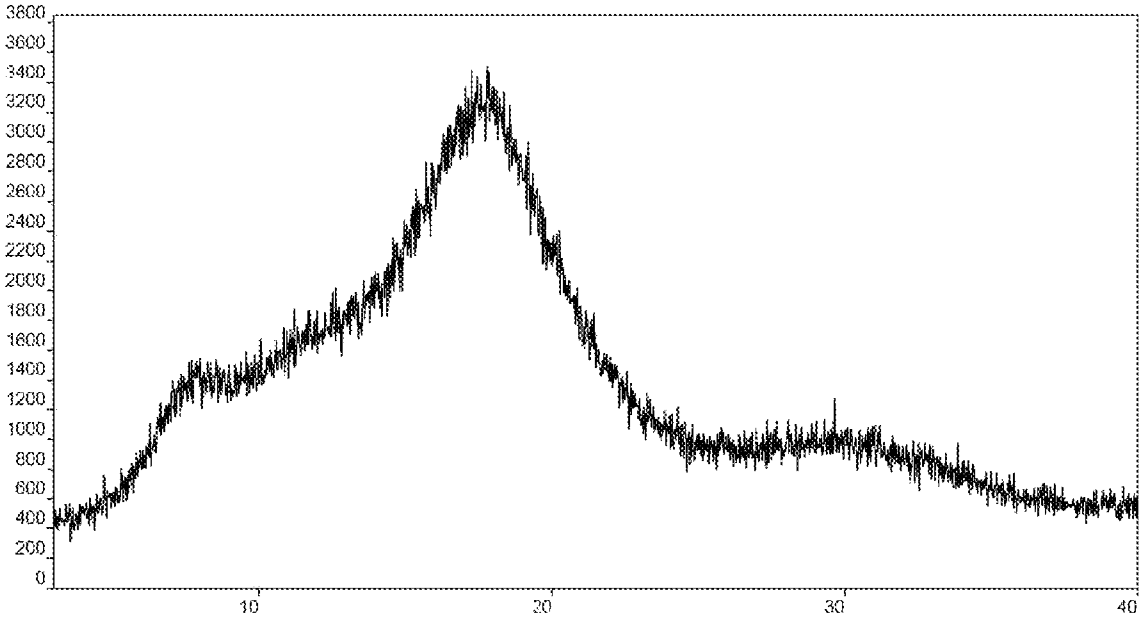
FIG. 4: X-ray powder diffraction pattern of UreleaseE100:PEG 6000=1:0.23 after spray drying.

X-ray powder diffraction pattern of Urelease E100:PEG 6000=1:0.23 powder after spray drying is shown in FIG. 4.

1b) Vortioxetine Hydrobromide Form α:UreleaseE100: PEG6000=1:0.3:0.07 Taste Masking Powder Preparation 30.09 g of UreleaseE100 and 7.05 g of PEG6000 were added to 470.20 g of medicinal ethanol, stirred to dissolve, set aside.

100.02 g of 100-200 mesh vortioxetine hydrobromide form α and 10.05 g of talc with particle size less than 325 mesh were added to the BWF-1G multifunctional fluid bed installed in the bottom spray coating mode. The air inlet volume and the height of the guide tube were adjusted to make the materials in a fluidized state, and the air inlet temperature was set 50-55° C., peristaltic pump speed was 5 rpm and atomization pressure was 1.0-1.5 atm. The coating liquid prepared by Urelease was sprayed into the fluid bed. After spraying, the materials were continued to fluidize for 30 minutes, then stopped heating, and waited until the temperature of the materials was cooled to room temperature. The materials were collected, and the powder with particle size 60-150 mesh was collected by sieving. 127.81 g of taste masking powder with yield 86.82% was obtained. The assay (calculated as vortioxetine) of powder was 52.77%.

If the materials were bonded during the preparation process, an appropriate amount of talcum powder could be added after the machine was stopped to ensure that the materials were in a fluidized state.

The taste masking powder equivalent to 20 mg of vortioxetine and the 100-mesh powder of vortioxetine hydrobromide form α equivalent to 20 mg vortioxetine were tasted and compared by 5 subjects. The irritation of taste masking powder was ameliorated.

Self-made sample: Instantaneous irritation ++, disappeared within 1-15 minutes after delayed irritation, and the bitterness was acceptable.

Reference sample: Instantaneous irritation +++, disappear after more than 30 minutes after delayed irritation, and the bitterness was unacceptable.

Detailed Information is Listed in Table 2:

TABLE 2

Comparison test of taste of vortioxetine hydrobromide form α taste masking powder

| | Instantaneous irritation | | Delayed irritation (min) | | Bitterness | | Grittiness | |
|---|---|---|---|---|---|---|---|---|
| Subject | Self-made sample | Reference sample | Self-made sample | Reference sample | Self-made sample | Reference sample | Self-made sample | Reference sample |
| Subject 1 | ++ | +++ | 1-15 | >30 | acceptable | unacceptable | N/A | N/A |
| Subject 2 | ++ | +++ | 1-15 | >30 | acceptable | unacceptable | N/A | N/A |
| Subject 3 | ++ | +++ | 1-15 | >30 | acceptable | unacceptable | N/A | N/A |
| Subject 4 | ++ | +++ | 1-15 | >30 | acceptable | unacceptable | N/A | N/A |
| Subject 5 | ++ | +++ | 1-15 | >30 | acceptable | unacceptable | N/A | N/A |

Figure 6:
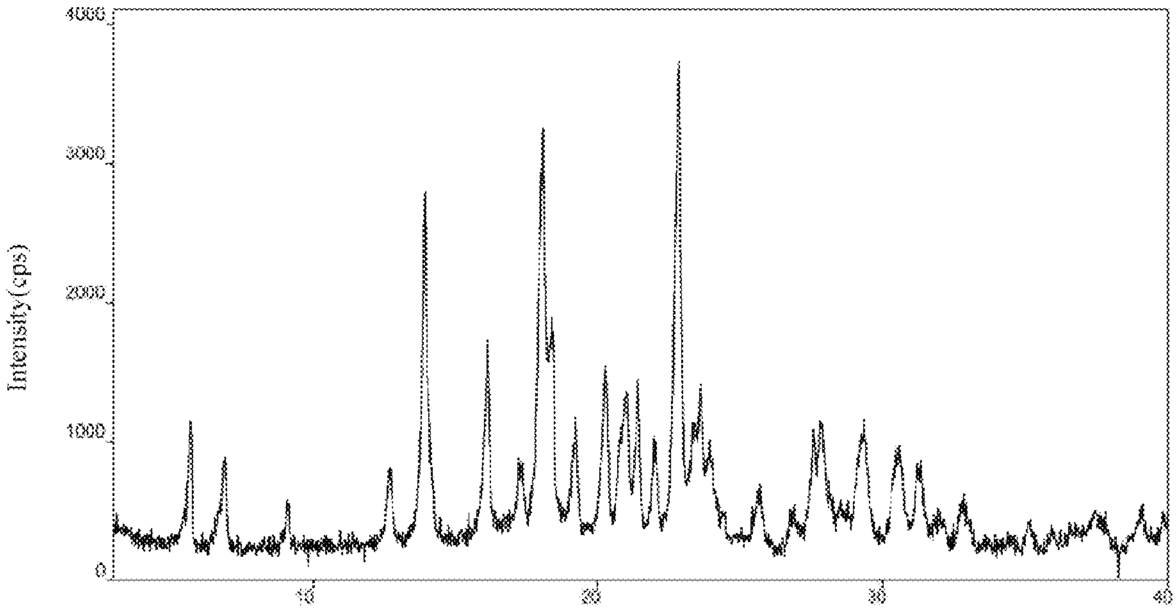
FIG. 6: X-ray powder diffraction pattern of taste masking powder (vortioxetine hydrobromide form α:UreleaseE100:PEG 6000=1:0.3:0.07).

X-ray powder diffraction pattern of Vortioxetine hydrobromide form α:Urelease E100:PEG 6000=1:0.3:0.07 taste masking powder is shown in FIG. 6. X-ray powder diffraction pattern of Urelease E100:PEG 6000=1:0.23 powder after spray drying is shown in FIG. 4.

1c) Vortioxetine hydrobromide form β:Urelease E100: PEG6000=1:0.3:0.07 taste masking powder preparation 30.00 g of Urelease E100 and 7.00 g of PEG6000 were added to 470.20 g of medicinal ethanol, stirred to dissolve, set aside.

100.00 g of 100-200 mesh vortioxetine hydrobromide form and 10.00 g of talc with particle size less than 325 mesh were added to the BWF-1G multifunctional fluid bed installed in the bottom spray coating mode. The air inlet volume and the height of the guide tube were adjusted to make the materials in a fluidized state, and the air inlet temperature was set 50-55° C., peristaltic pump speed was 5 rpm and atomization pressure was 1.0-1.5 atm. The coating liquid prepared by Urelease was sprayed into the fluid bed. After spraying, the materials were continued to fluidize for 30 minutes, then stopped heating, and waited until the temperature of the materials was cooled to room temperature. The materials were collected, and the powder with particle size 60-150 mesh was collected by sieving. 126.78 g of taste masking powder with yield 86.24% was obtained. The assay (calculated as vortioxetine) of powder was 53.13%.

If the materials were bonded during the preparation process, an appropriate amount of talcum powder could be added after the machine was stopped to ensure that the materials were in a fluidized state.

The taste masking powder equivalent to 20 mg of vortioxetine and the 100-mesh powder of vortioxetine hydrobromide form β equivalent to 20 mg vortioxetine were tasted and compared by 5 subjects. The irritation of taste masking powder was ameliorated.

Self-made sample: Instantaneous irritation ++, disappeared within 1-15 minutes after delayed irritation, and the bitterness was acceptable.

Reference sample: Instantaneous irritation +++, disappear after more than 30 minutes after delayed irritation, and the bitterness was unacceptable.

Detailed Information is Listed in Table 3:

TABLE 3

| Comparison test of taste of vortioxetine hydrobromide form β taste masking powder | | | | | | | | |
|---|---|---|---|---|---|---|---|---|
| | Instantaneous irritation | | Delayed irritation (min) | | Bitterness | | Grittiness | |
| Subject | Self-made sample | Reference sample | Self-made sample | Reference sample | Self-made sample | Reference sample | Self-made sample | Reference sample |
| Subject 1 | ++ | +++ | 1-15 | >30 | acceptable | unacceptable | N/A | N/A |
| Subject 2 | ++ | +++ | 1-15 | >30 | acceptable | unacceptable | N/A | N/A |
| Subject 3 | ++ | +++ | 1-15 | >30 | acceptable | unacceptable | N/A | N/A |
| Subject 4 | ++ | +++ | 1-15 | >30 | acceptable | unacceptable | N/A | N/A |
| Subject 5 | ++ | +++ | 1-15 | >30 | acceptable | unacceptable | N/A | N/A |

Figure 7:
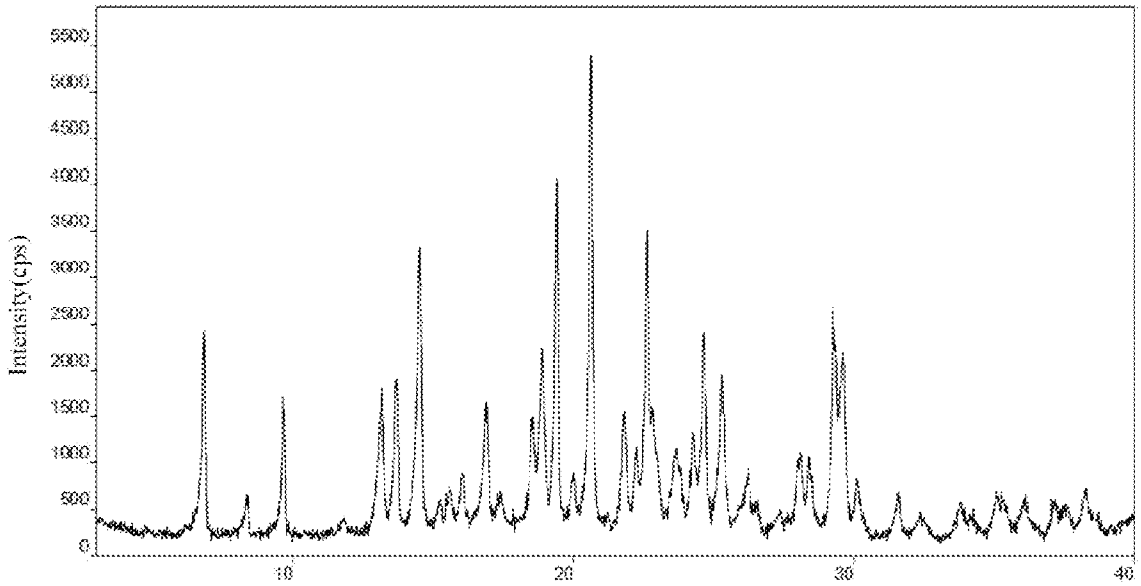
FIG. 7: X-ray powder diffraction pattern of taste masking powder (vortioxetine hydrobromide form β:UreleaseE100:PEG 6000=1:0.3:0.07).
Figure 8:
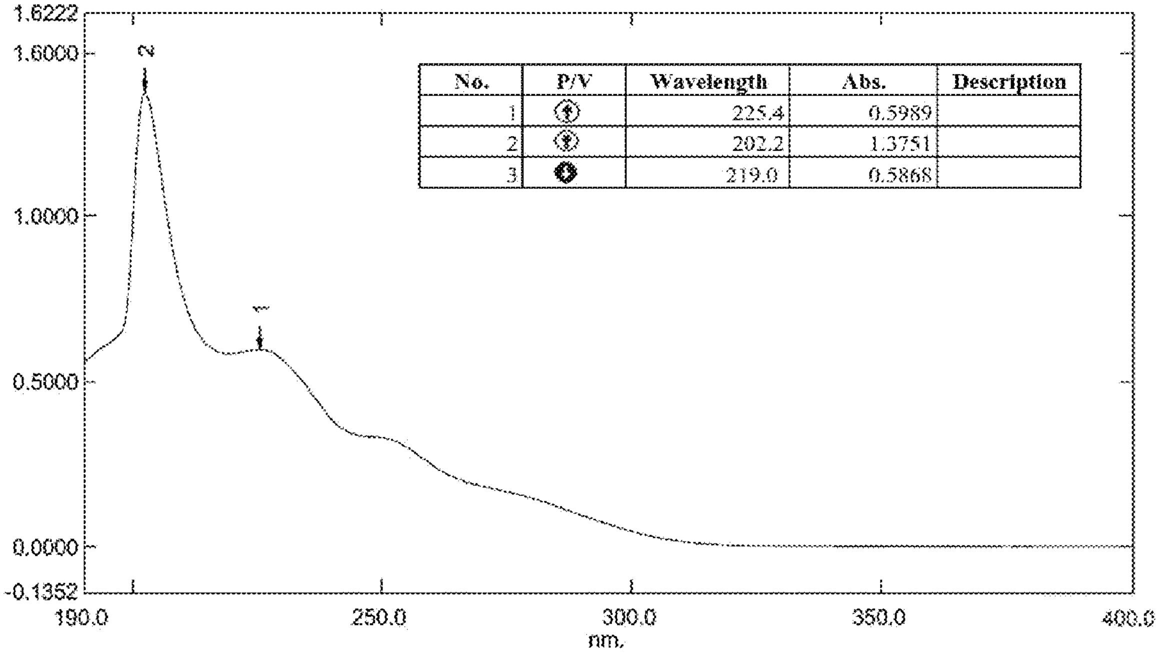
FIG. 8: UV spectrum of vortioxetine hydrobromide in 0.1N hydrochloric acid.
Figure 9:
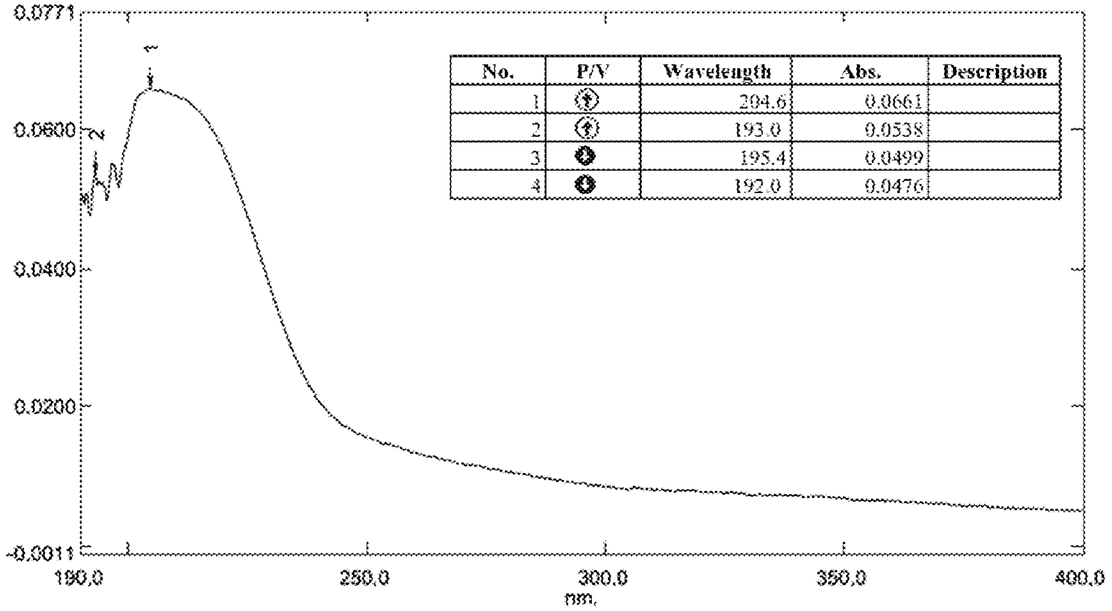
FIG. 9: UV spectrum of Eudragit E PO in 0.1N hydrochloric acid.
Figure 10:
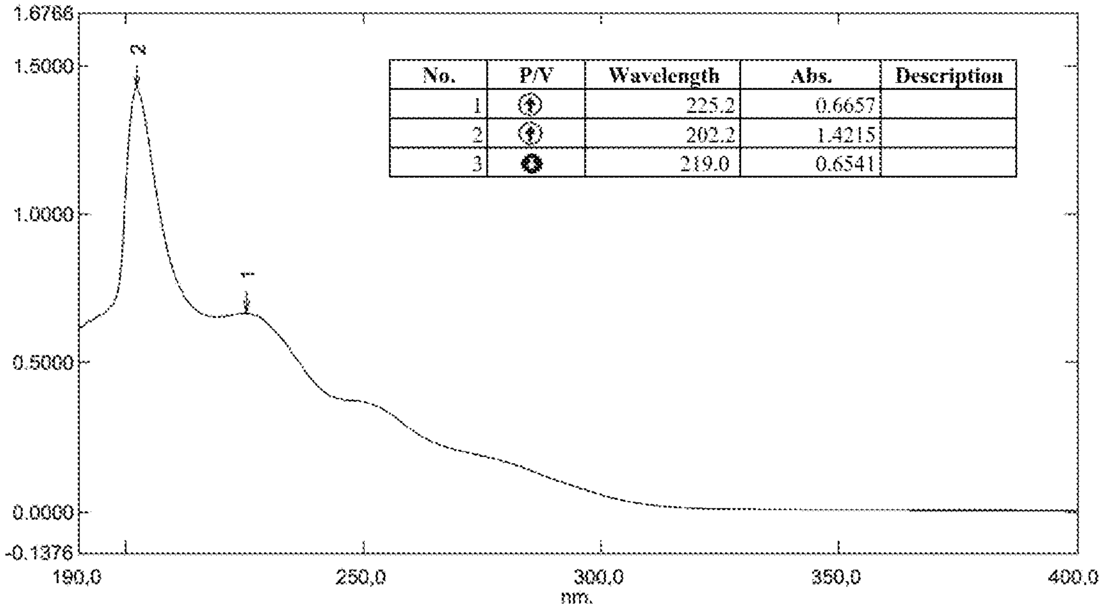
FIG. 10: UV spectrum of mixed powder (vortioxetine hydrobromide:Eudragit E PO=1:0.5) in 0.1N hydrochloric acid.
Figure 11:
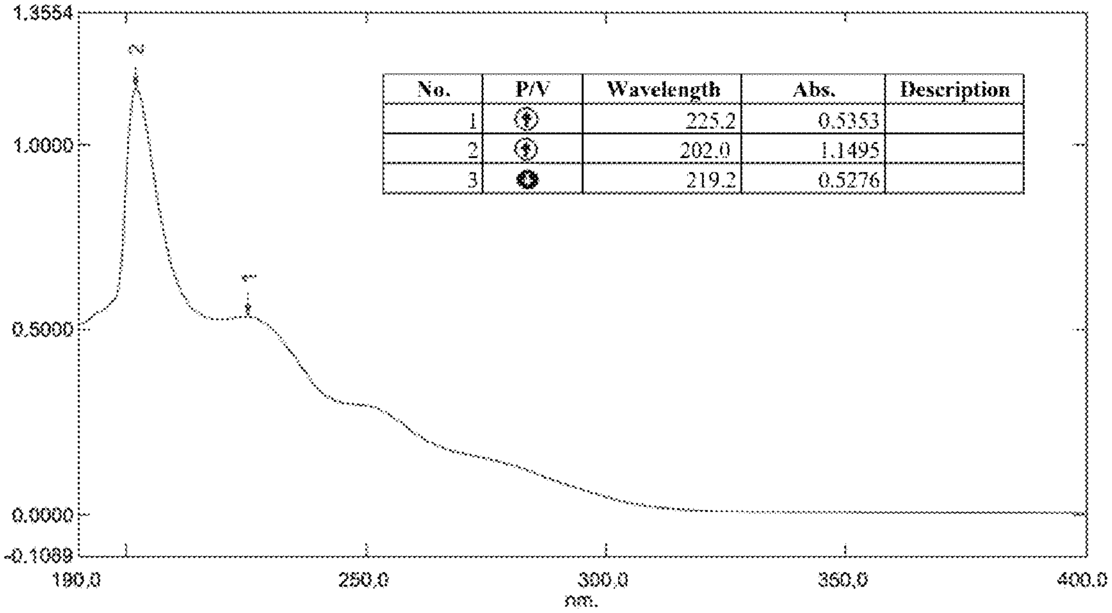
FIG. 11: UV spectrum of mixed hot melt powder (vortioxetine hydrobromide:Eudragit E PO=1:0.5) in 0.1N hydrochloric acid.
Figure 12:
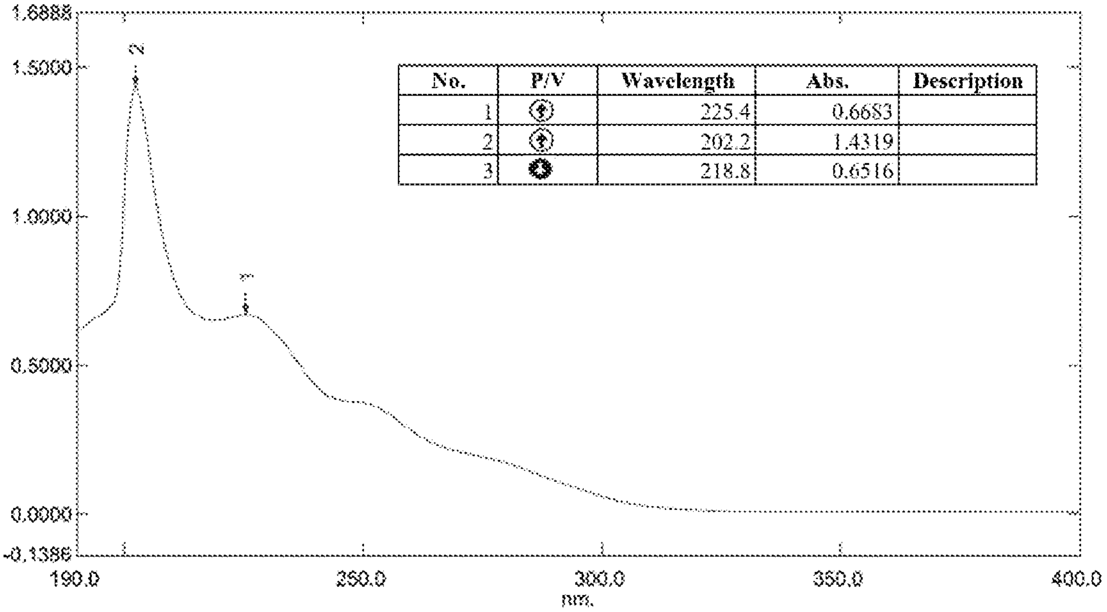
FIG. 12: UV spectrum of vortioxetine hemihydrobromide in 0.1N hydrochloric acid.
Figure 13:
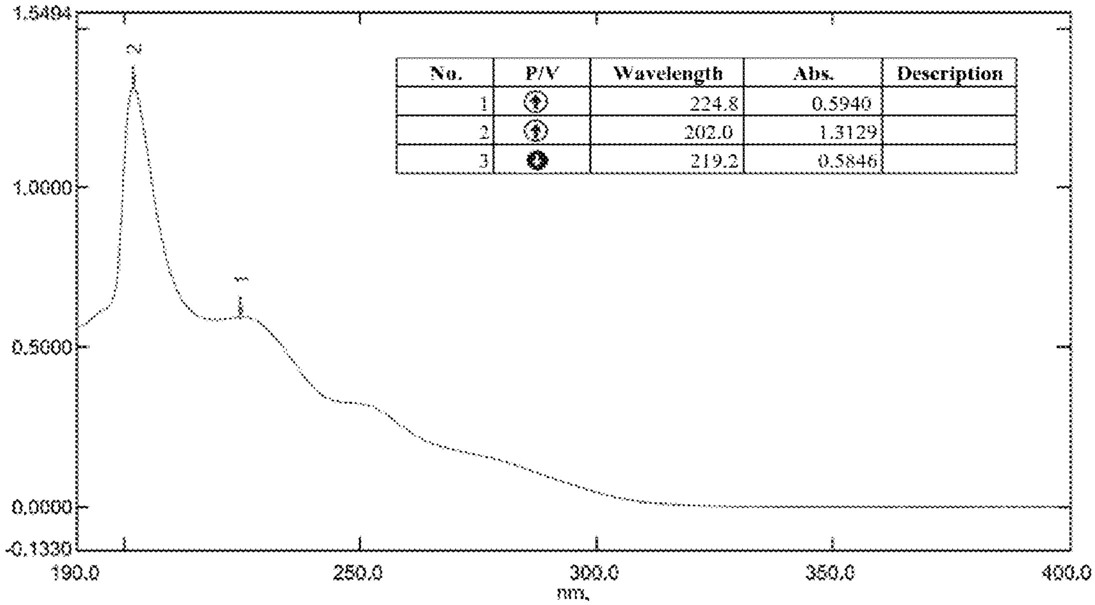
FIG. 13: UV spectrum of directly mixed powder (vortioxetine hemihydrobromide:Eudragit E PO=1:1.5) in 0.1N hydrochloric acid.
Figure 14:
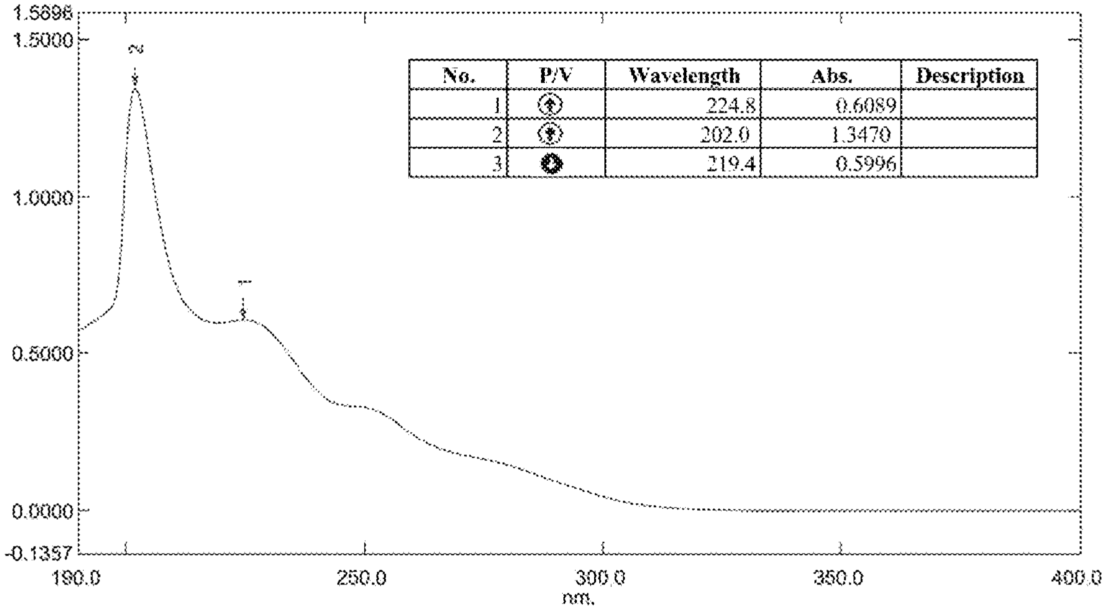
FIG. 14: UV spectrum of hot-melt powder (vortioxetine hemihydrobromide:Eudragit E PO=1:1.5) in 0.1N hydrochloric acid.
Figure 15:
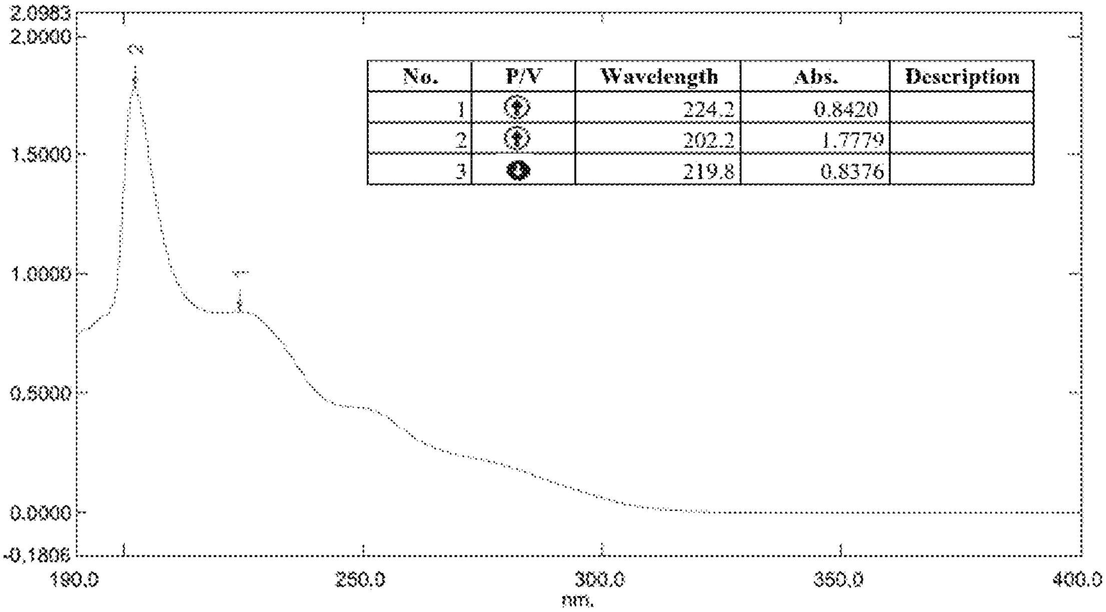
FIG. 15: UV spectrum of directly mixed powder (vortioxetine hemihydrobromide:Eudragit E PO=1:5) in 0.1N hydrochloric acid.
Figure 16:
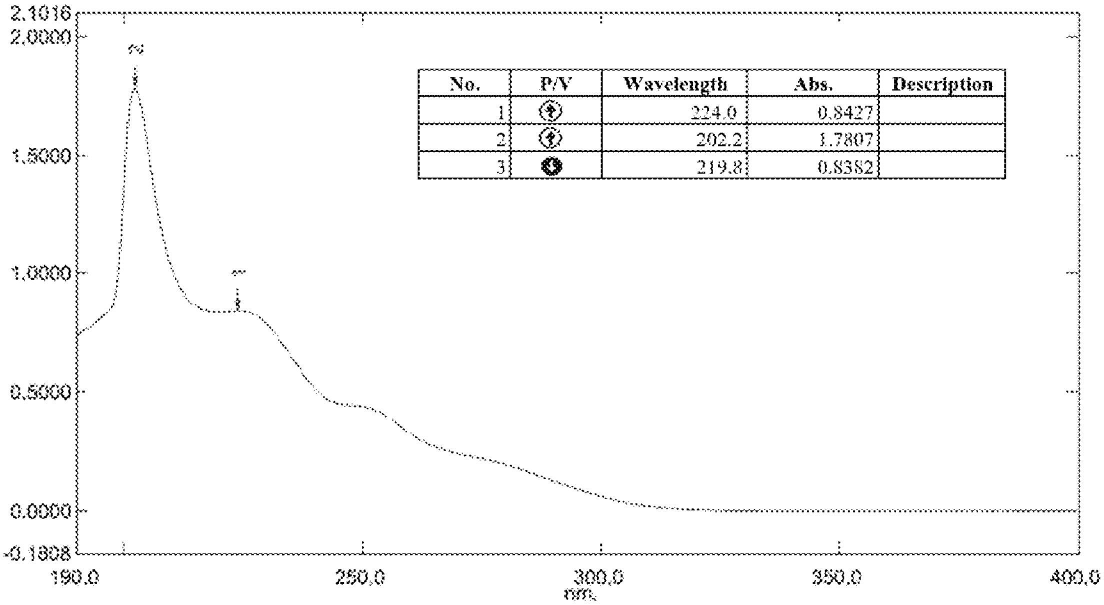
FIG. 16: UV spectrum of hot-melt powder (vortioxetine hemihydrobromide:Eudragit E PO=1:5) in 0.1N hydrochloric acid.
Figure 17:
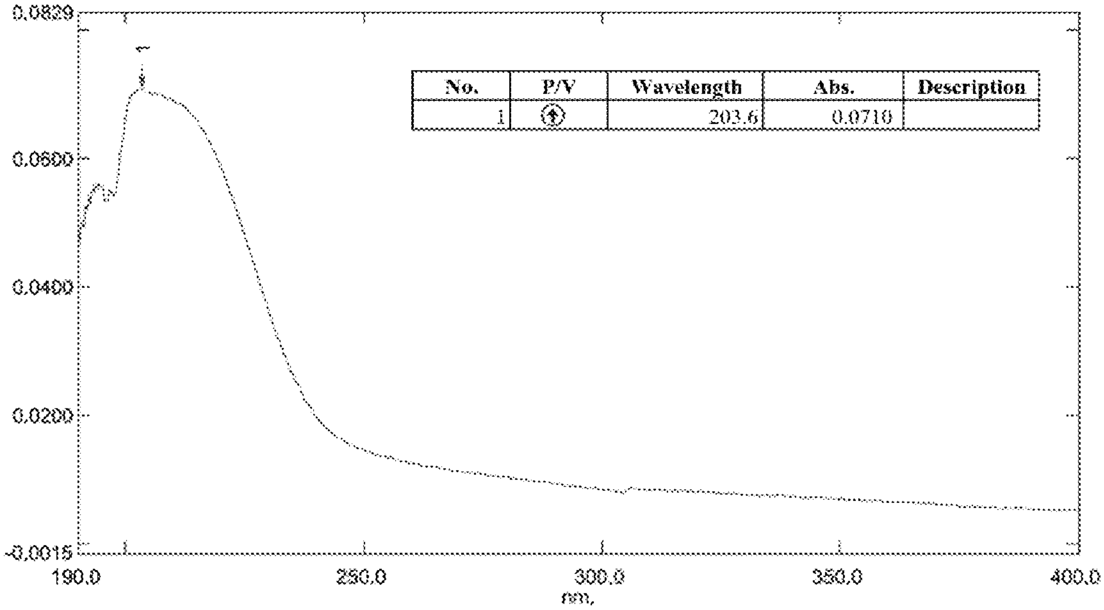
FIG. 17: UV spectrum of polyacrylic resin IV in 0.1N hydrochloric acid.
Figure 18:
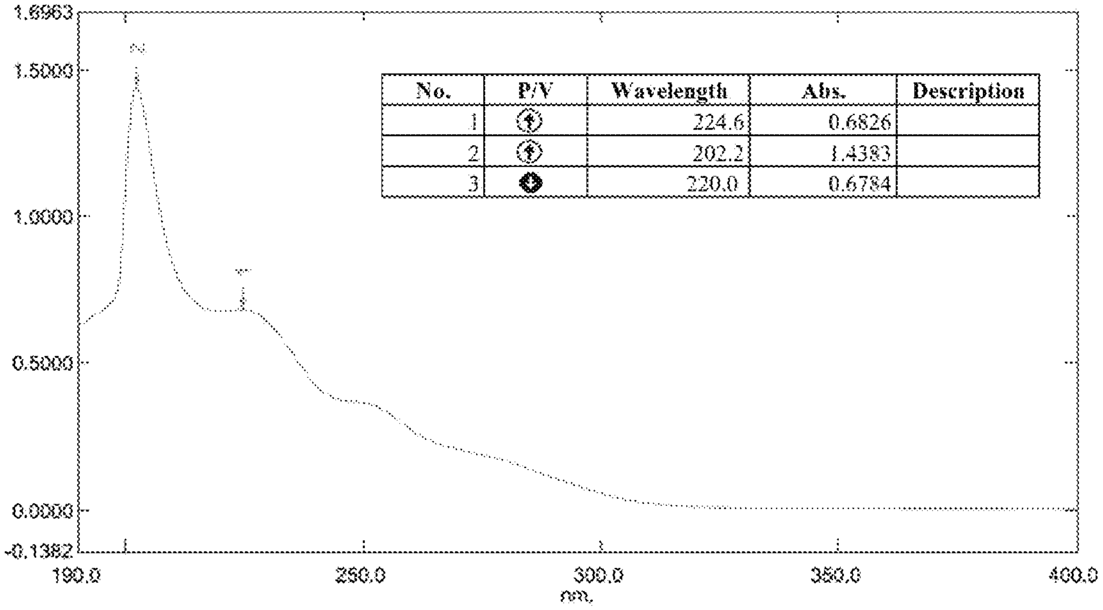
FIG. 18: UV spectrum of directly mixed powder (vortioxetine hydrobromide:polyacrylic resin IV=1:1.5) in 0.1N hydrochloric acid.
Figure 19:
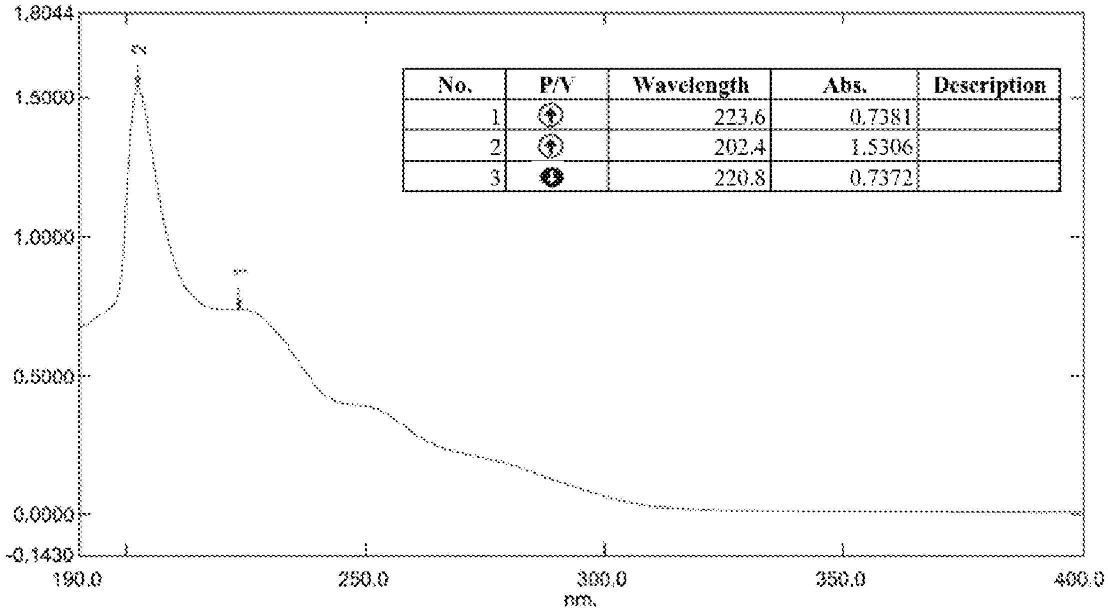
FIG. 19: UV spectrum of hot-melt powder (vortioxetine hydrobromide:polyacrylic resin IV=1:1.5) in 0.1N hydrochloric acid.

X-ray powder diffraction pattern of Vortioxetine hydrobromide form β: Urelease E100:PEG 6000=1:0.3:0.07 taste masking powder is shown in FIG. 7. X-ray powder diffraction pattern of Urelease E100:PEG 6000=1:0.23 after spray drying is shown in FIG. 4.

1d) Vortioxetine Hemihydrobromide:Ethyl Cellulose N10: PEG 6000=1:3:0.07 Taste Masking Powder Preparation 150.00 g of ethyl cellulose N10 and 3.50 g of PEG 6000 were added to 1500.00 g of medicinal ethanol, stirred to dissolve, set aside.

50.00 g of 100-200 mesh vortioxetine hemihydrobromide and 25.00 g of talc with particle size less than 325 mesh were added to the BWF-1G multifunctional fluid bed installed in the bottom spray coating mode. The air inlet volume and the height of the guide tube were adjusted to make the materials in a fluidized state, and the air inlet temperature was set 50-55° C., peristaltic pump speed was 5 rpm and atomization pressure was 1.0-1.5 atm. The coating liquid prepared by Urelease was sprayed into the fluid bed. After spraying, the materials were continued to fluidize for 30 minutes to remove residual ethanol, then stopped heating, and waited until the temperature of the materials was cooled to room temperature. The materials were collected, and the powder with particle size 60-150 mesh was collected by sieving. 162.91 g of taste masking powder with yield 71.30% was obtained. The assay (calculated as vortioxetine) of powder was 19.57%.

If the materials were bonded during the preparation process, an appropriate amount of talcum powder could be added after the machine was stopped to ensure that the materials were in a fluidized state.

The taste masking powder equivalent to 20 mg of vortioxetine and the 100-mesh powder of vortioxetine hemihydrobromide equivalent to 20 mg vortioxetine were tasted and compared by 5 subjects. The irritation of taste masking powder was ameliorated.

Self-made sample: Instantaneous irritation +, disappeared within 1-15 minutes after delayed irritation, and the bitterness was acceptable.

Reference sample: Instantaneous irritation +++, disappear after more than 30 minutes after delayed irritation, and the bitterness was unacceptable.

Detailed Information is Listed in Table 4:

TABLE 4

| Comparison test of taste of vortioxetine hemihydrobromide taste masking powder | | | | | | | | |
|---|---|---|---|---|---|---|---|---|
| | Instantaneous irritation | | Delayed irritation (min) | | Bitterness | | Grittiness | |
| Subject | Self-made sample | Reference sample | Self-made sample | Reference sample | Self-made sample | Reference sample | Self-made sample | Reference sample |
| Subject 1 | + | ++ | 1-15 | 15-30 | acceptable | unacceptable | N/A | N/A |
| Subject 2 | + | +++ | 1-15 | >30 | acceptable | unacceptable | N/A | N/A |
| Subject 3 | + | +++ | 1-15 | >30 | acceptable | unacceptable | N/A | N/A |
| Subject 4 | + | ++ | 1-15 | 15-30 | acceptable | acceptable | N/A | N/A |
| Subject 5 | + | +++ | 1-15 | >30 | acceptable | unacceptable | N/A | N/A |

1e) Vortioxetine Hemihydrobromide:Eudragit RL100:Meglumine=1:3:0.07 Taste Masking Powder Preparation 150.00 g of Eudragit RL100 and 3.50 g of meglumine were added to 1500.00 g of medicinal ethanol, stirred to dissolve, set aside.

50.00 g of 100-200 mesh vortioxetine hemihydrobromide and 25.00 g of talc with particle size less than 325 mesh were added to the BWF-1G multifunctional fluid bed installed in the bottom spray coating mode. The air inlet volume and the height of the guide tube were adjusted to make the materials in a fluidized state, and the air inlet temperature was set 50-55° C., peristaltic pump speed was 5 rpm and atomization pressure was 1.0-1.5 atm. The coating liquid prepared by Urelease was sprayed into the fluid bed. After spraying, the materials were continued to fluidize for 30 minutes to remove residual ethanol, then stopped heating, and waited until the temperature of the materials was cooled to room temperature. The materials were collected, and the powder with particle size 60-150 mesh was collected by sieving. The taste masking powder was obtained.

If the materials were bonded during the preparation process, an appropriate amount of talcum powder could be added after the machine was stopped to ensure that the materials were in a fluidized state.

The taste masking powder equivalent to 20 mg of vortioxetine and the 100-mesh powder of vortioxetine hemihydrobromide equivalent to 20 mg vortioxetine were tasted and compared by 5 subjects. The irritation of taste masking powder was ameliorated.

Self-made sample: Instantaneous irritation +, disappeared within 1-15 minutes after delayed irritation, and the bitterness was acceptable.

Reference sample: Instantaneous irritation +++, disappear after more than 30 minutes after delayed irritation, and the bitterness was unacceptable.

Detailed Information is Listed in Table 5:

TABLE 5

Comparison test of taste of vortioxetine hemihydrobromide taste masking powder

| Subject | Instantaneous irritation | | Delayed irritation (min) | | Bitterness | | Grittiness | |
|---|---|---|---|---|---|---|---|---|
| | Self-made sample | Reference sample | Self-made sample | Reference sample | Self-made sample | Reference sample | Self-made sample | Reference sample |
| Subject 1 | + | ++ | 1-15 | 15-30 | acceptable | unacceptable | N/A | N/A |
| Subject 2 | + | +++ | 1-15 | >30 | acceptable | unacceptable | N/A | N/A |
| Subject 3 | + | +++ | 1-15 | >30 | acceptable | unacceptable | N/A | N/A |
| Subject 4 | + | ++ | 1-15 | 15-30 | acceptable | acceptable | N/A | N/A |
| Subject 5 | + | +++ | 1-15 | >30 | acceptable | unacceptable | N/A | N/A |

to room temperature. The materials were collected, and the powder with particle size less than 80 mesh was collected by sieving. 7.81 g of taste masking powder with yield 43.98% was obtained. The assay (calculated as vortioxetine) of powder was 48.63%.

The remaining materials were lightly ground and then sieved to collect powder with particle size less than 80 mesh. 6.23 g of taste masking powder with yield 35.08% was obtained. The assay (calculated as vortioxetine) of powder was 49.38%.

The two kinds of taste masking powder equivalent to 20 mg of vortioxetine and the 100-mesh powder of vortioxetine hemihydrobromide equivalent to 20 mg vortioxetine were tasted and compared by 5 subjects. The irritation of taste masking powders was ameliorated significantly.

Example 2: Vortioxetine Hydrobromide+Coating Material Taste Masking Powder Preparation 2a) Vortioxetine Hemihydrobromide:Urelease E100=1:0.7 Taste Masking Powder Preparation 7.73 g of UreleaseE100 was added to 77.20 g of medicinal ethanol, stirred to dissolve, set aside.

10.02 g of 200 mesh vortioxetine hemihydrobromide was added to the above prepared solution, stirred to disperse. After sieving through 100 mesh stainless steel screen, the materials were collected and continued stirring to prevent sedimentation.

The BWF-1G multifunctional fluid bed was installed according to the top spray granulation mode, and the air volume was set 33 $m^3$, the inlet temperature was 50-55° C., the peristaltic pump speed was 8 rpm and the atomization pressure was 1.0-1.5 atm. The prepared suspension material was sprayed into the fluid bed, and the material status was observed at any time. After spraying, the materials were continued to fluidize for 30 minutes, then stopped heating, and waited until the temperature of the materials was cooled After mixing the two kinds of taste masking powder, the mixed taste masking powder equivalent to 20 mg of vortioxetine and the 100-mesh powder of vortioxetine hemihydrobromide equivalent to 20 mg vortioxetine were tasted by 5 subjects, which proved irritation of the treated vortioxetine taste masking powders were improved significantly.

Self-made sample 1: Instantaneous irritation +, disappeared within 1-15 minutes after delayed irritation, and the bitterness was acceptable.

Self-made sample 2: Instantaneous irritation +, disappeared within 1-15 minutes after delayed irritation, and the bitterness was acceptable.

Self-made mixed sample: Instantaneous irritation +, disappeared within 1-15 minutes after delayed irritation, and the bitterness was acceptable.

Reference sample: Instantaneous irritation +++, disappear after more than 30 minutes after delayed irritation, and the bitterness was unacceptable.

Detailed Information is Listed in Table 6:

TABLE 6

Comparison test of taste of vortioxetine hemihydrobromide taste masking powder

| Subject | Instantaneous irritation | | Delayed irritation (min) | | Bitterness | | Grittiness | |
|---|---|---|---|---|---|---|---|---|
| | Self-made mixed sample | Reference sample | Self-made mixed sample | Reference sample | Self-made mixed sample | Reference sample | Self-made mixed sample | Reference sample |
| Subject 1 | + | +++ | 1-15 | >30 | acceptable | unacceptable | N/A | N/A |
| Subject 2 | + | ++ | 1-15 | 15-30 | acceptable | unacceptable | N/A | N/A |
| Subject 3 | + | +++ | 1-15 | 1-15 | acceptable | unacceptable | N/A | N/A |
| Subject 4 | + | ++ | 1-15 | >30 | acceptable | unacceptable | N/A | N/A |
| Subject 5 | + | +++ | 1-15 | 15-30 | acceptable | unacceptable | N/A | N/A |

2b) Vortioxetine Hydrobromide:UreleaseE100=1:0.77 Taste Masking Powder Preparation 7.70 g of UreleaseE100 was added to 77.10 g of medicinal ethanol, stirred to dissolve, set aside.

10.00 g of 200 mesh vortioxetine hydrobromide was added to the above prepared solution, stirred to disperse. After sieving through 100 mesh stainless steel screen, the materials were collected and continued stirring to prevent sedimentation.

The BWF-1G multifunctional fluid bed was installed according to the top spray granulation mode, and the air volume was set 33 $m^3$, the inlet temperature was 50-55° C., the peristaltic pump speed was 8 rpm and the atomization pressure was 1.0-1.5 atm. The prepared suspension material was sprayed into the fluid bed, and the material status was observed at any time. After spraying, the materials were continued to fluidize for 30 minutes, then stopped heating, and waited until the temperature of the materials was cooled to room temperature. The materials were collected, and the powder with particle size less than 80 mesh was collected by sieving. 6.98 g of taste masking powder with yield 39.44% was obtained. The assay (calculated as vortioxetine) of powder was 44.63%.

The remaining materials were lightly ground and then sieved to collect powder with particle size less than 80 mesh. 5.93 g of taste masking powder with yield 33.50% was obtained. The assay (calculated as vortioxetine) of powder was 45.38%.

The two kinds of taste masking powder equivalent to 20 mg of vortioxetine and the 100-mesh powder of vortioxetine hydrobromide equivalent to 20 mg vortioxetine were tasted and compared by 5 subjects. The irritation of taste masking powders was ameliorated significantly.

After mixing the two kinds of taste masking powder, the mixed taste masking powder equivalent to 20 mg of vortioxetine and the 100-mesh powder of vortioxetine hydrobromide equivalent to 20 mg vortioxetine were tasted and compared by 5 subjects. The irritation of taste masking powders were ameliorated significantly.

Self-made sample 1: Instantaneous irritation +, disappeared within 1-15 minutes after delayed irritation, and the bitterness was acceptable.

Self-made sample 2: Instantaneous irritation +, disappeared within 1-15 minutes after delayed irritation, and the bitterness was acceptable.

Self-made mixed sample: Instantaneous irritation +, disappeared within 1-15 minutes after delayed irritation, and the bitterness was acceptable.

Reference sample: Instantaneous irritation +++, disappear after more than 30 minutes after delayed irritation, and the bitterness was unacceptable.

Detailed Information is Listed in Table 7:

2c) Vortioxetine Hemihydrobromide:Cellulose Acetate:PEG 6000=1:0.7:0.07 Taste Masking Powder Preparation 7.00 g of cellulose acetate and 0.70 g of PEG 6000 were added to 70.20 g of medicinal ethanol, stirred to dissolve, set aside.

10.00 g of 200 mesh vortioxetine hemihydrobromide was added to the above prepared solution, stirred to disperse. After sieving through 100 mesh stainless steel screen, the materials were collected and continued stirring to prevent sedimentation.

The BWF-1G multifunctional fluid bed was installed according to the top spray granulation mode, and the air volume was set 33 $m^3$, the inlet temperature was 50-55° C., the peristaltic pump speed was 8 rpm and the atomization pressure was 1.0-1.5 atm. The prepared suspension material was sprayed into the fluid bed, and the material status was observed at any time. After spraying, the materials were continued to fluidize for 30 minutes, then stopped heating, and waited until the temperature of the materials was cooled to room temperature. The materials were collected, and the powder with particle size less than 80 mesh was collected by sieving. 6.97 g of taste masking powder with yield 40.76% was obtained. The assay (calculated as vortioxetine) of powder was 47.93%.

The remaining materials were lightly ground and then sieved to collect powder with particle size less than 80 mesh. 6.00 g of taste masking powder with yield 33.90% was obtained. The assay (calculated as vortioxetine) of powder was 48.98%.

The two kinds of taste masking powder equivalent to 20 mg of vortioxetine and the 100-mesh powder of vortioxetine hemihydrobromide equivalent to 20 mg vortioxetine were tasted and compared by 5 subjects. The irritation of taste masking powders were ameliorated significantly.

After mixing the two kinds of taste masking powder, the mixed taste masking powder equivalent to 20 mg of vortioxetine and the 100-mesh powder of vortioxetine hemihydrobromide equivalent to 20 mg vortioxetine were tasted by 5 subjects, which proved irritation of the treated vortioxetine taste masking powders were improved significantly.

Self-made sample 1: Instantaneous irritation +, disappeared within 1-15 minutes after delayed irritation, and the bitterness was acceptable.

Self-made sample 2: Instantaneous irritation +, disappeared within 1-15 minutes after delayed irritation, and the bitterness was acceptable.

Self-made mixed sample: Instantaneous irritation +, disappeared within 1-15 minutes after delayed irritation, and the bitterness was acceptable.

Reference sample: Instantaneous irritation ++, disappear after more than 30 minutes after delayed irritation, and the bitterness was unacceptable.

TABLE 7

Comparison test of taste of vortioxetine hydrobromide taste masking powder

| Subject | Instantaneous irritation | | Delayed irritation (min) | | Bitterness | | Grittiness | |
|---|---|---|---|---|---|---|---|---|
| | Self-made mixed sample | Reference sample | Self-made mixed sample | Reference sample | Self-made mixed sample | Reference sample | Self-made mixed sample | Reference sample |
| Subject 1 | + | +++ | 1-15 | >30 | acceptable | unacceptable | N/A | N/A |
| Subject 2 | + | ++ | 1-15 | >30 | acceptable | unacceptable | N/A | N/A |
| Subject 3 | ++ | +++ | 1-15 | >30 | acceptable | unacceptable | N/A | N/A |
| Subject 4 | + | ++ | 1-15 | >30 | acceptable | unacceptable | N/A | N/A |
| Subject 5 | + | +++ | 1-15 | >30 | acceptable | unacceptable | N/A | N/A |

Detailed Information is Listed in Table 8:

TABLE 8

Comparison test of taste of vortioxetine hemihydrobromide taste masking powder

| Subject | Instantaneous irritation | | Delayed irritation (min) | | Bitterness | | Grittiness | |
|---|---|---|---|---|---|---|---|---|
| | Self-made mixed sample | Reference sample | Self-made mixed sample | Reference sample | Self-made mixed sample | Reference sample | Self-made mixed sample | Reference sample |
| Subject 1 | + | +++ | 1-15 | >30 | acceptable | unacceptable | N/A | N/A |
| Subject 2 | + | ++ | 1-15 | 15-30 | acceptable | unacceptable | N/A | N/A |
| Subject 3 | ++ | +++ | 1-15 | 1-15 | acceptable | unacceptable | N/A | N/A |
| Subject 4 | + | ++ | 1-15 | >30 | acceptable | unacceptable | N/A | N/A |
| Subject 5 | + | +++ | 1-15 | 15-30 | acceptable | unacceptable | N/A | N/A |

2d) Vortioxetine Hemihydrobromide:Polyvinyl Alcohol (Low Viscosity)=1:0.7 Taste Masking Powder Preparation 7.00 g of polyvinyl alcohol (low viscosity) was added to 100.00 g of purified water, stirred in 90° C. water bath to dissolve, cooled to room temperature, 0.07 g of potassium citrate was added, stirred to dissolve, set aside.

10.00 g of 200 mesh vortioxetine hemihydrobromide was added to the above prepared solution, stirred to disperse. After sieving through 100 mesh stainless steel screen, the materials were collected and continued stirring to prevent sedimentation.

The BWF-1G multifunctional fluid bed was installed according to the top spray granulation mode, and the air volume was set 30-33 $m^3$, the inlet temperature was 60-55° C., the peristaltic pump speed was 8 rpm and the atomization pressure was 1.0-1.5 atm. The prepared suspension material was sprayed into the fluid bed, and the material status was observed at any time. After spraying, the materials were continued to fluidize for 30 minutes, then stopped heating, and waited until the temperature of the materials was cooled to room temperature. The materials were collected, and the powder with particle size less than 80 mesh was collected by sieving. 12.79 g of taste masking powder with yield 75.24% was obtained. The assay (calculated as vortioxetine) of powder was 50.99%.

The taste masking powder equivalent to 20 mg of vortioxetine and the 100-mesh powder of vortioxetine hemihydrobromide equivalent to 20 mg vortioxetine were tasted and compared by 5 subjects. The irritation of taste masking powder was ameliorated significantly.

Self-made sample: Instantaneous irritation +, disappeared within 1-15 minutes after delayed irritation, and the bitterness was acceptable.

Reference sample: Instantaneous irritation ++, disappear after more than 30 minutes after delayed irritation, and the bitterness was unacceptable.

Detailed Information is Listed in Table 9:

TABLE 9

Comparison test of taste of vortioxetine hemihydrobromide taste masking powder

| Subject | Instantaneous irritation | | Delayed irritation (min) | | Bitterness | | Grittiness | |
|---|---|---|---|---|---|---|---|---|
| | Self-made sample | Reference sample | Self-made sample | Reference sample | Self-made sample | Reference sample | Self-made sample | Reference sample |
| Subject 1 | + | ++ | 1-15 | >30 | acceptable | unacceptable | N/A | N/A |
| Subject 2 | + | ++ | 1-15 | 15-30 | acceptable | unacceptable | N/A | N/A |
| Subject 3 | ++ | +++ | 1-15 | 1-15 | acceptable | unacceptable | N/A | N/A |
| Subject 4 | + | ++ | 1-15 | >30 | acceptable | unacceptable | N/A | N/A |
| Subject 5 | ++ | ++ | 1-15 | 15-30 | acceptable | unacceptable | N/A | N/A |

Example 3: Vortioxetine Hemihydrobromide:Coating Material=1:1 Taste Masking Powder Preparation 3a) Vortioxetine Hemihydrobromide:Eudragit E100:PEG 6000=1:1:0.07 Taste Masking Powder Preparation 10.00 g of Eudragit E100 and 0.70 g of PEG 6000 were added to 70.00 g of medicinal ethanol, stirred to dissolve, set aside.

10.01 g of 200 mesh vortioxetine hemihydrobromide was added to the above prepared solution, stirred to disperse. After sieving through 100 mesh stainless steel screen, the materials were collected and continued stirring to prevent sedimentation.

The BWF-1G multifunctional fluid bed was installed according to the top spray granulation mode, and the air volume was set 33 $m^3$, the inlet temperature was 50-55° C., the peristaltic pump speed was 8 rpm and the atomization pressure was 1.0-1.5 atm. The prepared suspension material was sprayed into the fluid bed, and the material status was observed at any time. After spraying, the materials were continued to fluidize for 30 minutes, then stopped heating, and waited until the temperature of the materials was cooled to room temperature. The materials were collected, and the powder with particle size less than 80 mesh was collected by sieving. 13.78 g of taste masking powder with yield 66.54% was obtained. The assay (calculated as vortioxetine) of powder was 41.79%.

The taste masking powder equivalent to 20 mg of vortioxetine and the 100-mesh powder of vortioxetine hemihydrobromide equivalent to 20 mg vortioxetine were tasted and compared by 5 subjects. The irritation of taste masking powder was ameliorated significantly.

Self-made sample: Instantaneous irritation +, disappeared within 1-15 minutes after delayed irritation, and the bitterness was acceptable.

Reference sample: Instantaneous irritation ++, disappear after more than 30 minutes after delayed irritation, and the bitterness was unacceptable.

Detailed Information is Listed in Table 10:

TABLE 10

Comparison test of taste of vortioxetine hemihydrobromide taste masking powder

| Subject | Instantaneous irritation | | Delayed irritation (min) | | Bitterness | | Grittiness | |
|---|---|---|---|---|---|---|---|---|
| | Self-made sample | Reference sample | Self-made sample | Reference sample | Self-made sample | Reference sample | Self-made sample | Reference sample |
| Subject 1 | + | +++ | 1-15 | >30 | acceptable | unacceptable | N/A | N/A |
| Subject 2 | + | ++ | 1-15 | 15-30 | acceptable | unacceptable | N/A | N/A |
| Subject 3 | + | ++ | 1-15 | >30 | acceptable | unacceptable | N/A | N/A |
| Subject 4 | + | +++ | 1-15 | 1-15 | acceptable | unacceptable | N/A | N/A |
| Subject 5 | + | +++ | 1-15 | 1-15 | acceptable | unacceptable | N/A | N/A |

3b) Vortioxetine Hemihydrobromide:Eudragit L100:PEG 6000=1:1:0.07 Taste Masking Powder Preparation 10.00 g of Eudragit L100 and 0.70 g of PEG 6000 were added to 70.00 g of medicinal ethanol, stirred to dissolve, set aside.

10.00 g of 200 mesh vortioxetine hemihydrobromide was added to the above prepared solution, stirred to disperse. After sieving through 100 mesh stainless steel screen, the materials were collected and continued stirring to prevent sedimentation.

The BWF-1G multifunctional fluid bed was installed according to the top spray granulation mode, and the air volume was set 33 $m^3$, the inlet temperature was 50-55° C., the peristaltic pump speed was 8 rpm and the atomization pressure was 1.0-1.5 atm. The prepared suspension material was sprayed into the fluid bed, and the material status was observed at any time. After spraying, the materials were continued to fluidize for 30 minutes, then stopped heating, and waited until the temperature of the materials was cooled to room temperature. The materials were collected, and the powder with particle size less than 80 mesh was collected by sieving. 14.14 g of taste masking powder with yield 68.31% was obtained. The assay (calculated as vortioxetine) of powder was 42.01%.

The taste masking powder equivalent to 20 mg of vortioxetine and the 100-mesh powder of vortioxetine hemihydrobromide equivalent to 20 mg vortioxetine were tasted and compared by 5 subjects. The irritation of taste masking powders was ameliorated significantly and almost non-irritating.

Self-made sample: Instantaneous irritation +, disappeared within 1-15 minutes after delayed irritation, and the bitterness was acceptable.

Reference sample: Instantaneous irritation ++, disappear after more than 30 minutes after delayed irritation, and the bitterness was unacceptable.

Detailed Information is Listed in Table 11:

TABLE 11

Comparison test of taste of vortioxetine hemihydrobromide taste masking powder

| Subject | Instantaneous irritation | | Delayed irritation (min) | | Bitterness | | Grittiness | |
|---|---|---|---|---|---|---|---|---|
| | Self-made sample | Reference sample | Self-made sample | Reference sample | Self-made sample | Reference sample | Self-made sample | Reference sample |
| Subject 1 | + | +++ | 1-15 | >30 | acceptable | unacceptable | N/A | N/A |
| Subject 2 | + | ++ | 1-15 | 15-30 | acceptable | unacceptable | N/A | N/A |
| Subject 3 | + | ++ | 1-15 | >30 | acceptable | unacceptable | N/A | N/A |
| Subject 4 | + | +++ | 1-15 | 1-15 | acceptable | unacceptable | N/A | N/A |
| Subject 5 | + | +++ | 1-15 | 1-15 | acceptable | unacceptable | N/A | N/A |

3c) Vortioxetine Hemihydrobromide:Copovidone AV64=1:1 Taste Masking Powder Preparation 10.00 g of copovidone AV64 was added to 70.00 g of medicinal ethanol, stirred to dissolve, set aside.

10.00 g of 200 mesh vortioxetine hemihydrobromide was added to the above prepared solution, stirred to disperse. After sieving through 100 mesh stainless steel screen, the materials were collected and continued stirring to prevent sedimentation.

The BWF-1G multifunctional fluid bed was installed according to the top spray granulation mode, and the air volume was set 33 $m^3$, the inlet temperature was 50-55° C., the peristaltic pump speed was 8 rpm and the atomization pressure was 1.0-1.5 atm. The prepared suspension material was sprayed into the fluid bed, and the material status was observed at any time. After spraying, the materials were continued to fluidize for 30 minutes, then stopped heating, and waited until the temperature of the materials was cooled to room temperature. The materials were collected, and the powder with particle size less than 80 mesh was collected by sieving. 14.16 g of taste masking powder with yield 70.80% was obtained. The assay (calculated as vortioxetine) of powder was 42.78%.

The taste masking powder equivalent to 20 mg of vortioxetine and the 100-mesh powder of vortioxetine hemihydrobromide equivalent to 20 mg vortioxetine were tasted and compared by 5 subjects. The irritation of taste masking powder was ameliorated significantly.

Self-made sample: Instantaneous irritation +, disappeared within 1-15 minutes after delayed irritation, and the bitterness was acceptable.

Reference sample: Instantaneous irritation ++, disappear after more than 30 minutes after delayed irritation, and the bitterness was unacceptable.

Detailed Information is Listed in Table 12:

TABLE 12

Comparison test of taste of vortioxetine hemihydrobromide taste masking powder

| Subject | Instantaneous irritation | | Delayed irritation (min) | | Bitterness | | Grittiness | |
|---|---|---|---|---|---|---|---|---|
| | Self-made sample | Reference sample | Self-made sample | Reference sample | Self-made sample | Reference sample | Self-made sample | Reference sample |
| Subject 1 | ++ | +++ | 1-15 | >30 | acceptable | unacceptable | N/A | N/A |
| Subject 2 | + | ++ | 1-15 | 15-30 | acceptable | unacceptable | N/A | N/A |
| Subject 3 | ++ | ++ | 1-15 | >30 | acceptable | unacceptable | N/A | N/A |
| Subject 4 | + | +++ | 1-15 | >30 | acceptable | unacceptable | N/A | N/A |
| Subject 5 | + | ++ | 1-15 | >30 | acceptable | unacceptable | N/A | N/A |

Example 4: Vortioxetine Hydrobromide:Eudragit=1:0.5 Mixture Preparation

4a) Vortioxetine Hemihydrobromide:Eudragit E PO=1:0.5 Mixture Preparation 5.00 g of vortioxetine hemihydrobromide that had passed through a 200-mesh stainless steel sieve and 2.50 g of Eudragit E PO were placed in a clean and dry 50 ml screw-top glass reagent bottle. The mixture was mixed with Vortex-2 vortex mixer for 5 minutes. After passing through a 100-mesh stainless steel sieve, the mixture was continued to mix with Vortex-2 vortex mixer for 5 minutes. 0.50 g of the sample was took out for testing. The remaining materials were collected and piled up in a 75 mm diameter stainless steel tray, and the stainless steel tray was placed in DHG-9070A hot air circulating oven at 120-130° C. After heating for 30 minutes, the material became a semi-fluid state. After it was taken out and left to cool, it was milled through a 100-mesh stainless steel sieve with a BJ-300A multifunctional pulverizer several times to obtain a 1:0.5 mixture powder.

The mixture powder equivalent to 20 mg of vortioxetine and the 100-mesh powder of vortioxetine hemihydrobromide equivalent to 20 mg vortioxetine were tasted and compared by 5 subjects. The irritation of mixture powder was ameliorated.

Self-made sample: Instantaneous irritation ++, disappeared within 1-15 minutes after delayed irritation, and the bitterness was acceptable.

Reference sample: Instantaneous irritation +++, disappear after more than 30 minutes after delayed irritation, and the bitterness was unacceptable.

Detailed Information is Listed in Table 13:

TABLE 13

Comparison test of taste of vortioxetine hemihydrobromide solid dispersion

| Subject | Instantaneous irritation | | Delayed irritation (min) | | Bitterness | | Grittiness | |
|---|---|---|---|---|---|---|---|---|
| | Self-made sample | Reference sample | Self-made sample | Reference sample | Self-made sample | Reference sample | Self-made sample | Reference sample |
| Subject 1 | ++ | +++ | 1-15 | >30 | acceptable | unacceptable | N/A | N/A |
| Subject 2 | ++ | ++ | 1-15 | 15-30 | acceptable | unacceptable | N/A | N/A |
| Subject 3 | + | +++ | 1-15 | >30 | acceptable | unacceptable | N/A | N/A |
| Subject 4 | ++ | +++ | 1-15 | >30 | acceptable | unacceptable | N/A | N/A |
| Subject 5 | + | ++ | 1-15 | 15-30 | acceptable | unacceptable | N/A | N/A |

4b) Vortioxetine Hydrobromide:Eudragit E PO=1:0.5 Mixture Preparation 5.00 g of vortioxetine hydrobromide that had passed through a 200-mesh stainless steel sieve and 2.50 g of Eudragit E PO were placed in a clean and dry 50 ml screw-top glass reagent bottle. The mixture was mixed with Vortex-2 vortex mixer for 5 minutes. After passing through a 100-mesh stainless steel sieve, the mixture was continued to mix with Vortex-2 vortex mixer for 5 minutes. 0.50 g of the sample was took out for testing. The remaining materials were collected and piled up in a 75 mm diameter stainless steel tray, and the stainless steel tray was placed in DHG-9070A hot air circulating oven at 120-130° C. After heating for 30 minutes, the material became a semi-fluid state. After it was taken out and left to cool, it was milled through a 100-mesh stainless steel sieve with a BJ-300A multifunctional pulverizer several times to obtain a 1:0.5 mixture powder.

The mixture powder equivalent to 20 mg of vortioxetine and the 100-mesh powder of vortioxetine hydrobromide equivalent to 20 mg vortioxetine were tasted and compared by 5 subjects. The irritation of mixture powder was ameliorated.

Self-made sample: Instantaneous irritation ++, disappeared within 1-15 minutes after delayed irritation, and the bitterness was acceptable.

Reference sample: Instantaneous irritation +++, disappear after more than 30 minutes after delayed irritation, and the bitterness was unacceptable.

Detailed Information is Listed in Table 14:

TABLE 14

Comparison test of taste of vortioxetine hydrobromide solid dispersion

| Subject | Instantaneous irritation Self-made sample | Instantaneous irritation Reference sample | Delayed irritation (min) Self-made sample | Delayed irritation (min) Reference sample | Bitterness Self-made sample | Bitterness Reference sample | Grittiness Self-made sample | Grittiness Reference sample |
|---|---|---|---|---|---|---|---|---|
| Subject 1 | ++ | +++ | 1-15 | >30 | acceptable | unacceptable | N/A | N/A |
| Subject 2 | ++ | +++ | 1-15 | >30 | acceptable | unacceptable | N/A | N/A |
| Subject 3 | ++ | +++ | >30 | >30 | acceptable | unacceptable | N/A | N/A |
| Subject 4 | ++ | +++ | 1-15 | >30 | acceptable | unacceptable | N/A | N/A |
| Subject 5 | +++ | +++ | 1-15 | >30 | acceptable | unacceptable | N/A | N/A |

The UV scan showed that the maximum absorption wavelength and peak intensity of the treated material vortioxetine did not change significantly. The results are shown in FIG. 8, FIG. 9, FIG. 10 and FIG. 11.

4c) Vortioxetine Hydrobromide:Eudragit RS PO=1:0.5 Mixture Preparation 5.00 g of vortioxetine hydrobromide that had passed through a 200-mesh stainless steel sieve and 2.50 g of Eudragit RS PO were placed in a clean and dry 50 ml screw-top glass reagent bottle. The mixture was mixed with Vortex-2 vortex mixer for 5 minutes. After passing through a 100-mesh stainless steel sieve, the mixture was continued to mix with Vortex-2 vortex mixer for 5 minutes. 0.50 g of the sample was took out for testing. The remaining materials were collected and piled up in a 75 mm diameter stainless steel tray, and the stainless steel tray was placed in DHG-9070A hot air circulating oven at 120-130° C. After heating for 30 minutes, the material became a semi-fluid state. After it was taken out and left to cool, it was milled through a 100-mesh stainless steel sieve with a BJ-300A multifunctional pulverizer several times to obtain a 1:0.5 mixture powder.

The mixture powder equivalent to 20 mg of vortioxetine and the 100-mesh powder of vortioxetine hydrobromide equivalent to 20 mg vortioxetine were tasted and compared by 5 subjects. The irritation of mixture powder was ameliorated.

Self-made sample: Instantaneous irritation ++, disappeared within 1-15 minutes after delayed irritation, and the bitterness was acceptable.

Reference sample: Instantaneous irritation +++, disappear after more than 30 minutes after delayed irritation, and the bitterness was unacceptable.

Detailed Information is Listed in Table 15:

TABLE 15

Comparison test of taste of vortioxetine hydrobromide solid dispersion

| Subject | Instantaneous irritation Self-made sample | Instantaneous irritation Reference sample | Delayed irritation (min) Self-made sample | Delayed irritation (min) Reference sample | Bitterness Self-made sample | Bitterness Reference sample | Grittiness Self-made sample | Grittiness Reference sample |
|---|---|---|---|---|---|---|---|---|
| Subject 1 | ++ | +++ | 1-15 | >30 | acceptable | unacceptable | N/A | N/A |
| Subject 2 | ++ | +++ | 1-15 | >30 | acceptable | unacceptable | N/A | N/A |
| Subject 3 | ++ | +++ | >30 | >30 | acceptable | unacceptable | N/A | N/A |
| Subject 4 | ++ | +++ | 1-15 | >30 | acceptable | unacceptable | N/A | N/A |
| Subject 5 | +++ | +++ | 1-15 | >30 | acceptable | unacceptable | N/A | N/A |

Example 5: Vortioxetine Hemihydrobromide:Eudragit E PO=1:1.5 Mixture Preparation 5.00 g of vortioxetine hemihydrobromide that had passed through a 200-mesh stainless steel sieve and 7.50 g of Eudragit E PO were placed in a clean and dry 50 ml screw-top glass reagent bottle. The mixture was mixed with Vortex-2 vortex mixer for 5 minutes. After passing through a 100-mesh stainless steel sieve, the mixture was continued to mix with Vortex-2 vortex mixer for 5 minutes. 0.50 g of the sample was took out for testing. The remaining materials were collected and piled up in a 75 mm diameter stainless steel tray, and the stainless steel tray was placed in DHG-9070A hot air circulating oven at 120-130° C. After heating for 30 minutes, the material became a semi-fluid state. After it was taken out and left to cool, it was milled through a 100-mesh stainless steel sieve with a BJ-300A multifunctional pulverizer several times to obtain a 1:1.5 mixture powder.

The 1:1.5 mixture powder equivalent to 20 mg of vortioxetine and the 100-mesh powder of vortioxetine hemihydrobromide equivalent to 20 mg vortioxetine were tasted and compared by 5 subjects. The irritation of mixture powder was ameliorated significantly.

Self-made sample: Instantaneous irritation +, disappeared within 1-15 minutes after delayed irritation, and the bitterness was acceptable.

Reference sample: Instantaneous irritation ++, disappear after more than 30 minutes after delayed irritation, and the bitterness was unacceptable.

Detailed Information is Listed in Table 16:

TABLE 16

Comparison test of taste of vortioxetine hemihydrobromide solid dispersion

| | Instantaneous irritation | | Delayed irritation (min) | | Bitterness | | Grittiness | |
|---|---|---|---|---|---|---|---|---|
| Subject | Self-made sample | Reference sample | Self-made sample | Reference sample | Self-made sample | Reference sample | Self-made sample | Reference sample |
| Subject 1 | + | +++ | 1-15 | 15-30 | acceptable | unacceptable | N/A | N/A |
| Subject 2 | + | +++ | 1-15 | >30 | acceptable | unacceptable | N/A | N/A |
| Subject 3 | + | ++ | 1-15 | 15-30 | acceptable | unacceptable | N/A | N/A |
| Subject 4 | ++ | +++ | 1-15 | >30 | acceptable | unacceptable | N/A | N/A |
| Subject 5 | + | +++ | 1-15 | 15-30 | acceptable | unacceptable | N/A | N/A |

The UV scan showed that the maximum absorption wavelength and peak intensity of the treated material vortioxetine did not change significantly. The results are shown in FIG. 9, FIG. 12, FIG. 13 and FIG. 14.

Example 6: Vortioxetine Hemihydrobromide:Eudragit E PO=1:5 Mixture Preparation 5.00 g of vortioxetine hemihydrobromide that had passed through a 200-mesh stainless steel sieve and 25.00 g of Eudragit E PO were placed in a clean and dry 100 ml screw-top glass reagent bottle. The mixture was mixed with Vortex-2 vortex mixer for 5 minutes. After passing through a 100-mesh stainless steel sieve, the mixture was continued to mix with Vortex-2 vortex mixer for 5 minutes. 0.50 g of the sample was took out for testing. The remaining materials were collected and piled up in a 75 mm diameter stainless steel tray, and the stainless steel tray was placed in DHG-9070A hot air circulating oven at 120-130° C. After heating for 30 minutes, the material became a semi-fluid state. After it was taken out and left to cool, it was milled through a 100-mesh stainless steel sieve with a BJ-300A multifunctional pulverizer several times to obtain a 1:5 mixture powder with assay (calculated as vortioxetine) 14.39%.

The 1:5 mixture powder equivalent to 20 mg of vortioxetine and the 100-mesh powder of vortioxetine hemihydrobromide equivalent to 20 mg vortioxetine were tasted and compared by 5 subjects. The irritation of mixture powder was ameliorated significantly.

Self-made sample: Instantaneous irritation +, disappeared within 1-15 minutes after delayed irritation, and the bitterness was acceptable.

Reference sample: Instantaneous irritation ++, disappear after more than 30 minutes after delayed irritation, and the bitterness was unacceptable.

Detailed Information is Listed in Table 17:

TABLE 17

Comparison test of taste of vortioxetine hemihydrobromide solid dispersion

| | Instantaneous irritation | | Delayed irritation (min) | | Bitterness | | Grittiness | |
|---|---|---|---|---|---|---|---|---|
| Subject | Self-made sample | Reference sample | Self-made sample | Reference sample | Self-made sample | Reference sample | Self-made sample | Reference sample |
| Subject 1 | + | +++ | 1-15 | 15-30 | acceptable | unacceptable | N/A | N/A |
| Subject 2 | + | +++ | 1-15 | >30 | acceptable | unacceptable | N/A | N/A |
| Subject 3 | + | ++ | 1-15 | 15-30 | acceptable | unacceptable | N/A | N/A |
| Subject 4 | + | +++ | 1-15 | 15-30 | acceptable | unacceptable | N/A | N/A |
| Subject 5 | + | ++ | 1-15 | >30 | acceptable | unacceptable | N/A | N/A |

The UV scan showed that the maximum absorption wavelength and peak intensity of the treated material vortioxetine did not change significantly. The results are shown in FIG. 9, FIG. 12, FIG. 15 and FIG. 16.

Example 7: Vortioxetine Hydrobromide:Polyacrylic Resin IV=1:1.5 Mixture Preparation 7a) Vortioxetine Hemihydrobromide:Polyacrylic Resin IV=1:1.5 Mixture Preparation 5.00 g of vortioxetine hemihydrobromide that had passed through a 200-mesh stainless steel sieve and 7.50 g of Polyacrylic resin IV that had passed through a 100-mesh stainless steel sieve were placed in a clean and dry 100 ml screw-top glass reagent bottle. The mixture was mixed with Vortex-2 vortex mixer for 5 minutes. After passing through a 100-mesh stainless steel sieve, the mixture was continued to mix with Vortex-2 vortex mixer for 5 minutes. 0.50 g of the sample was took out for testing. The remaining materials were collected and piled up in a 75 mm diameter stainless steel tray, and the stainless steel tray was placed in DHG-9070A hot air circulating oven at 120-130° C. After heating for 30 minutes, the material became a semi-fluid state. After it was taken out and left to cool, it was milled through a 100-mesh stainless steel sieve with a BJ-300A multifunctional pulverizer several times to obtain 10.98 g of 1:1.5 mixture powder with yield 87.84% and assay (calculated as vortioxetine) 35.71%.

The 1:1.5 mixture powder equivalent to 20 mg of vortioxetine and the 100-mesh powder of vortioxetine hemihydrobromide equivalent to 20 mg vortioxetine were tasted and compared by 5 subjects. The irritation of mixture powder was ameliorated significantly.

Self-made sample: Instantaneous irritation ++, disappeared within 1-15 minutes after delayed irritation, and the bitterness was acceptable.

Reference sample: Instantaneous irritation +++, disappear after more than 30 minutes after delayed irritation, and the bitterness was unacceptable.

Detailed Information is Listed in Table 18:

TABLE 18

Comparison test of taste of vortioxetine hemihydrobromide solid dispersion

| | Instantaneous irritation | | Delayed irritation (min) | | Bitterness | | Grittiness | |
|---|---|---|---|---|---|---|---|---|
| Subject | Self-made sample | Reference sample | Self-made sample | Reference sample | Self-made sample | Reference sample | Self-made sample | Reference sample |
| Subject 1 | + | +++ | 1-15 | >30 | acceptable | unacceptable | N/A | N/A |
| Subject 2 | ++ | +++ | 1-15 | 15-30 | acceptable | unacceptable | N/A | N/A |
| Subject 3 | + | ++ | 1-15 | 15-30 | acceptable | unacceptable | N/A | N/A |
| Subject 4 | + | +++ | 1-15 | >30 | acceptable | unacceptable | N/A | N/A |
| Subject 5 | + | ++ | 1-15 | >30 | acceptable | unacceptable | N/A | N/A |

7b) Vortioxetine Hydrobromide:Polyacrylic Resin IV=1:1.5 Mixture Preparation 5.00 g of vortioxetine hydrobromide that had passed through a 200-mesh stainless steel sieve and 7.50 g of Polyacrylic resin IV that had passed through a 100-mesh stainless steel sieve were placed in a clean and dry 100 ml screw-top glass reagent bottle. The mixture was mixed with Vortex-2 vortex mixer for 5 minutes. After passing through a 100-mesh stainless steel sieve, the mixture was continued to mix with Vortex-2 vortex mixer for 5 minutes. 0.50 g of the sample was took out for testing. The remaining materials were collected and piled up in a 75 mm diameter stainless steel tray, and the stainless steel tray was placed in DHG-9070A hot air circulating oven at 120-130° C. After heating for 30 minutes, the material became a semi-fluid state. After it was taken out and left to cool, it was milled through a 100-mesh stainless steel sieve with a BJ-300A multifunctional pulverizer several times to obtain 11.23 g of 1:1.5 mixture powder with yield 89.84% and assay (calculated as vortioxetine) 31.12%.

The 1:1.5 mixture powder equivalent to 20 mg of vortioxetine and the 100-mesh powder of vortioxetine hydrobromide equivalent to 20 mg vortioxetine were tasted and compared by 5 subjects. The irritation of mixture powder was ameliorated significantly.

Self-made sample: Instantaneous irritation ++, disappeared within 1-15 minutes after delayed irritation, and the bitterness was acceptable.

Reference sample: Instantaneous irritation +++, disappear after more than 30 minutes after delayed irritation, and the bitterness was unacceptable.

Detailed Information is Listed in Table 19:

TABLE 19

Comparison test of taste of vortioxetine hydrobromide solid dispersion

| | Instantaneous irritation | | Delayed irritation (min) | | Bitterness | | Grittiness | |
|---|---|---|---|---|---|---|---|---|
| Subject | Self-made sample | Reference sample | Self-made sample | Reference sample | Self-made sample | Reference sample | Self-made sample | Reference sample |
| Subject 1 | + | +++ | 1-15 | >30 | acceptable | unacceptable | N/A | N/A |
| Subject 2 | ++ | +++ | 1-15 | >30 | acceptable | unacceptable | N/A | N/A |
| Subject 3 | + | ++ | 1-15 | >30 | acceptable | unacceptable | N/A | N/A |
| Subject 4 | ++ | +++ | 1-15 | >30 | acceptable | unacceptable | N/A | N/A |
| Subject 5 | ++ | ++ | 1-15 | >30 | acceptable | unacceptable | N/A | N/A |

The UV scan showed that the maximum absorption wavelength and peak intensity of the treated material vortioxetine did not change significantly. The results are shown in FIG. 8, FIG. 17, FIG. 18 and FIG. 19.

Example 8: Vortioxetine Hemihydrobromide:Polyacrylic Resin=1:0.3 Solid Dispersion Preparation 8a) Vortioxetine Hemihydrobromide:Polyacrylic Resin IV=1:0.3 Solid Dispersion Preparation 10.00 g of vortioxetine hemihydrobromide, 3.00 g of polyacrylic resin IV and 0.70 g of PEG 4000 were added to 300.00 g of medicinal ethanol, stirred to dissolve, set aside.

The BWF-1G multifunctional fluid bed was installed according to the top spray granulation mode, and the air volume was set 33 $m^3$, the inlet temperature was 50-55° C., the peristaltic pump speed was 8 rpm and the atomization pressure was 1.0-1.5 atm. The above prepared solution was sprayed into the fluid bed, the material status was observed at any time, and the parameters were adjusted appropriately to ensure normal atomization and drying. After spraying, the materials were continued to fluidize for 30 minutes, then stopped heating, and waited until the temperature of the materials was cooled to room temperature. The materials were collected, and the powder with particle size less than 80 mesh was collected by grinding and sieving. 10.29 g of material powder with yield 75.11% was obtained. The assay (calculated as vortioxetine) of powder was 62.97%.

The solid dispersion equivalent to 20 mg of vortioxetine and the 100-mesh powder of vortioxetine hemihydrobromide equivalent to 20 mg vortioxetine were tasted and compared by 5 subjects. The irritation of the untreated material was obvious and could hardly be tolerated, while, the irritation of treated vortioxetine solid dispersion was mild and could be tolerated.

Self-made sample: Instantaneous irritation +, disappeared within 1-15 minutes after delayed irritation, and the bitterness was acceptable.

Reference sample: Instantaneous irritation ++, disappear after more than 30 minutes after delayed irritation, and the bitterness was unacceptable.

Detailed Information is Listed in Table 20:

TABLE 20

| Comparison test of taste of vortioxetine hemihydrobromide taste masking powder | | | | | | | | |
|---|---|---|---|---|---|---|---|---|
| | Instantaneous irritation | | Delayed irritation (min) | | Bitterness | | Grittiness | |
| Subject | Self-made sample | Reference sample | Self-made sample | Reference sample | Self-made sample | Reference sample | Self-made sample | Reference sample |
| Subject 1 | + | +++ | 1-15 | 15-30 | acceptable | unacceptable | N/A | N/A |
| Subject 2 | ++ | ++ | 1-15 | 15-30 | acceptable | unacceptable | N/A | N/A |
| Subject 3 | + | ++ | 1-15 | >30 | acceptable | unacceptable | N/A | N/A |
| Subject 4 | ++ | +++ | 1-15 | >30 | acceptable | unacceptable | N/A | N/A |
| Subject 5 | + | ++ | 1-15 | 15-30 | acceptable | unacceptable | N/A | N/A |

8b) Vortioxetine Hemihydrobromide:Polyacrylic Resin 11=1:0.3 Solid Dispersion Preparation 10.00 g of vortioxetine hemihydrobromide and 3.00 g of polyacrylic resin II were added to 300.00 g of medicinal ethanol, stirred to dissolve, set aside.

The BWF-1G multifunctional fluid bed was installed according to the top spray granulation mode, and the air volume was set 33 $m^3$, the inlet temperature was 50-55° C., the peristaltic pump speed was 8 rpm and the atomization pressure was 1.0-1.5 atm. The above prepared solution was sprayed into the fluid bed, the material status was observed at any time, and the parameters were adjusted appropriately to ensure normal atomization and drying. After spraying, the materials were continued to fluidize for 30 minutes, then stopped heating, and waited until the temperature of the materials was cooled to room temperature. The materials were collected, and the powder with particle size less than 80 mesh was collected by grinding and sieving.

The solid dispersion equivalent to 20 mg of vortioxetine and the 100-mesh powder of vortioxetine hemihydrobromide equivalent to 20 mg vortioxetine were tasted and compared by 5 subjects. The irritation of the untreated material was obvious and could hardly be tolerated, while, the irritation of treated vortioxetine solid dispersion was mild and could be tolerated.

Self-made sample: Instantaneous irritation +, disappeared within 1-15 minutes after delayed irritation, and the bitterness was acceptable.

Reference sample: Instantaneous irritation ++, disappear after more than 30 minutes after delayed irritation, and the bitterness was unacceptable.

Detailed Information is Listed in Table 21:

TABLE 21

| Comparison test of taste of vortioxetine hemihydrobromide taste masking powder | | | | | | | | |
|---|---|---|---|---|---|---|---|---|
| | Instantaneous irritation | | Delayed irritation (min) | | Bitterness | | Grittiness | |
| Subject | Self-made sample | Reference sample | Self-made sample | Reference sample | Self-made sample | Reference sample | Self-made sample | Reference sample |
| Subject 1 | + | +++ | 1-15 | 15-30 | acceptable | unacceptable | N/A | N/A |
| Subject 2 | + | ++ | 1-15 | 15-30 | acceptable | unacceptable | N/A | N/A |
| Subject 3 | ++ | ++ | 1-15 | >30 | acceptable | unacceptable | N/A | N/A |
| Subject 4 | + | +++ | 1-15 | >30 | acceptable | unacceptable | N/A | N/A |
| Subject 5 | ++ | ++ | 1-15 | 15-30 | acceptable | unacceptable | N/A | N/A |

Example 9: Vortioxetine Hemihydrobromide:Taste Masking Excipient=1:0.7 Solid Dispersion Preparation 9a) Vortioxetine Hemihydrobromide:Polyacrylic Resin IV=1:0.7 Solid Dispersion Preparation 10.00 g of vortioxetine hemihydrobromide, 7.70 g of polyacrylic resin IV (Eudragit E100 or Eudragit E PO—purchased from supplier Evonik Rohm GmbH Company, or Urelease E or Urelease E100—purchased from supplier Guangzhou Maofeng Pharmaceutical Excipients Co., Ltd., or Polyacrylic resin IV (trade name)—purchased from Anhui Shanhe Pharmaceutical Excipients Co., Ltd.) were added to 170.00 g of medicinal ethanol, heated to 50-55° C., stirred to dissolve, set aside at 50-55° C.

The BWF-1G multifunctional fluid bed was installed according to the top spray granulation mode, and the air volume was set 33 $m^3$, the inlet temperature was 50-55° C., the peristaltic pump speed was 8 rpm and the atomization pressure was 1.0-1.5 atm. The above prepared solution was sprayed into the fluid bed, the material status was observed at any time, and the parameters were adjusted appropriately to ensure normal atomization and drying. After spraying, the materials were continued to fluidize for 30 minutes, then stopped heating, and waited until the temperature of the materials was cooled to room temperature. The materials were collected, and the powder with particle size less than 80 mesh was collected by sieving. 12.69 g of material powder with yield 71.69% was obtained. The assay (calculated as vortioxetine) of powder was 49.47%.

The solid dispersion equivalent to 20 mg of vortioxetine and the 100-mesh powder of vortioxetine hemihydrobromide equivalent to 20 mg vortioxetine were tasted and compared by 5 subjects. The irritation of the untreated material was obvious and could hardly be tolerated, while, the treated vortioxetine solid dispersion was almost non-irritation.

Self-made sample: Instantaneous irritation ++, disappeared within 1-15 minutes after delayed irritation, and the bitterness was acceptable.

Reference sample: Instantaneous irritation +++, disappear after more than 30 minutes after delayed irritation, and the bitterness was unacceptable.

Detailed Information is Listed in Table 22:

TABLE 22

Comparison test of taste of vortioxetine hemihydrobromide solid dispersion

| Subject | Instantaneous irritation Self-made sample | Instantaneous irritation Reference sample | Delayed irritation (min) Self-made sample | Delayed irritation (min) Reference sample | Bitterness Self-made sample | Bitterness Reference sample | Grittiness Self-made sample | Grittiness Reference sample |
|---|---|---|---|---|---|---|---|---|
| Subject 1 | + | +++ | 1-15 | >30 | acceptable | unacceptable | N/A | N/A |
| Subject 2 | + | ++ | 1-15 | 15-30 | acceptable | unacceptable | N/A | N/A |
| Subject 3 | + | ++ | 1-15 | >30 | acceptable | unacceptable | N/A | N/A |
| Subject 4 | + | +++ | 1-15 | >30 | acceptable | unacceptable | N/A | N/A |
| Subject 5 | + | +++ | 1-15 | 15-30 | acceptable | unacceptable | N/A | N/A |

Figure 20:
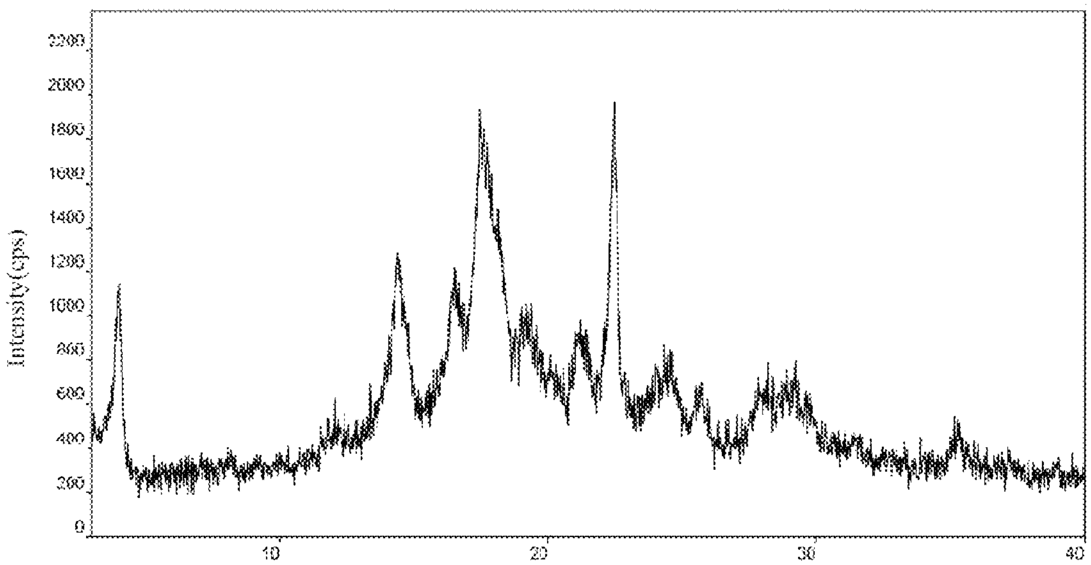
FIG. 20: X-ray powder diffraction pattern of solid dispersion of vortioxetine hemihydrobromide-polyacrylic resin IV.
Figure 21:
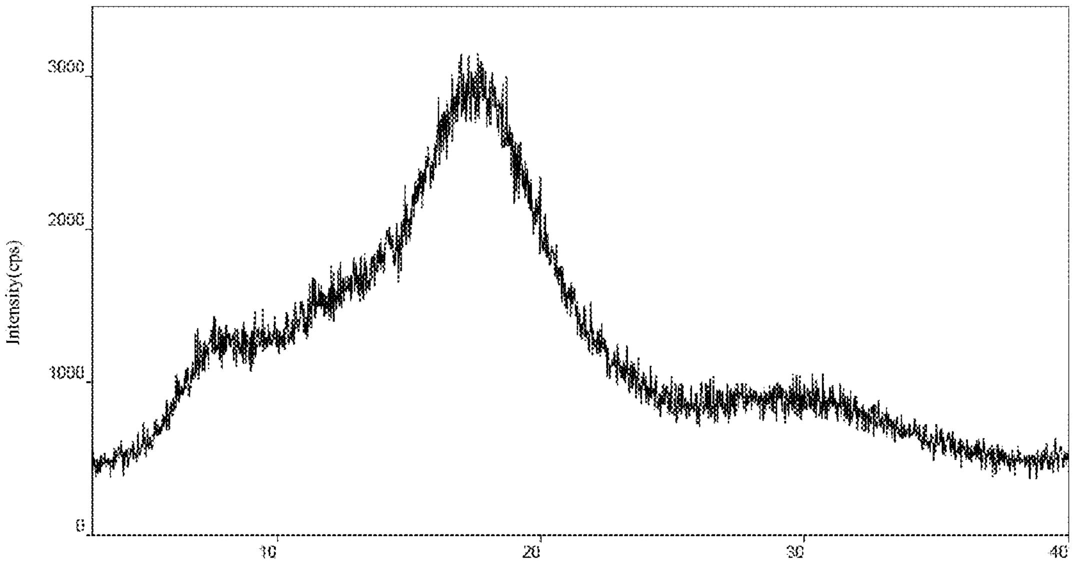
FIG. 21: X-ray powder diffraction pattern of polyacrylic resin IV after spray drying.

The X-ray powder diffraction pattern of the solid dispersion of vortioxetine hemihydrobromide:polyacrylic resin IV=1:0.7 is shown in FIG. 20, and the X-ray powder diffraction pattern of polyacrylic resin IV after spray drying is shown in FIG. 21.

The solid dispersion in Example 9a) was tested for stability according to the requirements of the 2015 Edition of the Pharmacopoeia of the People's Republic of China (accelerated for 6 months, 40±2° C., humidity 75%±5%), and the stability was good. The dissolution rate of the solid dispersion in Example 9a) in 0.1N hydrochloric acid and pH 4.5 acetate buffer (paddle method, 50 revolutions/min) dissolution speed (10 minutes data) was fast with complete dissolution (30 minutes), the results are shown in Table 23.

TABLE 23

Stability Test Table of Vortioxetine hemihydrobromide

| Time | Identification Free base | Identification Br | Test: Dissolution rate in 0.1N HCl (%) 10 minutes | Test: Dissolution rate in pH 4.5 acetate buffer (%) 10 minutes | Test: Dissolution rate in pH 4.5 acetate buffer (%) 30 minutes | Max single impurity (%) |
|---|---|---|---|---|---|---|
| Initial | + | + | 95 | 94 | 98 | 0.11 |
| 6 months | + | + | 96 | 97 | 99 | 0.12 |

9b) Vortioxetine Hydrobromide:Polyacrylic Resin IV=1:0.77 Solid Dispersion Preparation 10.00 g of vortioxetine hydrobromide, 7.70 g of polyacrylic resin IV (Eudragit E100 or Eudragit E PO—purchased from supplier Rohm Company, or Urelease E or Urelease E100—purchased from supplier Guangzhou Maofeng Pharmaceutical Excipients Co., Ltd., or Polyacrylic resin IV (trade name)—purchased from Anhui Shanhe Pharmaceutical Excipients Co., Ltd.) were added to 300.00 g of medicinal ethanol, stirred to dissolve, set aside.

The BWF-1G multifunctional fluid bed was installed according to the top spray granulation mode, and the air volume was set 33 $m^3$, the inlet temperature was 50-55° C., the peristaltic pump speed was 8 rpm and the atomization pressure was 1.0-1.5 atm. The above prepared solution was sprayed into the fluid bed, the material status was observed at any time, and the parameters were adjusted appropriately to ensure normal atomization and drying. After spraying, the materials were continued to fluidize for 30 minutes, then stopped heating, and waited until the temperature of the materials was cooled to room temperature. The materials were collected, and the powder with particle size less than 80 mesh was collected by grinding and sieving. 11.73 g of material powder with yield 66.27% was obtained. The assay (calculated as vortioxetine) of powder was 44.47%, and the assay (calculated as vortioxetine hydrobromide) of powder was 11.83%.

The solid dispersion equivalent to 20 mg of vortioxetine and the 100-mesh powder of vortioxetine hydrobromide equivalent to 20 mg vortioxetine were tasted and compared by 5 subjects. The irritation of the untreated material was obvious and could hardly be tolerated, while, the treated vortioxetine solid dispersion was slightly irritation.

Self-made sample: Instantaneous irritation ++, disappeared within 1-15 minutes after delayed irritation, and the bitterness was acceptable.

Reference sample: Instantaneous irritation +++, disappear after more than 30 minutes after delayed irritation, and the bitterness was unacceptable.

Detailed Information is Listed in Table 24:

TABLE 24

Comparison test of taste of vortioxetine hydrobromide solid dispersion

| | Instantaneous irritation | | Delayed irritation (min) | | Bitterness | | Grittiness | |
|---|---|---|---|---|---|---|---|---|
| Subject | Self-made sample | Reference sample | Self-made sample | Reference sample | Self-made sample | Reference sample | Self-made sample | Reference sample |
| Subject 1 | + | +++ | 1-15 | >30 | acceptable | unacceptable | N/A | N/A |
| Subject 2 | + | +++ | 1-15 | >30 | acceptable | unacceptable | N/A | N/A |
| Subject 3 | + | +++ | 1-15 | >30 | acceptable | unacceptable | N/A | N/A |
| Subject 4 | + | +++ | 1-15 | >30 | acceptable | unacceptable | N/A | N/A |
| Subject 5 | ++ | +++ | 1-15 | >30 | acceptable | unacceptable | N/A | N/A |

Figure 22:
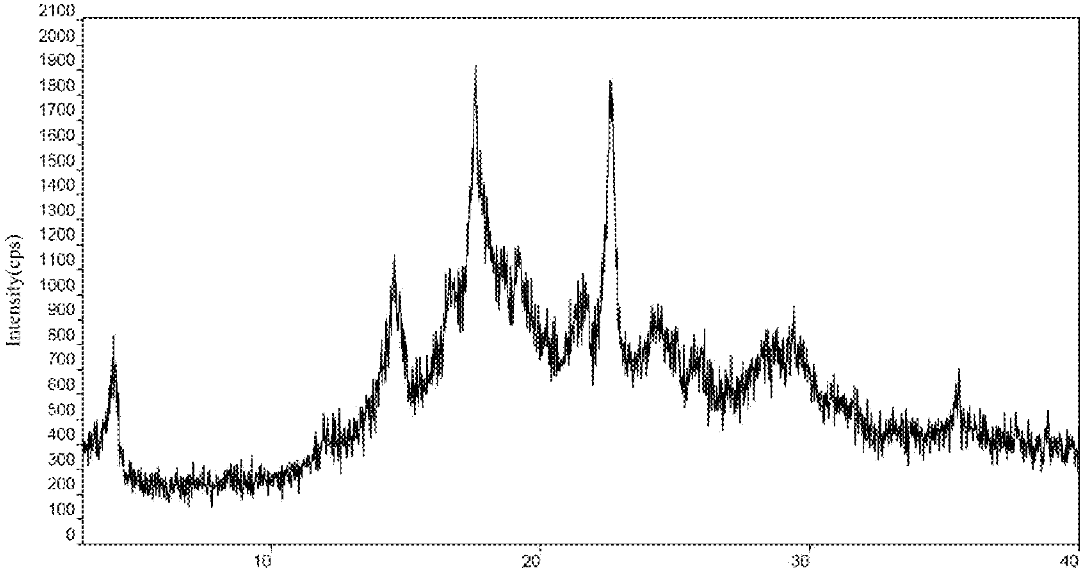
FIG. 22: X-ray powder diffraction pattern of solid dispersion of vortioxetine hydrobromide-polyacrylic resin IV.

The X-ray powder diffraction pattern of the solid dispersion of vortioxetine hydrobromide:polyacrylic resin IV=1:0.77 is shown in FIG. 22, and the X-ray powder diffraction pattern of polyacrylic resin IV after spray drying is shown in FIG. 21.

The solid dispersion in Example 9b) was tested for stability according to the requirements of the 2015 Edition of the Pharmacopoeia of the People's Republic of China (accelerated for 6 months, 40±2° C., humidity 75%±5%), and the stability was good. The dissolution rate of the solid dispersion in Example 9b) in 0.1N hydrochloric acid and pH 4.5 acetate buffer (paddle method, 50 revolutions/min) dissolution speed (10 minutes data) was fast with complete dissolution (30 minutes), the results are shown in Table 25.

TABLE 25

Stability Test Table of Vortioxetine Hydrobromide

| | Identification | | Test: Dissolution rate in 0.1N HCl (%) | Test: Dissolution rate in pH 4.5 acetate buffer (%) | | Max single impurity |
|---|---|---|---|---|---|---|
| Time | Free base | Br | 10 minutes | 10 minutes | 30 minutes | (%) |
| Initial | + | + | 95 | 93 | 97 | 0.10 |
| 6 months | + | + | 96 | 95 | 99 | 0.11 |

9c) Vortioxetine Hemihydrobromide:Eudragit RL100:PEG 6000=1:0.7:0.07 Solid Dispersion Preparation 10.00 g of vortioxetine hemihydrobromide, 7.00 g of Eudragit RL100 and 0.70 g of PEG 6000 were added to 300.00 g of medicinal ethanol, stirred to dissolve, set aside.

The BWF-1G multifunctional fluid bed was installed according to the top spray granulation mode, and the air volume was set 33 $m^3$, the inlet temperature was 50-55° C., the peristaltic pump speed was 8 rpm and the atomization pressure was 1.0-1.5 atm. The above prepared solution was sprayed into the fluid bed, the material status was observed at any time, and the parameters were adjusted appropriately to ensure normal atomization and drying. After spraying, the materials were continued to fluidize for 30 minutes, then stopped heating, and waited until the temperature of the materials was cooled to room temperature. The materials were collected, and the powder with particle size less than 80 mesh was collected by sieving.

The solid dispersion equivalent to 20 mg of vortioxetine and the 100-mesh powder of vortioxetine hemihydrobromide equivalent to 20 mg vortioxetine were tasted and compared by 5 subjects. The irritation of the untreated material was obvious and could hardly be tolerated, while, the treated vortioxetine solid dispersion was almost non-irritation.

Self-made sample: Instantaneous irritation ++, disappeared within 1-15 minutes after delayed irritation, and the bitterness was acceptable.

Reference sample: Instantaneous irritation +++, disappear after more than 30 minutes after delayed irritation, and the bitterness was unacceptable.

Detailed Information is Listed in Table 26:

TABLE 26

Comparison test of taste of vortioxetine hemihydrobromide solid dispersion

| | Instantaneous irritation | | Delayed irritation (min) | | Bitterness | | Grittiness | |
|---|---|---|---|---|---|---|---|---|
| Subject | Self-made sample | Reference sample | Self-made sample | Reference sample | Self-made sample | Reference sample | Self-made sample | Reference sample |
| Subject 1 | ++ | ++ | 1-15 | >30 | acceptable | unacceptable | N/A | N/A |
| Subject 2 | ++ | +++ | 1-15 | 15-30 | acceptable | unacceptable | N/A | N/A |
| Subject 3 | ++ | ++ | 1-15 | >30 | acceptable | unacceptable | N/A | N/A |
| Subject 4 | ++ | +++ | 1-15 | >30 | acceptable | unacceptable | N/A | N/A |
| Subject 5 | + | +++ | 1-15 | 15-30 | acceptable | unacceptable | N/A | N/A |

9d) Vortioxetine Hemihydrobromide:Eudragit S100=1:0.7 Solid Dispersion Preparation 10.00 g of vortioxetine hemihydrobromide and 7.00 g of Eudragit S100 were added to 300.00 g of medicinal ethanol, stirred to dissolve, set aside.

The BWF-1G multifunctional fluid bed was installed according to the top spray granulation mode, and the air volume was set 33 $m^3$, the inlet temperature was 50-55° C., the peristaltic pump speed was 8 rpm and the atomization pressure was 1.0-1.5 atm. The above prepared solution was sprayed into the fluid bed, the material status was observed at any time, and the parameters were adjusted appropriately to ensure normal atomization and drying. After spraying, the materials were continued to fluidize for 30 minutes, then stopped heating, and waited until the temperature of the materials was cooled to room temperature. The materials were collected, and the powder with particle size less than 80 mesh was collected by grinding and sieving.

The solid dispersion equivalent to 20 mg of vortioxetine and the 100-mesh powder of vortioxetine hemihydrobromide equivalent to 20 mg vortioxetine were tasted and compared by 5 subjects. The irritation of the untreated material was obvious and could hardly be tolerated, while, the treated vortioxetine solid dispersion was almost non-irritation.

Self-made sample: Instantaneous irritation +, disappeared within 1-15 minutes after delayed irritation, and the bitterness was acceptable.

Reference sample: Instantaneous irritation ++, disappear after more than 30 minutes after delayed irritation, and the bitterness was unacceptable.

Detailed Information is Listed in Table 27:

TABLE 27

Comparison test of taste of vortioxetine hemihydrobromide solid dispersion

| Subject | Instantaneous irritation | | Delayed irritation (min) | | Bitterness | | Grittiness | |
|---|---|---|---|---|---|---|---|---|
| | Self-made sample | Reference sample | Self-made sample | Reference sample | Self-made sample | Reference sample | Self-made sample | Reference sample |
| Subject 1 | + | ++ | 1-15 | >30 | acceptable | unacceptable | N/A | N/A |
| Subject 2 | + | +++ | 1-15 | 15-30 | acceptable | unacceptable | N/A | N/A |
| Subject 3 | + | ++ | 1-15 | >30 | acceptable | unacceptable | N/A | N/A |
| Subject 4 | + | +++ | 1-15 | >30 | acceptable | unacceptable | N/A | N/A |
| Subject 5 | ++ | ++ | 1-15 | 15-30 | acceptable | unacceptable | N/A | N/A |

9e) Vortioxetine Hemihydrobromide:Eudragit L100=1:0.7 Solid Dispersion Preparation 10.00 g of vortioxetine hemihydrobromide and 7.00 g of Eudragit L100 were added to 300.00 g of medicinal ethanol, stirred to dissolve, set aside.

The BWF-1G multifunctional fluid bed was installed according to the top spray granulation mode, and the air volume was set 33 $m^3$, the inlet temperature was 50-55° C., the peristaltic pump speed was 8 rpm and the atomization pressure was 1.0-1.5 atm. The above prepared solution was sprayed into the fluid bed, the material status was observed at any time, and the parameters were adjusted appropriately to ensure normal atomization and drying. After spraying, the materials were continued to fluidize for 30 minutes, then stopped heating, and waited until the temperature of the materials was cooled to room temperature. The materials were collected, and the powder with particle size less than 80 mesh was collected by grinding and sieving.

The solid dispersion equivalent to 20 mg of vortioxetine and the 100-mesh powder of vortioxetine hemihydrobromide equivalent to 20 mg vortioxetine were tasted and compared by 5 subjects. The irritation of the untreated material was obvious and could hardly be tolerated, while, the treated vortioxetine solid dispersion was almost non-irritation.

Self-made sample: Instantaneous irritation +, disappeared within 1-15 minutes after delayed irritation, and the bitterness was acceptable.

Reference sample: Instantaneous irritation ++, disappear after more than 30 minutes after delayed irritation, and the bitterness was unacceptable.

Detailed Information is Listed in Table 28:

TABLE 28

Comparison test of taste of vortioxetine hemihydrobromide solid dispersion

| Subject | Instantaneous irritation | | Delayed irritation (min) | | Bitterness | | Grittiness | |
|---|---|---|---|---|---|---|---|---|
| | Self-made sample | Reference sample | Self-made sample | Reference sample | Self-made sample | Reference sample | Self-made sample | Reference sample |
| Subject 1 | ++ | ++ | 1-15 | >30 | acceptable | unacceptable | N/A | N/A |
| Subject 2 | + | +++ | 1-15 | 15-30 | acceptable | unacceptable | N/A | N/A |
| Subject 3 | + | ++ | 1-15 | >30 | acceptable | unacceptable | N/A | N/A |
| Subject 4 | + | +++ | 1-15 | >30 | acceptable | unacceptable | N/A | N/A |
| Subject 5 | + | ++ | 1-15 | 15-30 | acceptable | unacceptable | N/A | N/A |

Example 10: Vortioxetine Hemihydrobromide:Polyacrylic Resin IV=1:1 Solid Dispersion Preparation 10.00 g of vortioxetine hydrobromide, 10.00 g of polyacrylic resin IV and 0.70 g of PEG 6000 were added to 300.00 g of medicinal ethanol, stirred to dissolve, set aside.

The BWF-1G multifunctional fluid bed was installed according to the top spray granulation mode, and the air volume was set 33 $m^3$, the inlet temperature was 50-55° C., the peristaltic pump speed was 8 rpm and the atomization pressure was 1.0-1.5 atm. The above prepared solution was sprayed into the fluid bed, the material status was observed at any time, and the parameters were adjusted appropriately to ensure normal atomization and drying. After spraying, the materials were continued to fluidize for 30 minutes, then stopped heating, and waited until the temperature of the materials was cooled to room temperature. The materials were collected, and the powder with particle size less than 80 mesh was collected by grinding and sieving. 13.31 g of material with yield 64.30% was obtained. The assay (calculated as vortioxetine) of powder was 43.38%.

The solid dispersion equivalent to 20 mg of vortioxetine and the 100-mesh powder of vortioxetine hydrobromide equivalent to 20 mg vortioxetine were tasted and compared by 5 subjects. The irritation of the untreated material was obvious and could hardly be tolerated, while, the treated vortioxetine solid dispersion was slightly irritation.

Self-made sample: Instantaneous irritation +, disappeared within 1-15 minutes after delayed irritation, and the bitterness was acceptable.

Reference sample: Instantaneous irritation ++, disappear after more than 30 minutes after delayed irritation, and the bitterness was unacceptable.

Detailed Information is Listed in Table 29:

TABLE 29

Comparison test of taste of vortioxetine hemihydrobromide solid dispersion

| Subject | Instantaneous irritation | | Delayed irritation (min) | | Bitterness | | Grittiness | |
|---|---|---|---|---|---|---|---|---|
| | Self-made sample | Reference sample | Self-made sample | Reference sample | Self-made sample | Reference sample | Self-made sample | Reference sample |
| Subject 1 | + | ++ | 1-15 | >30 | acceptable | unacceptable | N/A | N/A |
| Subject 2 | + | ++ | 1-15 | 15-30 | acceptable | unacceptable | N/A | N/A |
| Subject 3 | + | ++ | 1-15 | 15-30 | acceptable | unacceptable | N/A | N/A |
| Subject 4 | + | +++ | 1-15 | >30 | acceptable | unacceptable | N/A | N/A |
| Subject 5 | + | ++ | 1-15 | 15-30 | acceptable | unacceptable | N/A | N/A |

Example 11: Vortioxetine Hydrobromide:Taste Masking Excipient=1:1.5 Solid Dispersion Preparation 11a) Vortioxetine Hemihydrobromide:Polyacrylic Resin IV=1:1.5 Solid Dispersion Preparation 10.00 g of vortioxetine hemihydrobromide and 15.00 g of polyacrylic resin IV were added to 300.00 g of medicinal ethanol, stirred to dissolve, set aside.

The BWF-1G multifunctional fluid bed was installed according to the top spray granulation mode, and the air volume was set 33 $m^3$, the inlet temperature was 50-55° C., the peristaltic pump speed was 8 rpm and the atomization pressure was 1.0-1.5 atm. The above prepared solution was sprayed into the fluid bed, the material status was observed at any time, and the parameters were adjusted appropriately to ensure normal atomization and drying. After spraying, the materials were continued to fluidize for 30 minutes, then stopped heating, and waited until the temperature of the materials was cooled to room temperature. The materials were collected, and the powder with particle size less than 80 mesh was collected by grinding and sieving. 18.11 g of material with yield 72.44% was obtained. The assay (calculated as vortioxetine) of powder was 34.47%.

The solid dispersion equivalent to 20 mg of vortioxetine and the 100-mesh powder of vortioxetine hemihydrobromide equivalent to 20 mg vortioxetine were tasted and compared by 5 subjects. The irritation of the untreated material was obvious and could hardly be tolerated, while, the treated vortioxetine solid dispersion was almost non-irritation.

Self-made sample: Instantaneous irritation +, disappeared within 1-15 minutes after delayed irritation, and the bitterness was acceptable.

Reference sample: Instantaneous irritation ++, disappear after more than 30 minutes after delayed irritation, and the bitterness was unacceptable.

Detailed Information is Listed in Table 30:

TABLE 30

Comparison test of taste of vortioxetine hemihydrobromide solid dispersion

| | Instantaneous irritation | | Delayed irritation (min) | | Bitterness | | Grittiness | |
|---|---|---|---|---|---|---|---|---|
| Subject | Self-made sample | Reference sample | Self-made sample | Reference sample | Self-made sample | Reference sample | Self-made sample | Reference sample |
| Subject 1 | + | +++ | 1-15 | >30 | acceptable | unacceptable | N/A | N/A |
| Subject 2 | + | ++ | 1-15 | 15-30 | acceptable | unacceptable | N/A | N/A |
| Subject 3 | + | ++ | 1-15 | 15-30 | acceptable | unacceptable | N/A | N/A |
| Subject 4 | + | +++ | 1-15 | 15-30 | acceptable | unacceptable | N/A | N/A |
| Subject 5 | + | ++ | 1-15 | 15-30 | acceptable | unacceptable | N/A | N/A |

11b) Vortioxetine Hydrobromide:Polyacrylic Resin IV=1:1.5 Solid Dispersion Preparation 10.00 g of vortioxetine hydrobromide, 15.00 g of polyacrylic resin IV and 0.70 g of PEG 6000 were added to 300.00 g of medicinal ethanol, stirred to dissolve, set aside.

The BWF-1G multifunctional fluid bed was installed according to the top spray granulation mode, and the air volume was set 33 $m^3$, the inlet temperature was 50-55° C., the peristaltic pump speed was 8 rpm and the atomization pressure was 1.0-1.5 atm. The above prepared solution was sprayed into the fluid bed, the material status was observed at any time, and the parameters were adjusted appropriately to ensure normal atomization and drying. After spraying, the materials were continued to fluidize for 30 minutes, then stopped heating, and waited until the temperature of the materials was cooled to room temperature. The materials were collected, and the powder with particle size less than 80 mesh was collected by grinding and sieving. 17.17 g of material with yield 66.81% was obtained. The assay (calculated as vortioxetine) of powder was 30.57%.

The solid dispersion equivalent to 20 mg of vortioxetine and the 100-mesh powder of vortioxetine hydrobromide equivalent to 20 mg vortioxetine were tasted and compared by 5 subjects. The irritation of the untreated material was obvious and could hardly be tolerated, while, the treated vortioxetine solid dispersion was almost non-irritation.

Self-made sample: Instantaneous irritation +, disappeared within 1-15 minutes after delayed irritation, and the bitterness was acceptable.

Reference sample: Instantaneous irritation +++, disappear after more than 30 minutes after delayed irritation, and the bitterness was unacceptable.

Detailed Information is Listed in Table 31:

TABLE 31

Comparison test of taste of vortioxetine hydrobromide solid dispersion

| | Instantaneous irritation | | Delayed irritation (min) | | Bitterness | | Grittiness | |
|---|---|---|---|---|---|---|---|---|
| Subject | Self-made sample | Reference sample | Self-made sample | Reference sample | Self-made sample | Reference sample | Self-made sample | Reference sample |
| Subject 1 | + | +++ | 1-15 | >30 | acceptable | unacceptable | N/A | N/A |
| Subject 2 | + | +++ | 1-15 | >30 | acceptable | unacceptable | N/A | N/A |
| Subject 3 | + | +++ | 1-15 | >30 | acceptable | unacceptable | N/A | N/A |
| Subject 4 | + | +++ | 1-15 | >30 | acceptable | unacceptable | N/A | N/A |
| Subject 5 | + | +++ | 1-15 | >30 | acceptable | unacceptable | N/A | N/A |

11c) Vortioxetine Hydrobromide:Ethyl Cellulose N10=1:1.5 Solid Dispersion Preparation 10.00 g of vortioxetine hydrobromide and 15.00 g of ethyl cellulose N10 were added to 300.00 g of medicinal ethanol, stirred to dissolve. then 1.00 g of potassium citrate after passing through 200 mesh sieve was added, stirred to dispersed to prevent sedimentation. set aside.

The BWF-1G multifunctional fluid bed was installed according to the top spray granulation mode, and the air volume was set 33 $m^3$, the inlet temperature was 50-55° C., the peristaltic pump speed was 8 rpm and the atomization pressure was 1.0-1.5 atm. The above prepared solution was sprayed into the fluid bed, the material status was observed at any time, and the parameters were adjusted appropriately to ensure normal atomization and drying. After spraying, the materials were continued to fluidize for 30 minutes, then stopped heating, and waited until the temperature of the materials was cooled to room temperature. The materials were collected, and the powder with particle size less than 80 mesh was collected by grinding and sieving.

The solid dispersion equivalent to 20 mg of vortioxetine and the 100-mesh powder of vortioxetine hydrobromide equivalent to 20 mg vortioxetine were tasted and compared by 5 subjects. The irritation of the untreated material was obvious and could hardly be tolerated, while, the treated vortioxetine solid dispersion was almost non-irritation.

Self-made sample: Instantaneous irritation +, disappeared within 1-15 minutes after delayed irritation, and the bitterness was acceptable.

Reference sample: Instantaneous irritation +++, disappear after more than 30 minutes after delayed irritation, and the bitterness was unacceptable.

Detailed Information is Listed in Table 32:

TABLE 32

Comparison test of taste of vortioxetine hydrobromide solid dispersion

| Subject | Instantaneous irritation | | Delayed irritation (min) | | Bitterness | | Grittiness | |
|---|---|---|---|---|---|---|---|---|
| | Self-made sample | Reference sample | Self-made sample | Reference sample | Self-made sample | Reference sample | Self-made sample | Reference sample |
| Subject 1 | + | +++ | 1-15 | >30 | acceptable | unacceptable | N/A | N/A |
| Subject 2 | + | +++ | 1-15 | >30 | acceptable | unacceptable | N/A | N/A |
| Subject 3 | + | +++ | 1-15 | >30 | acceptable | unacceptable | N/A | N/A |
| Subject 4 | + | +++ | 1-15 | >30 | acceptable | unacceptable | N/A | N/A |
| Subject 5 | + | +++ | 1-15 | >30 | acceptable | unacceptable | N/A | N/A |

Example 12: Vortioxetine Hemihydrobromide:Taste Masking Excipient=1:2 Solid Dispersion Preparation 12a) Vortioxetine Hemihydrobromide:Polyacrylic Resin IV=1:2 Solid Dispersion Preparation 10.00 g of vortioxetine hemihydrobromide, 20.00 g of polyacrylic resin IV and 0.70 g of PEG 6000 were added to 300.00 g of medicinal ethanol, stirred to dissolve, set aside.

The BWF-1G multifunctional fluid bed was installed according to the top spray granulation mode, and the air volume was set 33 $m^3$, the inlet temperature was 50-55° C., the peristaltic pump speed was 8 rpm and the atomization pressure was 1.0-1.5 atm. The above prepared solution was sprayed into the fluid bed, the material status was observed at any time, and the parameters were adjusted appropriately to ensure normal atomization and drying. After spraying, the materials were continued to fluidize for 30 minutes, then stopped heating, and waited until the temperature of the materials was cooled to room temperature. The materials were collected, and the powder with particle size less than 80 mesh was collected by grinding and sieving. 20.20 g of material with yield 65.80% was obtained. The assay (calculated as vortioxetine) of powder was 27.99%.

The solid dispersion equivalent to 20 mg of vortioxetine and the 100-mesh powder of vortioxetine hemihydrobromide equivalent to 20 mg vortioxetine were tasted and compared by 5 subjects. The irritation of the untreated material was obvious and could hardly be tolerated, while, the treated vortioxetine solid dispersion was almost non-irritation.

Self-made sample: Instantaneous irritation +, disappeared within 1-15 minutes after delayed irritation, and the bitterness was acceptable.

Reference sample: Instantaneous irritation +++, disappear after more than 30 minutes after delayed irritation, and the bitterness was unacceptable.

Detailed Information is Listed in Table 33:

12b) Vortioxetine Hemihydrobromide:Cellulose Acetate=1:2 Solid Dispersion Preparation 10.00 g of vortioxetine hemihydrobromide, 20.00 g of cellulose acetate and 0.70 g of PEG 8000 were added to 300.00 g of medicinal ethanol, stirred to dissolve, set aside.

The BWF-1G multifunctional fluid bed was installed according to the top spray granulation mode, and the air volume was set 33 $m^3$, the inlet temperature was 50-55° C., the peristaltic pump speed was 8 rpm and the atomization pressure was 1.0-1.5 atm. The above prepared solution was sprayed into the fluid bed, the material status was observed at any time, and the parameters were adjusted appropriately to ensure normal atomization and drying. After spraying, the materials were continued to fluidize for 30 minutes, then stopped heating, and waited until the temperature of the materials was cooled to room temperature. The materials were collected, and the powder with particle size less than 80 mesh was collected by grinding and sieving.

The solid dispersion equivalent to 20 mg of vortioxetine and the 100-mesh powder of vortioxetine hemihydrobromide equivalent to 20 mg vortioxetine were tasted and compared by 5 subjects. The irritation of the untreated material was obvious and could hardly be tolerated, while, the treated vortioxetine solid dispersion was almost non-irritation.

Self-made sample: Instantaneous irritation +, disappeared within 1-15 minutes after delayed irritation, and the bitterness was acceptable.

Reference sample: Instantaneous irritation +++, disappear after more than 30 minutes after delayed irritation, and the bitterness was unacceptable.

TABLE 33

Comparison test of taste of vortioxetine hemihydrobromide solid dispersion

| Subject | Instantaneous irritation | | Delayed irritation (min) | | Bitterness | | Grittiness | |
|---|---|---|---|---|---|---|---|---|
| | Self-made sample | Reference sample | Self-made sample | Reference sample | Self-made sample | Reference sample | Self-made sample | Reference sample |
| Subject 1 | + | ++ | 1-15 | 15-30 | acceptable | unacceptable | N/A | N/A |
| Subject 2 | + | +++ | 1-15 | >30 | acceptable | unacceptable | N/A | N/A |
| Subject 3 | + | ++ | 1-15 | >30 | acceptable | unacceptable | N/A | N/A |
| Subject 4 | + | ++ | 1-15 | >30 | acceptable | unacceptable | N/A | N/A |
| Subject 5 | + | ++ | 1-15 | 15-30 | acceptable | unacceptable | N/A | N/A |

Detailed Information is Listed in Table 34:

TABLE 34

| Comparison test of taste of vortioxetine hemihydrobromide solid dispersion | | | | | | | | |
|---|---|---|---|---|---|---|---|---|
| | Instantaneous irritation | | Delayed irritation (min) | | Bitterness | | Grittiness | |
| Subject | Self-made sample | Reference sample | Self-made sample | Reference sample | Self-made sample | Reference sample | Self-made sample | Reference sample |
| Subject 1 | + | ++ | 1-15 | 15-30 | acceptable | unacceptable | N/A | N/A |
| Subject 2 | + | +++ | 1-15 | >30 | acceptable | unacceptable | N/A | N/A |
| Subject 3 | + | ++ | 1-15 | >30 | acceptable | unacceptable | N/A | N/A |
| Subject 4 | + | ++ | 1-15 | 15-30 | acceptable | unacceptable | N/A | N/A |
| Subject 5 | + | ++ | 1-15 | >30 | acceptable | unacceptable | N/A | N/A |

Example 13: Vortioxetine Hemihydrobromide+Taste Masking Excipient Solid Dispersion Preparation 13a) Vortioxetine Hemihydrobromide:Polyacrylic Resin IV=1:5 Solid Dispersion Preparation 10.00 g of vortioxetine hemihydrobromide and 50.00 g of polyacrylic resin IV were added to 500.00 g of medicinal ethanol, stirred to dissolve, set aside.

The BWF-1G multifunctional fluid bed was installed according to the top spray granulation mode, and the air volume was set 33 $m^3$, the inlet temperature was 50-55° C., the peristaltic pump speed was 8 rpm and the atomization pressure was 1.0-1.5 atm. The above prepared solution was sprayed into the fluid bed, the material status was observed at any time, and the parameters were adjusted appropriately to ensure normal atomization and drying. After spraying, the materials were continued to fluidize for 30 minutes, then stopped heating, and waited until the temperature of the materials was cooled to room temperature. The materials were collected, and the powder with particle size less than 80 mesh was collected by grinding and sieving. 49.29 g of material with yield 82.15% was obtained. The assay (calculated as vortioxetine) of powder was 14.67%.

The solid dispersion equivalent to 20 mg of vortioxetine and the 100-mesh powder of vortioxetine hemihydrobromide equivalent to 20 mg vortioxetine were tasted and compared by 5 subjects. The irritation of the untreated material was obvious and could hardly be tolerated, while, the treated vortioxetine solid dispersion was almost non-irritation.

Self-made sample: Instantaneous irritation +, disappeared within 1-15 minutes after delayed irritation, and the bitterness was acceptable.

Reference sample: Instantaneous irritation ++, disappear after more than 30 minutes after delayed irritation, and the bitterness was unacceptable.

Detailed Information is Listed in Table 35:

TABLE 35

| Comparison test of taste of vortioxetine hemihydrobromide solid dispersion | | | | | | | | |
|---|---|---|---|---|---|---|---|---|
| | Instantaneous irritation | | Delayed irritation (min) | | Bitterness | | Grittiness | |
| Subject | Self-made sample | Reference sample | Self-made sample | Reference sample | Self-made sample | Reference sample | Self-made sample | Reference sample |
| Subject 1 | + | ++ | 1-15 | 15-30 | acceptable | unacceptable | N/A | N/A |
| Subject 2 | + | +++ | 1-15 | >30 | acceptable | unacceptable | N/A | N/A |
| Subject 3 | + | ++ | 1-15 | 15-30 | acceptable | unacceptable | N/A | N/A |
| Subject 4 | + | +++ | 1-15 | 15-30 | acceptable | unacceptable | N/A | N/A |
| Subject 5 | + | ++ | 1-15 | >30 | acceptable | unacceptable | N/A | N/A |

13b) Vortioxetine Hemihydrobromide:Hydroxypropyl Cellulose LF=1:3 Solid Dispersion Preparation 10.00 g of vortioxetine hemihydrobromide, 30.00 g of hydroxypropyl cellulose LF and 1 g of meglumine were added to 300.00 g of medicinal ethanol, stirred to dissolve, set aside.

The BWF-1G multifunctional fluid bed was installed according to the top spray granulation mode, and the air volume was set 33 $m^3$, the inlet temperature was 50-55° C., the peristaltic pump speed was 8 rpm and the atomization pressure was 1.0-1.5 atm. The above prepared solution was sprayed into the fluid bed, the material status was observed at any time, and the parameters were adjusted appropriately to ensure normal atomization and drying. After spraying, the materials were continued to fluidize for 30 minutes, then stopped heating, and waited until the temperature of the materials was cooled to room temperature. The materials were collected, and the powder with particle size less than 80 mesh was collected by grinding and sieving.

The solid dispersion equivalent to 20 mg of vortioxetine and the 100-mesh powder of vortioxetine hemihydrobromide equivalent to 20 mg vortioxetine were tasted and compared by 5 subjects. The irritation of the untreated material was obvious and could hardly be tolerated, while, the treated vortioxetine solid dispersion was almost non-irritation.

Self-made sample: Instantaneous irritation +, disappeared within 1-15 minutes after delayed irritation, and the bitterness was acceptable.

Reference sample: Instantaneous irritation ++, disappear after more than 30 minutes after delayed irritation, and the bitterness was unacceptable.

Detailed Information is Listed in Table 36:

TABLE 36

| Comparison test of taste of vortioxetine hemihydrobromide solid dispersion | | | | | | | | |
|---|---|---|---|---|---|---|---|---|
| | Instantaneous irritation | | Delayed irritation (min) | | Bitterness | | Grittiness | |
| Subject | Self-made sample | Reference sample | Self-made sample | Reference sample | Self-made sample | Reference sample | Self-made sample | Reference sample |
| Subject 1 | + | ++ | 1-15 | 15-30 | acceptable | unacceptable | N/A | N/A |
| Subject 2 | + | +++ | 1-15 | >30 | acceptable | unacceptable | N/A | N/A |
| Subject 3 | + | ++ | 1-15 | 15-30 | acceptable | unacceptable | N/A | N/A |
| Subject 4 | + | +++ | 1-15 | 15-30 | acceptable | unacceptable | N/A | N/A |
| Subject 5 | + | ++ | 1-15 | >30 | acceptable | unacceptable | N/A | N/A |

Example 14: Vortioxetine Hemihydrobromide+Polyacrylic Resin Solid Dispersion Preparation 14a) Vortioxetine Hemihydrobromide:Polyacrylic Resin 11=1:5 Solid Dispersion Preparation 10.00 g of vortioxetine hemihydrobromide and 50.00 g of polyacrylic resin II were added to 500.00 g of medicinal ethanol, stirred and dissolved in water bath at 40-50° C. water bath, filtered with 0.45 um microporous membrane. In the stirred state, the pH of the filtrate was adjusted with 5% of (g/g) sodium hydroxide solution until there was no more precipitates appear in the material (pH was 8.54 at this time), then ethanol was removed with the vacuum rotary evaporator, and the resulting solid was removed with the vacuum freeze dryer at 40-50° C., then the solid was passed through the 100-mesh stainless steel sieve. 50.54 g of solid dispersion contained vortioxetine with yield 84.23% was obtained. The assay (calculated as vortioxetine) of powder was 14.79%.

The solid dispersion equivalent to 20 mg of vortioxetine and the 100-mesh powder of vortioxetine hemihydrobromide equivalent to 20 mg vortioxetine were tasted and compared by 5 subjects. The unique irritation of vortioxetine was not felt.

Self-made sample: Instantaneous irritation +, disappeared within 1-15 minutes after delayed irritation, and the bitterness was acceptable.

Reference sample: Instantaneous irritation ++, disappear after more than 30 minutes after delayed irritation, and the bitterness was unacceptable.

Detailed Information is Listed in Table 37:

TABLE 37

| Comparison test of taste of vortioxetine hemihydrobromide solid dispersion | | | | | | | | |
|---|---|---|---|---|---|---|---|---|
| | Instantaneous irritation | | Delayed irritation (min) | | Bitterness | | Grittiness | |
| Subject | Self-made sample | Reference sample | Self-made sample | Reference sample | Self-made sample | Reference sample | Self-made sample | Reference sample |
| Subject 1 | + | ++ | 1-15 | 15-30 | acceptable | unacceptable | N/A | N/A |
| Subject 2 | + | +++ | 1-15 | >30 | acceptable | unacceptable | N/A | N/A |
| Subject 3 | + | ++ | 1-15 | >30 | acceptable | unacceptable | N/A | N/A |
| Subject 4 | + | +++ | 1-15 | >30 | acceptable | unacceptable | N/A | N/A |
| Subject 5 | + | ++ | 1-15 | 15-30 | acceptable | unacceptable | N/A | N/A |

14b) Vortioxetine Hydrobromide:Polyacrylic Resin 11=1:1.5 Solid Dispersion Preparation 10.00 g of vortioxetine hydrobromide and 15.00 g of polyacrylic resin II were added to 250.00 g of medicinal ethanol, stirred and dissolved in water bath at 40-50° C. water bath, filtered with 0.45 um microporous membrane. In the stirred state, the pH of the filtrate was adjusted with 5% of (g/g) sodium hydroxide solution until there was no more precipitates appear in the material (pH was 8.32 at this time), then ethanol was removed with the vacuum rotary evaporator, and the resulting solid was removed with the vacuum freeze dryer at 40-50° C., then the solid was passed through the 100-mesh stainless steel sieve. 19.67 g of solid dispersion contained vortioxetine with yield 78.68% was obtained. The assay (calculated as vortioxetine) of powder was 29.97%.

The solid dispersion equivalent to 20 mg of vortioxetine and the 100-mesh powder of vortioxetine hydrobromide equivalent to 20 mg vortioxetine were tasted and compared by 5 subjects. The unique irritation of vortioxetine was not felt.

Self-made sample: Instantaneous irritation +, disappeared within 1-15 minutes after delayed irritation, and the bitterness was acceptable.

Reference sample: Instantaneous irritation +++, disappear after more than 30 minutes after delayed irritation, and the bitterness was unacceptable.

Detailed Information is Listed in Table 38:

TABLE 38

Comparison test of taste of vortioxetine hydrobromide solid dispersion

| | Instantaneous irritation | | Delayed irritation (min) | | Bitterness | | Grittiness | |
|---|---|---|---|---|---|---|---|---|
| Subject | Self-made sample | Reference sample | Self-made sample | Reference sample | Self-made sample | Reference sample | Self-made sample | Reference sample |
| Subject 1 | + | +++ | 1-15 | >30 | acceptable | unacceptable | N/A | N/A |
| Subject 2 | + | +++ | 1-15 | >30 | acceptable | unacceptable | N/A | N/A |
| Subject 3 | ++ | +++ | 1-15 | >30 | acceptable | unacceptable | N/A | N/A |
| Subject 4 | + | +++ | 1-15 | >30 | acceptable | unacceptable | N/A | N/A |
| Subject 5 | + | +++ | 1-15 | >30 | acceptable | unacceptable | N/A | N/A |

Figure 23:
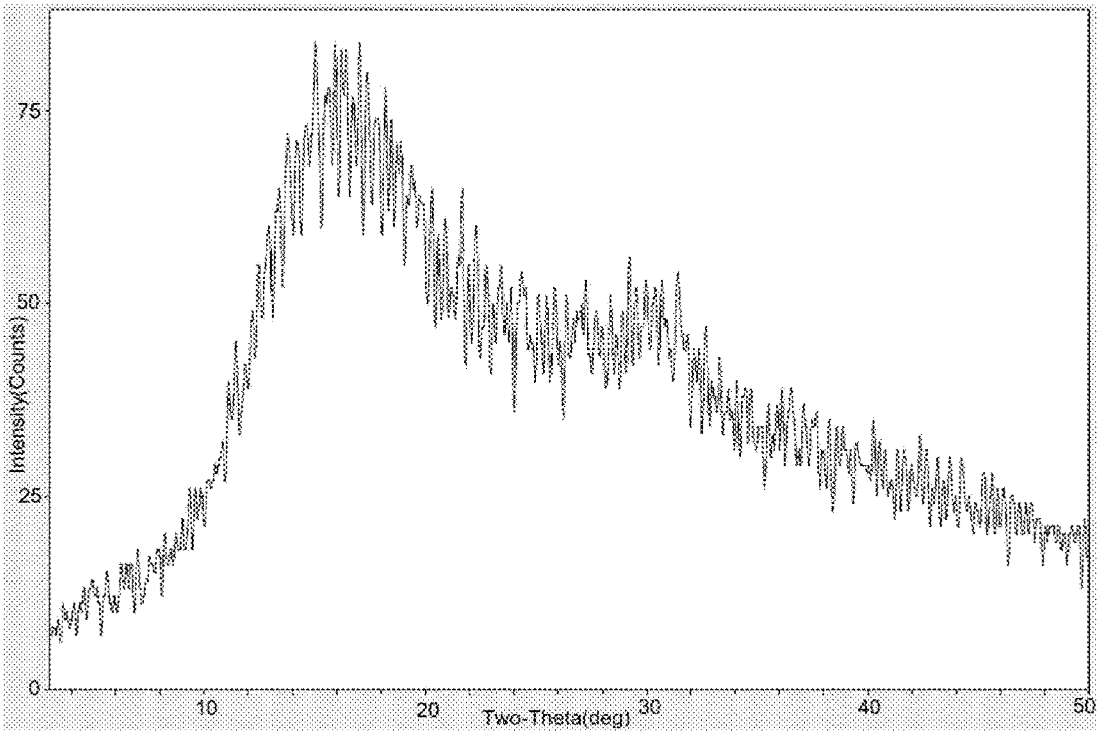
FIG. 23: Vortioxetine hydrobromide:polyacrylic resin II=1:1.5 solid dispersion X-ray powder diffraction pattern.
Figure 24:
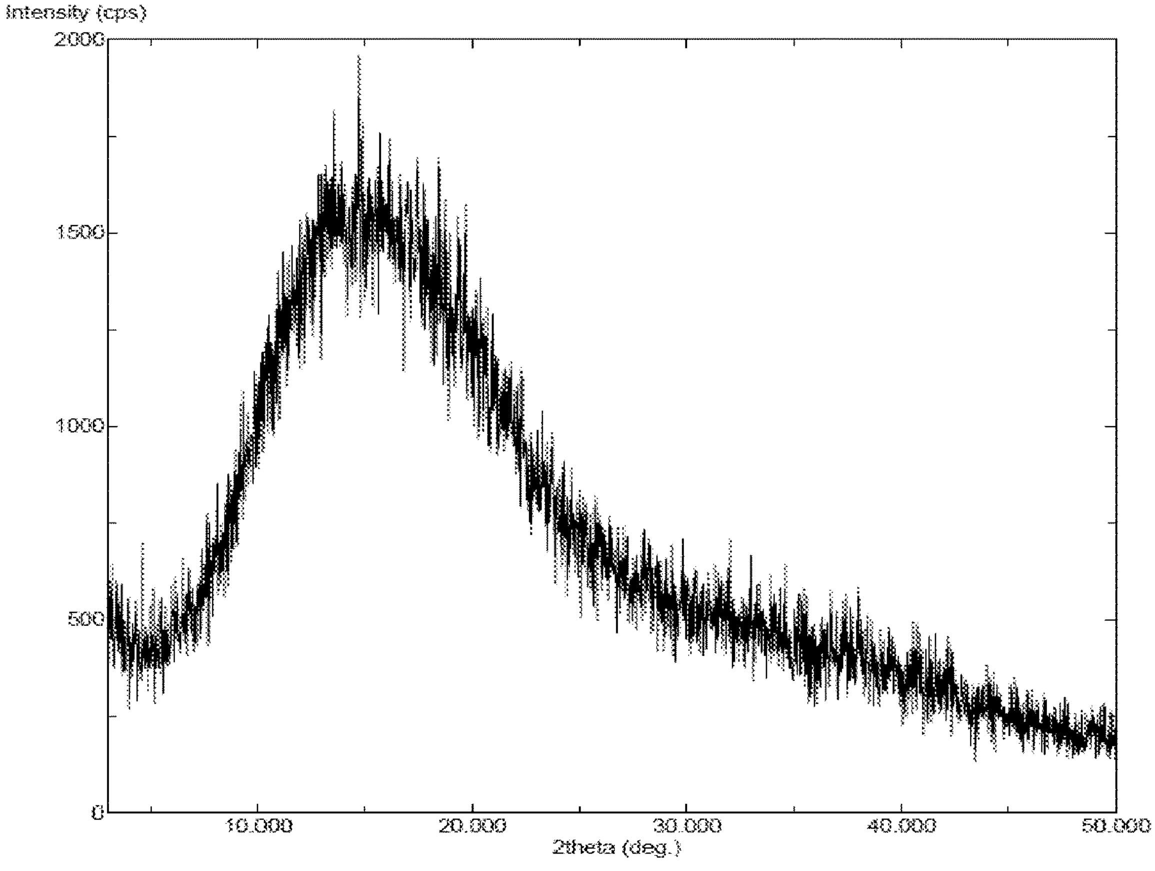
FIG. 24: X-ray powder diffraction pattern of polyacrylic resin II (distilling off the solvent of ethanol).

The X-ray powder diffraction pattern of vortioxetine hydrobromide:polyacrylic resin 11=1:1.5 solid dispersion is shown in FIG. 23, and the X-ray powder diffraction pattern of polyacrylic resin II (ethanol rotary evaporation) is shown in FIG. 24.

Example 15: Vortioxetine Hemihydrobromide:Polyacrylic Resin 11=1:1.5 Solid Dispersion Preparation 10.00 g of vortioxetine hemihydrobromide and 15.00 g of polyacrylic resin II were added to 250.00 g of medicinal ethanol, stirred and dissolved in water bath at 40-50° C. water bath, filtered with 0.45 um microporous membrane. In the stirred state, the pH of the filtrate was adjusted with 5% of (g/g) sodium hydroxide solution until there was no more precipitates appear in the material (pH was 8.47 at this time), then the insoluble matter was separated and added to 400 g of purified water. After homogenizing through a 100-mesh sieve at 40-50° C., it was granulated by BWF-1G multi-functional fluid bed top spraying. Then the obtained powder was passed through the 100-mesh stainless steel sieve. 12.94 g of solid dispersion contained vortioxetine with yield 51.76% was obtained. The assay (calculated as vortioxetine) of powder was 35.77%.

The solid dispersion equivalent to 20 mg of vortioxetine and the 100-mesh powder of vortioxetine hemihydrobromide equivalent to 20 mg vortioxetine were tasted and compared by 5 subjects. The unique irritation of vortioxetine can not be felt.

Self-made sample: Instantaneous irritation +, disappeared within 1-15 minutes after delayed irritation, and the bitterness was acceptable.

Reference sample: Instantaneous irritation ++, disappear after more than 30 minutes after delayed irritation, and the bitterness was unacceptable.

Detailed Information is Listed in Table 39:

TABLE 39

Comparison test of taste of vortioxetine hemihydrobromide solid dispersion

| | Instantaneous irritation | | Delayed irritation (min) | | Bitterness | | Grittiness | |
|---|---|---|---|---|---|---|---|---|
| Subject | Self-made sample | Reference sample | Self-made sample | Reference sample | Self-made sample | Reference sample | Self-made sample | Reference sample |
| Subject 1 | + | ++ | 1-15 | 15-30 | acceptable | unacceptable | N/A | N/A |
| Subject 2 | + | +++ | 1-15 | 15-30 | acceptable | unacceptable | N/A | N/A |
| Subject 3 | + | ++ | 1-15 | >30 | acceptable | unacceptable | N/A | N/A |
| Subject 4 | + | +++ | 1-15 | 1-15 | acceptable | unacceptable | N/A | N/A |
| Subject 5 | + | ++ | 1-15 | >30 | acceptable | unacceptable | N/A | N/A |

Figure 25:
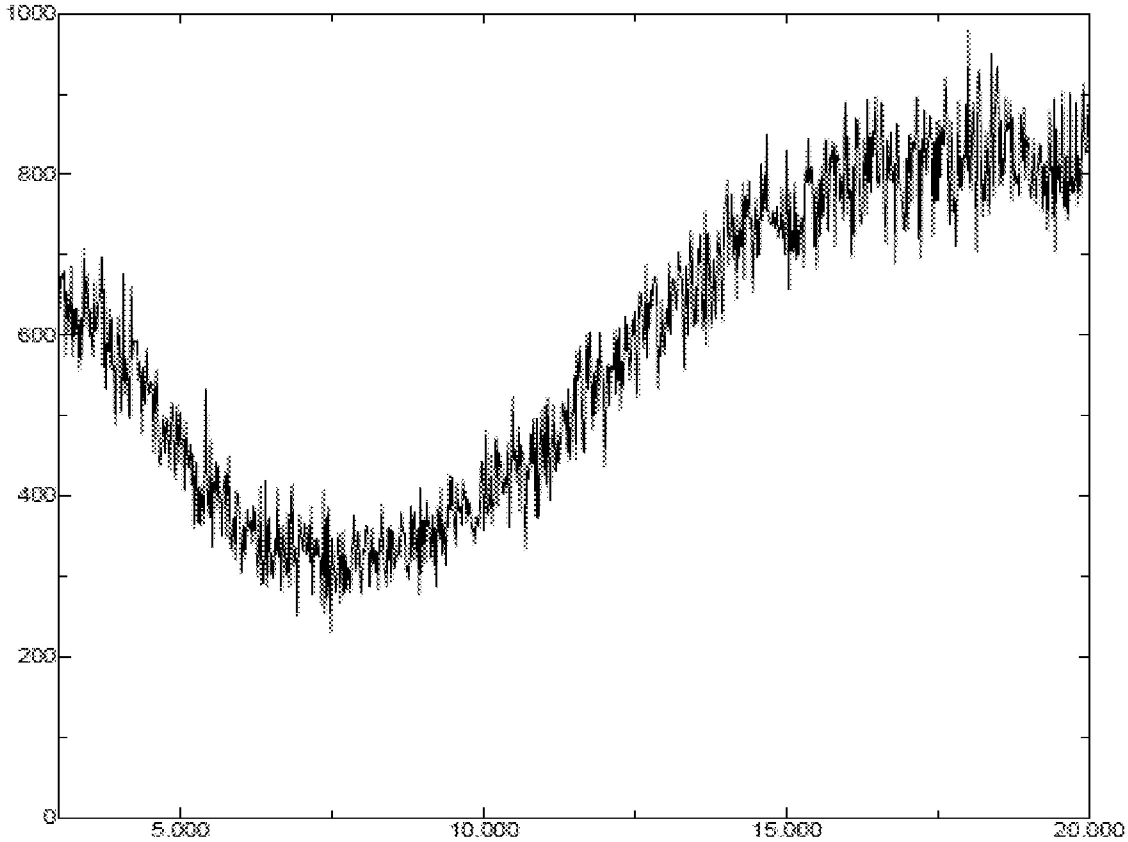
FIG. 25: Vortioxetine hemihydrobromide:polyacrylic resin II=1:1.5 solid dispersion X-ray powder diffraction pattern.

The X-ray powder diffraction pattern of vortioxetine hemihydrobromide:polyacrylic resin 11=1:1.5 solid dispersion is shown in FIG. 25, and the X-ray powder diffraction pattern of polyacrylic resin II (ethanol rotary evaporation) is shown in FIG. 24.

Example 16: Preparation of Taste Masking Granules with Taste Masking Coating Powder 10.00 g of Eudragit RS100 was added to 150.00 g of ethanol, stirred to dissolve, set aside.

10.00 g of powder prepared in Example 1d) was added to the above prepared solution, stirred to dispersed. After sieving through 60 mesh stainless steel screen, the materials were continued stirring to prevent sedimentation.

The BWF-1G multifunctional fluid bed was installed according to the top spray granulation mode, and the air volume was set 33 $m^3$, the inlet temperature was 50-55° C., the peristaltic pump speed was 8 rpm and the atomization pressure was 1.0-1.5 atm. The prepared suspension material was sprayed into the fluid bed, and the material status was observed at any time. After spraying, the materials were continued to fluidize for 30 minutes, then stopped heating, and waited until the temperature of the materials was cooled to room temperature. The materials were collected, and the powder with particle size less than 50 mesh was collected by grinding and sieving. 15.87 g of powder with yield 79.35% was obtained. The assay (calculated as vortioxetine) of powder was 25.47%.

The taste masking granules equivalent to 20 mg of vortioxetine and the 100-mesh powder of vortioxetine hemihydrobromide equivalent to 20 mg vortioxetine were tasted and compared by 5 subjects. The irritation of the untreated material was obvious and could hardly be tolerated, while, the treated vortioxetine granules was slightly irritation and could be tolerated.

Self-made sample: Instantaneous irritation +, disappeared within 1-15 minutes after delayed irritation, and the bitterness was acceptable.

Reference sample: Instantaneous irritation ++, disappear after more than 30 minutes after delayed irritation, and the bitterness was unacceptable.

Detailed Information is Listed in Table 40:

TABLE 40

Comparison test of taste of vortioxetine hemihydrobromide taste masking granules

| Subject | Instantaneous irritation | | Delayed irritation (min) | | Bitterness | | Grittiness | |
|---|---|---|---|---|---|---|---|---|
| | Self-made sample | Reference sample | Self-made sample | Reference sample | Self-made sample | Reference sample | Self-made sample | Reference sample |
| Subject 1 | + | ++ | 1-15 | 15-30 | acceptable | unacceptable | N/A | N/A |
| Subject 2 | + | ++ | 1-15 | 15-30 | acceptable | unacceptable | N/A | N/A |
| Subject 3 | + | +++ | 1-15 | >30 | acceptable | unacceptable | N/A | N/A |
| Subject 4 | + | ++ | 1-15 | >30 | acceptable | unacceptable | N/A | N/A |
| Subject 5 | + | +++ | 1-15 | 15-30 | acceptable | unacceptable | N/A | N/A |

Example 17: Preparation of Taste Masking Powder with Solid Dispersion 5.00 g of chitosan (degree of deacetylation greater than or equal to 85%) was added to 100.00 g of purified water, stirred to dissolve, set aside.

10.00 g of powder prepared in Example 9a) was added to the above prepared solution, stirred to dispersed. After sieving through 60 mesh stainless steel screen, the materials were continued stirring to prevent sedimentation.

The BWF-1G multifunctional fluid bed was installed according to the top spray granulation mode, and the air volume was set 33 $m^3$, the inlet temperature was 60-65° C., the peristaltic pump speed was 8 rpm and the atomization pressure was 1.0-1.5 atm. The prepared suspension material was sprayed into the fluid bed, and the material status was observed at any time. After spraying, the materials were continued to fluidize for 30 minutes, then stopped heating, and waited until the temperature of the materials was cooled to room temperature. The materials were collected, and the powder with particle size less than 60 mesh was collected by grinding and sieving. 11.11 g of powder with yield 74.07% was obtained. The assay (calculated as vortioxetine) of powder was 35.17%.

The taste masking granules equivalent to 20 mg of vortioxetine and the 100-mesh powder of vortioxetine hemihydrobromide equivalent to 20 mg vortioxetine were tasted and compared by 5 subjects, which proved irritation of the untreated material was obvious and could hardly be tolerated, while, the treated vortioxetine powder was slightly irritation and could be tolerated.

Self-made sample: Instantaneous irritation +, disappeared within 1-15 minutes after delayed irritation, and the bitterness was acceptable.

Reference sample: Instantaneous irritation ++, disappear after more than 30 minutes after delayed irritation, and the bitterness was unacceptable.

Detailed Information is Listed in Table 41:

TABLE 41

Comparison test of taste of vortioxetine hemihydrobromide taste masking powder

| Subject | Instantaneous irritation | | Delayed irritation (min) | | Bitterness | | Grittiness | |
|---|---|---|---|---|---|---|---|---|
| | Self-made sample | Reference sample | Self-made sample | Reference sample | Self-made sample | Reference sample | Self-made sample | Reference sample |
| Subject 1 | + | ++ | 1-15 | 15-30 | acceptable | unacceptable | N/A | N/A |
| Subject 2 | + | ++ | 1-15 | 15-30 | acceptable | unacceptable | N/A | N/A |
| Subject 3 | + | +++ | 1-15 | >30 | acceptable | unacceptable | N/A | N/A |
| Subject 4 | + | ++ | 1-15 | >30 | acceptable | unacceptable | N/A | N/A |
| Subject 5 | + | +++ | 1-15 | 15-30 | acceptable | unacceptable | N/A | N/A |

Example 18: Preparation of 10 mg/Table Vortioxetine Hydrobromide Film-Coated Tables The formula of 100 tablets weighing 0.152 g each made from the Vortioxetine hydrobromide was as follows:

| | |
|---|---|
| Powder prepared from Example 9b | 2.25 g (equal to 1.0 g of Vortioxetine) |
| Microcrystalline cellulose | 4.15 g |
| Mannitol P 100 SD | 8.00 g |
| Sodium starch glycolate | 0.70 g |
| Magnesium stearate | 0.10 g |
| Stomach-soluble coating material | q.s. (0.456 g) |
| Total | 15.20 g |

Preparation Process:

(1) The prescription amount of powder prepared from Example 9b, microcrystalline cellulose, mannitol P100SD, sodium starch glycolate, and magnesium stearate were placed in a clean and dry 50 ml screw-top glass reagent bottle. After mixing in a vortex blender for five minutes, the mixture was taken out after passing through 80 mesh sieve. After mixing for another five minutes, the mixture was taken out after passing through 80 mesh sieve, and finally after mixing for another five minutes, the compressed premix was obtained;

(2) The compressed premix was pressed by using ZP8 rotary tablet press with a diameter of 8.0 mm mold, controlling the tablet weight of 147-157 mg/tablet and hardness 40-60N, and obtaining the tablet core;

(3) The stomach-soluble coating material was added to purified water to prepared a suspension with the solid content of about 10%, continued stirring, set aside;

(4) Using the coating liquid prepared in step (3), the tablet core was coated with a high-efficiency coating machine, and the actual weight gain of the tablet core is about 1%.

The commercially available product (10 mg/tablet) and the grounded powder of the finished product in this invention were tasted and compared by 10 subjects. The irritation of the commercially available product was obvious and could hardly be tolerated, while, the taste of the self-made product in this invention was acceptable.

Self-made sample: Instantaneous irritation +, disappeared within 1-15 minutes after delayed irritation, and the bitterness was acceptable.

Commercially available product: Instantaneous irritation ++, disappear after more than 30 minutes after delayed irritation, and the bitterness was unacceptable.

Detailed Information is Listed in Table 42:

TABLE 42

Comparison test of taste of vortioxetine hydrobromide film-coated tablet

| | Instantaneous irritation | | Delayed irritation (min) | | Bitterness | | Grittiness | |
|---|---|---|---|---|---|---|---|---|
| Subject | Self-made sample | Commercially available product | Self-made sample | Commercially available product | Self-made sample | Commercially available product | Self-made sample | Commercially available product |
| Subject 1 | + | +++ | 1-15 | >30 | acceptable | unacceptable | N/A | N/A |
| Subject 2 | + | +++ | 1-15 | >30 | acceptable | unacceptable | N/A | N/A |
| Subject 3 | + | +++ | 1-15 | >30 | acceptable | unacceptable | N/A | N/A |
| Subject 4 | ++ | +++ | 1-15 | >30 | acceptable | unacceptable | N/A | N/A |
| Subject 5 | + | +++ | 1-15 | >30 | acceptable | unacceptable | N/A | N/A |
| Subject 6 | + | +++ | 1-15 | >30 | acceptable | unacceptable | N/A | N/A |
| Subject 7 | + | +++ | 1-15 | >30 | acceptable | unacceptable | N/A | N/A |
| Subject 8 | ++ | +++ | 1-15 | >30 | acceptable | unacceptable | N/A | N/A |
| Subject 9 | + | +++ | 1-15 | >30 | acceptable | unacceptable | N/A | N/A |
| Subject 10 | + | +++ | 1-15 | >30 | acceptable | unacceptable | N/A | N/A |

The self-made finished product of this invention was tested for preliminary stability according to the requirements of the 2015 Edition of the Pharmacopoeia of the People's Republic of China Compared with the commercially available product, dissolution rate of the self-made finished product of this invention in 0.1N hydrochloric acid and pH 4.5 acetate buffer (paddle method, 50 r/min) was significantly faster, and the dissolution degree (30 minutes) is significantly better.

The results are shown in Table 43.

TABLE 43

Preliminary Stability Test Table of Vortioxetine Hydrobromide (Temperature: 50° C. ± 2° C., Humidity: 75% ± 5%)

| | | Test | | | | | | |
|---|---|---|---|---|---|---|---|---|
| | | Identification | | | Dissolution rate | Dissolution rate in pH 4.5 | | Max single |
| | | Free | | Content | in 0.1N HCl (%) | acetate buffer (%) | | impurity |
| Time | Source | base | Br | uniformity | 10 minutes | 10 minutes | 30 minutes | (%) |
| Initial | Commercially available | + | + | Pass | 81 | 68 | 78 | 0.12 |
| | Self-made | + | + | Pass | 94 | 93 | 98 | 0.10 |
| 5 days | Commercially available | + | + | Pass | 79 | 71 | 79 | 0.13 |
| | Self-made | + | + | Pass | 98 | 97 | 99 | 0.11 |
| 10 days | Commercially available | + | + | Pass | 84 | 65 | 81 | 0.14 |
| | Self-made | + | + | Pass | 95 | 97 | 99 | 0.12 |

Example 19: Preparation of 20 mg/Table Orally Disintegrating Tables (Compressed Tablet)

19a) the Formula of 100 Tablets Weighing 0.088 g Each Made from the Vortioxetine Hemihydrobromide was as Follows:

| | |
|---|---|
| Vortioxetine hemihydrobromide | 2.28 g (equal to 2 g of Vortioxetine) |
| Mannitol P100 SD | 5.14 g |
| Trisodium phosphate | 0.228 g |
| Crospovidone XL | 0.352 g |
| Croscarmellose Sodium | 0.352 g |
| Sodium starch glycolate | 0.352 g |
| Magnesium stearate | 0.044 g |
| Neotame | 0.010 g |

-continued

| | |
|---|---|
| Red Ferric Oxide | 0.044 g |
| Total | 8.802 g |

Preparation Process:

(1) Neotame and red iron oxide passed 200 mesh, and other raw materials passed 100 mesh sieve, set aside;-

(2) The prescription amount of vortioxetine hemihydrobromide, trisodium phosphate, mannitol P100SD, crospovidone XL, croscarmellose sodium, sodium starch glycolate, magnesium stearate, Neotame, and red iron oxide were placed in a clean and dry 50 ml screw-top glass reagent bottle. After mixing in a vortex blender for five minutes, the mixture was taken out after passing through 80 mesh sieve. After mixing for another five minutes, the mixture was taken out after passing through 80 mesh sieve, and finally after mixing for another five minutes, the compressed premix was obtained;

(3) The compressed premix was pressed by using ZP8 rotary tablet press with a diameter of 6.0 mm shallow concave mold, controlling the tablet weight of 86-90 mg/tablet and hardness 0.7-1.5 kG, and obtaining the tablet.

19b: The Formula of 100 Tablets Weighing 0.088 g Each Made from the Vortioxetine Hydrobromide was as Follows:

| | |
|---|---|
| Vortioxetine hydrobromide | 2.54 g (equal to 2 g of Vortioxetine) |
| Mannitol PlOOSD | 4.88 g |
| Trisodium phosphate | 0.228 g |
| Crospovidone XL | 0.352 g |
| Croscarmellose Sodium | 0.352 g |
| Sodium starch glycolate | 0.352 g |
| Magnesium stearate | 0.044 g |
| Neotame | 0.010 g |
| Red Ferric Oxide | 0.044 g |
| Total | 8.802g |

Preparation Process:

(1) Neotame and red iron oxide passed 200 mesh, and other raw materials passed 100 mesh sieve, set aside;

(2) The prescription amount of vortioxetine hydrobromide, trisodium phosphate, mannitol P100SD, crospovidone XL, croscarmellose sodium, sodium starch glycolate, magnesium stearate, Neotame, and red iron oxide were placed in a clean and dry 50 ml screw-top glass reagent bottle. After mixing in a vortex blender for five minutes, the mixture was taken out after passing through 80 mesh sieve. After mixing for another five minutes, the mixture was taken out after passing through 80 mesh sieve, and finally after mixing for another five minutes, the compressed premix was obtained;

(3) The compressed premix was pressed by using ZP8 rotary tablet press with a diameter of 6.0 mm shallow concave mold, controlling the tablet weight of 86-90 mg/tablet and hardness 0.7-1.5 kG, and obtaining the tablet.

After 10 subjects tried the taste, the two samples had no grittiness feeling; the sample made of vortioxetine hemihydrobromide hardly felt irritation, and the taste was better; while, the sample made of vortioxetine hydrobromide was significantly more irritating than the vortioxetine hemihydrobromide samples, and showed mild discomfort.

Self-made sample 19a: Instantaneous irritation +, disappeared within 1-15 minutes after delayed irritation, and the bitterness was acceptable.

Self-made sample 19b: Instantaneous irritation ++, disappear after more than 30 minutes after delayed irritation, and the bitterness was unacceptable.

Detailed Information is Listed in Table 44:

TABLE 44

Comparison test of taste of orally disintegrating tables

| Subject | Instantaneous irritation | | delayed irritation (min) | | bitterness | | Grittiness | |
|---|---|---|---|---|---|---|---|---|
| | vortioxetine hemihydro-bromide samples | vortioxetine hydrobromide samples | vortioxetine hemihydro-bromide samples | vortioxetine hydrobromide samples | vortioxetine hemihydro-bromide samples | vortioxetine hydrobromide samples | vortioxetine hemihydro-bromide samples | vortioxetine hydrobromide samples |
| Subject 1 | + | ++ | 1-15 | 15-30 | acceptable | acceptable | No | No |
| Subject 2 | ++ | +++ | 1-15 | >30 | acceptable | unacceptable | No | No |
| Subject 3 | + | + | 1-15 | 15-30 | acceptable | unacceptable | No | No |
| Subject 4 | ++ | +++ | 1-15 | >30 | acceptable | unacceptable | No | No |
| Subject 5 | + | ++ | 1-15 | 15-30 | acceptable | unacceptable | No | No |
| Subject 6 | ++ | +++ | 1-15 | 15-30 | acceptable | unacceptable | No | No |
| Subject 7 | + | ++ | 1-15 | 15-30 | acceptable | acceptable | No | No |
| Subject 8 | + | ++ | 1-15 | 15-30 | acceptable | unacceptable | No | No |
| Subject 9 | ++ | +++ | 1-15 | >30 | acceptable | unacceptable | No | No |
| Subject 10 | + | + | 1-15 | 1-15 | acceptable | acceptable | No | No |

Example 20: Preparation of 20 mg/Table Orally Disintegrating Tables (Compressed Tablet)

The Formula of 100 Tablets Weighing 0.152 g Each Made from the Vortioxetine Hemihydrobromide was as Follows:

| | |
|---|---|
| Powder prepared from Example 10 | 4.61 g (equal to 2.0 g of Vortioxetine) |
| Mannitol P 100 SD | 8.30 g |
| Trisodium phosphate | 0.304 g |
| Crospovidone XL | 0.608 g |
| Cro scarmello se Sodium | 0.608 g |
| Sodium starch glycolate | 0.608 g |
| Magnesium stearate | 0.076 g |
| Neotame | 0.015 g |
| Red Ferric Oxide | 0.076 g |
| Total | 15.205 g |

Preparation Process:

(1) Neotame and red iron oxide passed 200 mesh, and other raw materials passed 100 mesh sieve, set aside;

(2) The prescription amount of solid dispersion, trisodium phosphate, mannitol P100SD, crospovidone XL, croscarmellose sodium, sodium starch glycolate, magnesium stearate, Neotame, and red iron oxide were placed in a clean and dry 50 ml screw-top glass reagent bottle. After mixing in a vortex blender for five minutes, the mixture was taken out after passing through 80 mesh sieve. After mixing for another five minutes, the mixture was taken out after passing through 80 mesh sieve, and finally after mixing for another five minutes, the compressed premix was obtained;

(3) The compressed premix was pressed by using ZP8 rotary tablet press with a diameter of 8.0 mm shallow concave mold, controlling the tablet weight of 145-149 mg/tablet and hardness 15-30N, and obtaining the tablet.

The detection value of pH and relative exposure: 8.92, 0.19% (7.5 ug/ml).

After 10 subjects tried the taste, the sample dissolved in the oral cavity within 10 seconds, there was no feeling of grittiness, almost no irritation, and the taste was good.

Self-made sample: Instantaneous irritation +, disappeared within 1-15 minutes after delayed irritation, and the bitterness was acceptable.

Detailed Information is Listed in Table 45:

TABLE 45

Comparison test of taste of orally disintegrating tables

| Subject | Instantaneous irritation | Delayed irritation (min) | Bitterness | Grittiness |
|---|---|---|---|---|
| Subject 1 | + | 1-15 | acceptable | No |
| Subject 2 | + | 1-15 | acceptable | No |
| Subject 3 | + | 1-15 | acceptable | No |
| Subject 4 | + | 1-15 | acceptable | No |
| Subject 5 | + | 1-15 | acceptable | No |
| Subject 6 | + | 1-15 | acceptable | No |
| Subject 7 | + | 1-15 | acceptable | No |
| Subject 8 | + | 1-15 | acceptable | No |
| Subject 9 | + | 1-15 | acceptable | No |
| Subject 10 | ++ | 1-15 | acceptable | No |

Example 21: Preparation of 20 mg/Table Orally Disintegrating Tables (Lyophilized Tablets)

The Formula:

| | |
|---|---|
| Vortioxetine hemihydrobromide | 0.912 g |
| Mannitol | 1.876 g |
| Sorbitol | 2.000 g |
| PEG 4000 | 1.030 g |
| Trisodium phosphate | 0.248 g |
| Medicinal Type B Gelatin | 0.124 g |
| Neotame | 0.001 g |
| Red Ferric Oxide | 0.003 g |
| Total | 6.194 g |

Purified water was added to 16 g to make 40 tablets, each of which was about 0.4 g, and contained about 0.1548 g of solids.

Preparation Process:

(1) Vortioxetine hemihydrobromide and red iron oxide passed 100 mesh sieve, set aside;

(2) The prescription amount of mannitol, Sorbitol, PEG 4000, medicinal type B gelatin and Neotame were placed in a clean and dry 20 ml screw-top glass reagent bottle, then 8 g of purified water was added, tightened the cap. After shaking to dissolve at 50° C., the solution was cooled to room temperature, then the prescription amount of vortioxetine hemihydrobromide, red iron oxide, and anhydrous trisodium phosphate were added, shaking and dispersing, then purified water was added to prescription amount. After shaking and dispersing, mixture was passed through the 80-mesh stainless steel screen for 3 times, the suspension was obtained for separate loading, and the suspension was continuously stirred to prevent sedimentation;

(3) The suspension for dispensing was 0.4 g per hole into the mold hole, freeze-dried;

(4) The freeze-dried sample was heat-sealed to obtain freeze-dried orally disintegrating tablets.

The detection value of pH and relative exposure: 10.42, 0.27% (10.7 ug/ml).

After testing by 10 volunteer subjects, the sample disintegrated within 5 seconds in the oral cavity, with no grit feeling and minimal irritation.

Self-made sample: Instantaneous irritation +, disappeared within 1-15 minutes after delayed irritation, and the bitterness was acceptable.

Detailed Information is Listed in Table 46:

TABLE 46

Comparison test of taste of orally disintegrating tables

| Subject irritation | Instantaneous Delayed | irritation (min) | Bitterness | Grittiness |
|---|---|---|---|---|
| Subject 1 | + | 1-15 | acceptable | No |
| Subject 2 | + | 1-15 | acceptable | No |
| Subject 3 | ++ | 1-15 | acceptable | No |
| Subject 4 | + | 1-15 | acceptable | No |
| Subject 5 | + | 1-15 | acceptable | No |
| Subject 6 | + | 1-15 | acceptable | No |
| Subject 7 | + | 1-15 | acceptable | No |
| Subject 8 | ++ | 1-15 | acceptable | No |
| Subject 9 | + | 1-15 | acceptable | No |
| Subject 10 | ++ | 1-15 | acceptable | No |

Example 22: Preparation of 20 mg/Tablet Orally Disintegrating Tables (Compressed Tablets, Lyophilized Tablets)

22a: The Formula of 100 Tablets Weighing 0.152 g Each Made from the Vortioxetine Hemihydrobromide Micronized Powder Coated Powder was as Follows:

| | |
|---|---|
| Powder prepared from Example 3a | 4.79 g (equal to 2.0 g of Vortioxetine) |
| Mannitol P 100 SD | 8.15 g |
| Sodium bicarbonate | 0.304 g |
| Crospovidone XL | 0.608 g |
| Cro scarmello se Sodium | 0.608 g |
| Sodium starch glycolate | 0.608 g |
| Magnesium stearate | 0.076 g |
| Neotame | 0.015 g |
| Red Ferric Oxide | 0.076 g |
| Total | 15.205 g |

Preparation Process:

(1) Neotame and red iron oxide passed 200 mesh, and other raw materials passed 80 mesh sieve, set aside;

(2) The prescription amount of powder prepared from Example 3a, sodium bicarbonate, mannitol P100SD, crospovidone XL, croscarmellose sodium, sodium starch glycolate, magnesium stearate, Neotame, and red iron oxide were placed in a clean and dry 20 ml screw-top glass reagent bottle. After mixing in a vortex blender for five minutes, the mixture was taken out after passing through 80 mesh sieve. After mixing for another five minutes, the mixture was taken out after passing through 80 mesh sieve, and finally after mixing for another five minutes, the compressed premix was obtained;

(3) The compressed premix was pressed by using ZP8 rotary tablet press with a diameter of 8.0 mm shallow concave mold, controlling the tablet weight of 145-149 mg/tablet and hardness 15-30N, and obtaining the tablet.

22b: The Formula of Coated Powder of Vortioxetine Hemihydrobromide Micronized Powder Made into Freeze-Dried Orally Disintegrating Tablets was as Follows:

| | |
|---|---|
| Powder prepared from Example 3a | 1.914 g (equal to 0.8 g of Vortioxetine) |

-continued

| | |
|---|---|
| Mannitol | 2.000 g |
| Sorbitol | 2.000 g |
| PEG 4000 | 1.030 g |
| Sodium bicarbonate | 0.124 g |
| Medicinal Type B Gelatin | 0.124 g |
| Neotame | 0.001 g |
| Red Ferric Oxide | 0.003 g |
| Total | 7.196g |

Purified water was added to 16 g to make 40 tablets, each of which was about 0.4 g, and contained about 0.1799 g of solids.

Preparation Process:

(1) API passed 100 mesh sieve, set aside;

(2) The prescription amount of mannitol, Sorbitol, PEG 4000, medicinal type B gelatin and Neotame were placed in a clean and dry 20 ml screw-top glass reagent bottle, then about 8 g of purified water was added, tightened the cap. After shaking to dissolve at 50° C., the solution was cooled to room temperature, then the prescription amount of powder prepared from Example 3a, red iron oxide, and sodium bicarbonate were added, shaking and dispersing, then purified water was added to prescription amount. After shaking and dispersing, mixture was passed through the 80-mesh stainless steel screen for 3 times, the suspension was obtained for separate loading, and the suspension was continuously stirred to prevent sedimentation;

(3) The suspension for dispensing was 0.4 g per hole into the mold hole, freeze-dried;

(4) The freeze-dried sample was heat-sealed to obtain freeze-dried orally disintegrating tablets.

The Detection Value of pH and Relative Exposure:

Self-made sample 22a: pH 8.02, 0.21% (8.3 ug/ml);

Self-made sample 22b: pH 9.79, 0.25% (9.9 ug/ml).

After testing by 10 volunteer subjects, the sample 22a disintegrated in the oral cavity within 10 seconds, and the sample 22b disintegrated in the oral cavity within 5 seconds, and there was no grit feeling and minimal irritation both.

Self-made sample 22a: Instantaneous irritation +, disappeared within 1-15 minutes after delayed irritation, and the bitterness was acceptable.

Self-made sample 22b: Instantaneous irritation +, disappeared within 1-15 minutes after delayed irritation, and the bitterness was acceptable.

Detailed Information is Listed in Table 47:

TABLE 47

Comparison of taste of vortioxetine hemihydrobromide micro-powder coated orally disintegrating tablets

| | Instantaneous | | Delayed irritation (min) | | Bitterness | | Grittiness | |
|---|---|---|---|---|---|---|---|---|
| Subject | Sample 22a | Sample 22b | Sample 22a | Sample 22b | Sample 22a | Sample 22b | Sample 22a | Sample 22b |
| Subject 1 | + | + | 1-15 | 1-15 | acceptable | acceptable | No | No |
| Subject 2 | + | + | 1-15 | 1-15 | acceptable | acceptable | No | No |
| Subject 3 | + | + | 1-15 | 1-15 | acceptable | acceptable | No | No |
| Subject 4 | ++ | ++ | 1-15 | 1-15 | acceptable | acceptable | No | No |
| Subject 5 | + | + | 1-15 | 1-15 | acceptable | acceptable | No | No |
| Subject 6 | + | + | 1-15 | 1-15 | acceptable | acceptable | No | No |
| Subject 7 | + | + | 1-15 | 1-15 | acceptable | acceptable | No | No |
| Subject 8 | + | + | 1-15 | 15-30 | acceptable | unacceptable | No | No |
| Subject 9 | + | + | 1-15 | 15-30 | acceptable | unacceptable | No | No |
| Subject 10 | + | + | 1-15 | 1-15 | acceptable | acceptable | No | No |

Example 23: Preparation of 20 mg/Tablet Orally Disintegrating Tables (Compressed Tablets, Lyophilized Tablets)

23a: The Formula of 100 Tablets Weighing 0.152 g Each Made from the Vortioxetine Hemihydrobromide Micronized Powder Coated Powder was as Follows:

| | |
|---|---|
| Powder prepared from Example 7a | 5.60 g (equal to 2.0 g of Vortioxetine) |
| Mannitol P100 SD | 7.31 g |
| Tripotassium Phosphate Anhydrous | 0.304 g |
| Crospovidone XL | 0.608 g |
| Croscarmellose Sodium | 0.608 g |
| Sodium starch glycolate | 0.608 g |
| Magnesium stearate | 0.076 g |
| Neotame | 0.015 g |
| Red Ferric Oxide | 0.076 g |
| Total | 15.205 g |

Preparation Process:

(1) Neotame and red iron oxide passed 200 mesh, and other raw materials passed 80 mesh sieve, set aside;

(2) The prescription amount of powder prepared from Example 7a, tripotassium phosphate anhydrous, mannitol P100SD, crospovidone XL, croscarmellose sodium, sodium starch glycolate, magnesium stearate, Neotame, and red iron oxide were placed in a clean and dry 50 ml screw-top glass reagent bottle. After mixing in a vortex blender for five minutes, the mixture was taken out after passing through 80 mesh sieve. After mixing for another five minutes, the mixture was taken out after passing through 80 mesh sieve, and finally after mixing for another five minutes, the compressed premix was obtained;

(3) The compressed premix was pressed by using ZP8 rotary tablet press with a diameter of 8.0 mm shallow concave mold, controlling the tablet weight of 145-149 mg/tablet and hardness 15-30N, and obtaining the tablet.

23b: The Formula of Coated Powder of Vortioxetine Hemihydrobromide Micronized Powder Made into Freeze-Dried Orally Disintegrating Tablets was as Follows:

| | |
|---|---|
| Powder prepared from Example 7a | 2.240 g (equal to 0.8 g of Vortioxetine) |

-continued

| | |
|---|---|
| Mannitol | 2.000 g |
| Sorbitol | 2.000 g |
| PEG 4000 | 1.030 g |
| Tripotassium Phosphate Anhydrous | 0.124 g |
| Medicinal Type B Gelatin | 0.124 g |
| Neotame | 0.001 g |
| Red Ferric Oxide | 0.003 g |
| Total | 7.522 g |

Purified water was added to 16 g to make 40 tablets, each of which was about 0.4 g, and contained about 0.1881 g of solids.

Preparation Process:

(1) API passed 100 mesh sieve, set aside;

(2) The prescription amount of mannitol, Sorbitol, PEG 4000, medicinal type B gelatin and Neotame were placed in a clean and dry 20 ml screw-top glass reagent bottle, then about 8 g of purified water was added, tightened the cap. After shaking to dissolve at 50° C., the solution was cooled to room temperature, then the prescription amount of powder prepared from Example 7a, red iron oxide, and tripotassium Phosphate Anhydrous were added, shaking and dispersing, then purified water was added to prescription amount. After shaking and dispersing, mixture was passed through the 100-mesh stainless steel screen for 3 times, the suspension was obtained for separate loading, and the suspension was continuously stirred to prevent sedimentation;

(3) The suspension for dispensing was 0.4 g per hole into the mold hole, freeze-dried;

(4) The freeze-dried sample was heat-sealed to obtain freeze-dried orally disintegrating tablets.

The Detection Value of pH and Relative Exposure:

Self-made sample 23a: pH 8.02, 0.21% (8.3 ug/ml);

Self-made sample 23b: pH 9.79, 0.25% (9.9 ug/ml).

After testing by 10 volunteer subjects, the sample 23a disintegrated in the oral cavity within 10 seconds, and the sample 23b disintegrated in the oral cavity within 5 seconds, and there was no grit feeling and minimal irritation both.

Self-made sample 23a: Instantaneous irritation +, disappeared within 1-15 minutes after delayed irritation, and the bitterness was acceptable.

Self-made sample 23b: Instantaneous irritation +, disappeared within 1-15 minutes after delayed irritation, and the bitterness was acceptable.

Detailed Information is Listed in Table 48:

TABLE 48

Comparison of taste of vortioxetine hemihydrobromide solid dispersion orally disintegrating tablets

| | Instantaneous | | Delayed irritation (min) | | Bitterness | | Grittiness | |
|---|---|---|---|---|---|---|---|---|
| Subject | Sample 23a | Sample 23b | Sample 23a | Sample 23b | Sample 23a | Sample 23b | Sample 23a | Sample 23b |
| Subject 1 | + | + | 1-15 | 1-15 | acceptable | acceptable | No | No |
| Subject 2 | + | + | 1-15 | 1-15 | acceptable | acceptable | No | No |
| Subject 3 | + | + | 1-15 | 1-15 | acceptable | acceptable | No | No |
| Subject 4 | + | ++ | 1-15 | 1-15 | acceptable | acceptable | No | No |
| Subject 5 | ++ | + | 1-15 | 1-15 | acceptable | acceptable | No | No |
| Subject 6 | + | + | 1-15 | 1-15 | acceptable | acceptable | No | No |
| Subject 7 | + | + | 1-15 | 1-15 | acceptable | acceptable | No | No |
| Subject 8 | + | + | 1-15 | 1-15 | acceptable | acceptable | No | No |
| Subject 9 | + | + | 1-15 | 1-15 | acceptable | acceptable | No | No |
| Subject 10 | + | + | 1-15 | 1-15 | acceptable | acceptable | No | No |

Example 24: Preparation of 20 mg/Tablet Orally Disintegrating Tables (Compressed Tablets, Lyophilized Tablets)

24a: The Formula of 100 Tablets Weighing 0.152 g Each Made from the Vortioxetine Hemihydrobromide Micronized Powder Coated Powder was as Follows:

| | |
|---|---|
| Powder prepared from Example 11a | 5.80 g (equal to 2.0 g of Vortioxetine) |
| Mannitol P100 SD | 7.140 g |
| Disodium hydrogen phosphate anhydrous | 0.304 g |
| Crospovidone XL | 0.608 g |
| Croscarmellose Sodium | 0.608 g |
| Sodium starch glycolate | 0.608 g |
| Magnesium stearate | 0.076 g |
| Neotame | 0.015 g |
| Red Ferric Oxide | 0.076 g |
| Total | 15.235 g |

Preparation Process:

(1) Neotame and red iron oxide passed 200 mesh, and other raw materials passed 80 mesh sieve, set aside;

(2) The prescription amount of powder prepared from Example 11a, disodium hydrogen phosphate anhydrous, mannitol P100SD, crospovidone XL, croscarmellose sodium, sodium starch glycolate, magnesium stearate, Neotame, and red iron oxide were placed in a clean and dry 50 ml screw-top glass reagent bottle. After mixing in a vortex blender for five minutes, the mixture was taken out after passing through 80 mesh sieve. After mixing for another five minutes, the mixture was taken out after passing through 80 mesh sieve, and finally after mixing for another five minutes, the compressed premix was obtained;

(3) The compressed premix was pressed by using ZP8 rotary tablet press with a diameter of 8.0 mm shallow concave mold, controlling the tablet weight of 147-157 mg/tablet and hardness 15-30N, and obtaining the tablet.

24b: The Formula of Coated Powder of Vortioxetine Hemi-hydrobromide Micronized Powder Made into Freeze-Dried Orally Disintegrating Tablets was as Follows:

| | |
|---|---|
| Powder prepared from Example 11a | 2.321 g (equal to 0.8 g of Vortioxetine) |
| Mannitol | 2.000 g |
| Sorbitol | 2.000 g |
| PEG 4000 | 1.030 g |
| Disodium hydrogen phosphate anhydrous | 0.124 g |
| Medicinal Type B Gelatin | 0.124 g |
| Neotame | 0.001 g |
| Red Ferric Oxide | 0.003 g |
| Total | 7.603 g |

Purified water was added to 16 g to make 40 tablets, each of which was about 0.4 g, and contained about 0.1901 g of solids.

Preparation Process:

(1) Red iron oxide passed 200 mesh, set aside;

(2) The prescription amount of mannitol, Sorbitol, PEG 4000, medicinal type B gelatin and Neotame were placed in a clean and dry 20 ml screw-top glass reagent bottle, then about 8 g of purified water was added, tightened the cap. After shaking to dissolve at 50° C., the solution was cooled to room temperature, then the prescription amount of powder prepared from Example 11a, red iron oxide, and disodium hydrogen phosphate anhydrous were added, shaking and dispersing, then purified water was added to prescription amount. After shaking and dispersing, mixture was passed through the 100-mesh stainless steel screen for 3 times, the suspension was obtained for separate loading, and the suspension was continuously stirred to prevent sedimentation;

(3) The suspension for dispensing was 0.4 g per hole into the mold hole, freeze-dried;

(4) The freeze-dried sample was heat-sealed to obtain a freeze-dried orally disintegrating tablets.

The Detection Value of pH and Relative Exposure:

Self-made sample 24a: pH 7.98, 0.29% (11.5 ug/ml);

Self-made sample 24b: pH 9.79, 0.35% (13.9 ug/ml).

After testing by 10 volunteer subjects, the sample 24a disintegrated in the oral cavity within 10 seconds, and the sample 24b disintegrated in the oral cavity within 5 seconds, and there was no grit feeling and minimal irritation both.

Self-made sample 24a: Instantaneous irritation +, disappeared within 1-15 minutes after delayed irritation, and the bitterness was acceptable.

Self-made sample 24b: Instantaneous irritation +, disappeared within 1-15 minutes after delayed irritation, and the bitterness was acceptable.

Detailed Information is Listed in Table 49:

TABLE 49

Comparison of taste of vortioxetine hemihydrobromide solid dispersion orally disintegrating tablets

| | Instantaneous | | Delayed irritation (min) | | Bitterness | | Grittiness | |
|---|---|---|---|---|---|---|---|---|
| Subject | Sample 24a | Sample 24b | Sample 24a | Sample 24b | Sample 24a | Sample 24b | Sample 24a | Sample 24b |
| Subject 1 | + | + | 1-15 | 1-15 | acceptable | acceptable | No | No |
| Subject 2 | + | + | 1-15 | 1-15 | acceptable | acceptable | No | No |
| Subject 3 | + | + | 1-15 | 1-15 | acceptable | acceptable | No | No |
| Subject 4 | + | + | 1-15 | 1-15 | acceptable | acceptable | No | No |
| Subject 5 | + | + | 1-15 | 1-15 | acceptable | acceptable | No | No |
| Subject 6 | + | + | 1-15 | 1-15 | acceptable | acceptable | No | No |
| Subject 7 | + | + | 1-15 | 1-15 | acceptable | acceptable | No | No |
| Subject 8 | + | + | 1-15 | 1-15 | acceptable | acceptable | No | No |
| Subject 9 | + | ++ | 1-15 | 1-15 | acceptable | acceptable | No | No |
| Subject 10 | + | + | 1-15 | 1-15 | acceptable | acceptable | No | No |

Example 25: Preparation of 20 mg/Tablet Dispersible Tablets

The Formula of 100 Tablets Each Weighing 0.152 Grams was as Follows:

| | |
|---|---|
| Powder prepared from Example 10 | 4.61 g (equal to 2.0 g of Vortioxetine) |
| Microcrystalline cellulose | 2.68 g |
| Mannitol P100SD | 7.35 g |
| Calcium hydroxide | 0.02 g |
| Sodium starch glycolate | 0.60 g |
| Neotame | 0.001 g |
| Magnesium stearate | 0.05 g |
| Total | 15.17 g |

Preparation Process:

(1) The prescription amount of powder prepared from Example 10, microcrystalline cellulose, mannitol P100SD, calcium hydroxide, sodium starch glycolate, Neotame and magnesium stearate were placed in a clean and dry 50 ml screw-top glass reagent bottle. After mixing in a vortex blender for five minutes, the mixture was taken out after passing through 80 mesh sieve. After mixing for another five minutes, the mixture was taken out after passing through 80 mesh sieve, and finally after mixing for another five minutes, the compressed premix was obtained;

(2) The compressed premix was pressed by using ZP8 rotary tablet press with a diameter of 8.0 mm shallow concave mold, controlling the tablet weight of 147-157 mg/tablet and hardness 50-80N, and obtaining the tablet.

The detection value of pH and relative exposure: pH 8.79, 0.45% (17.9 ug/ml).

After the sample was ground into powder, the powder equivalent to 20 mg of vortioxetine was tested by 10 subjects. The taste of the finished product was acceptable with mild irritation within 1 minute.

Self-made sample: Instantaneous irritation +, disappeared within 1-15 minutes after delayed irritation, and the bitterness was acceptable.

Detailed Information is Listed in Table 50:

TABLE 50

Comparison test of taste of vortioxetine hemihydrobromide solid dispersion dispersible tables

| Subject | Instantaneous irritation | Delayed irritation (min) | Bitterness | Grittiness |
|---|---|---|---|---|
| Subject 1 | + | 1-15 | acceptable | No |
| Subject 2 | + | 1-15 | acceptable | No |
| Subject 3 | + | 1-15 | acceptable | No |
| Subject 4 | ++ | 1-15 | acceptable | No |
| Subject 5 | + | 1-15 | acceptable | No |
| Subject 6 | + | 1-15 | acceptable | No |
| Subject 7 | ++ | 1-15 | acceptable | No |
| Subject 8 | + | 1-15 | acceptable | No |
| Subject 9 | + | 1-15 | acceptable | No |
| Subject 10 | + | 1-15 | acceptable | No |

Example 26: Preparation of 20 mg/Tablet Dispersible Tablets

The Formula of 100 Tablets Each Weighing 0.152 g was as Follows:

| | |
|---|---|
| Powder prepared from Example 17 | 5.69 g (equal to 2.0 g of Vortioxetine) |
| Microcrystalline cellulose | 5.35 g |
| Mannitol P100SD | 3.50 g |
| Sodium starch glycolate | 0.60 g |
| Neotame | 0.01 g |
| Magnesium stearate | 0.05 g |
| Total | 15.20 g |

Preparation Process:

(1) The prescription amount of powder prepared from Example 17, microcrystalline cellulose, mannitol P100SD, sodium starch glycolate, Neotame and magnesium stearate were placed in a clean and dry 50 ml screw-top glass reagent bottle. After mixing in a vortex blender for five minutes, the mixture was taken out after passing through 80 mesh sieve. After mixing for another five minutes, the mixture was taken out after passing through 80 mesh sieve, and finally after mixing for another five minutes, the compressed premix was obtained;

(2) The compressed premix was pressed by using ZP8 rotary tablet press with a diameter of 8.0 mm shallow concave mold, controlling the tablet weight of 147-157 mg/tablet and hardness 50-80N, and obtaining the tablet.

The detection value of pH and relative exposure: 8.79, 0.45% (17.9 ug/ml).

After the sample was ground into powder, the powder equivalent to 20 mg of vortioxetine was tested by 10 subjects. The taste of the finished product was acceptable with mild irritation within 1 minute.

Self-made sample: Instantaneous irritation +, disappeared within 1-15 minutes after delayed irritation, and the bitterness was acceptable.

Detailed Information is Listed in Table 51:

TABLE 51

Comparison test of taste of vortioxetine hemihydrobromide solid dispersion dispersible tables

| Subject | Instantaneous irritation | Delayed irritation (min) | Bitterness | Grittiness |
|---|---|---|---|---|
| Subject 1 | + | 1-15 | acceptable | No |
| Subject 2 | + | 1-15 | acceptable | No |
| Subject 3 | + | 1-15 | acceptable | No |
| Subject 4 | + | 1-15 | acceptable | No |
| Subject 5 | + | 1-15 | acceptable | No |
| Subject 6 | + | 1-15 | acceptable | No |
| Subject 7 | + | 1-15 | acceptable | No |
| Subject 8 | + | 1-15 | acceptable | No |
| Subject 9 | + | 1-15 | acceptable | No |
| Subject 10 | + | 1-15 | acceptable | No |

Example 27: Preparation of Granules or Dry Suspension (5 g Per Bag, Containing 20 mg of Vortioxetine)

The Formula of 100 Bags Each Weighing 5 g was as Follows:

| | |
|---|---|
| Vortioxetine hemihydrobromide | 2.38 g (equal to 2.0 g of Vortioxetine) |
| Xylitol | 180 g |
| Mannitol P100SD | 180 g |
| Microcrystalline cellulose | 104 g |
| Colloidal silicon dioxide | 5 g |
| Carboxymethylcellulose sodium | 5 g |
| Tripotassium citrate | 2.5 g |
| Sodium starch glycolate | 20 g |
| Neotame | 0.5 g |
| Magnesium stearate | 1 g |
| Total | 500.28 g |

Preparation Process:

(1) API and excipients passed 100 mesh sieve, set aside;

(2) The prescription amount of vortioxetine hemihydrobromide, Xylitol, mannitol P100SD, microcrystalline cellulose, colloidal silicon dioxide, carboxymethylcellulose sodium, tripotassium citrate, sodium starch glycolate, Neotame and magnesium stearate were placed in a clean and dry 2 L stainless steel hopper. Installed the hopper on the hopper mixing machine, mixed them at 10 rpm for 10 minutes and took them out. After granulating with a rotary granulator and 0.5 mm stainless steel round hole mesh plate, continued to mix with a hopper mixer for 10 minutes at 10 rpm to obtain the premix for granulation;

(3) The premix for granulation was pressed into thin slices with a dry granulator, then granulated by using a 1.5 mm stainless steel round mesh plate. After sieving with a 40-mesh stainless steel screen, the fine powder was returned for re-granulating. 461.34 grams of granules were obtained, and the yield was 92.2%.

(4) The prepared particles were packed into aluminum-plastic heat-sealed bags at 5 g/bag, and then heat-sealed.

A bag of samples was dispersed in 20 ml of purified water. After 10 subjects tried the taste, the finished product tasted acceptable.

Self-made sample: Instantaneous irritation +, disappeared within 1-15 minutes after delayed irritation, and the bitterness was acceptable.

Detailed Information is Listed in Table 52:

TABLE 52

Taste test of vortioxetine hemihydrobromide granules

| Subject | Instantaneous irritation | Delayed irritation (min) | Bitterness | Grittiness |
|---|---|---|---|---|
| Subject 1 | + | 1-15 | acceptable | No |
| Subject 2 | + | 1-15 | acceptable | No |
| Subject 3 | + | 1-15 | acceptable | No |
| Subject 4 | ++ | 1-15 | acceptable | No |
| Subject 5 | + | 1-15 | acceptable | No |
| Subject 6 | + | 1-15 | acceptable | No |
| Subject 7 | + | 1-15 | acceptable | No |
| Subject 8 | + | 1-15 | acceptable | No |
| Subject 9 | + | 1-15 | acceptable | No |
| Subject 10 | + | 1-15 | acceptable | No |

Example 28: Preparation of Oral Suspension (5 ml Per Bottle, Containing 20 mg of Vortioxetine)

The Formula of Vortioxetine Hemihydrobromide Solid Dispersion Made into 5 ml:20 mg Oral Suspension was as Follows:

| | |
|---|---|
| Solid dispersion prepared from Example 13a | 13.63 g (equal to 2.0 g of Vortioxetine) |
| Xylitol | 50 g |
| Carboxymethylcellulose sodium | 0.5 g |
| Sodium acetate | 0.5 g |

Purified water was added to 50 ml,

Preparation Process:

(1) The prescription amount of solid dispersion prepared from Example 13a, xylitol, carboxymethylcellulose sodium and sodium acetate were added to 400 ml of purified water. The mixture was homogenized at 12,000 rpm for 2 minutes, and continued to stir for later use;

(2) After the suspension obtained in the above step was passed through a 100 mesh stainless steel sieve, the pH value was adjusted to 8.0-8.5 with 1N HCl or 1N NaOH solution, and the purified water was added to the prescription amount and stirred for use;

(3) The suspension was divided into a vial of 5 ml per bottle, stoppered and capped it.

Detailed Information is Listed in Table 53:

TABLE 53

Taste test of oral suspension of vortioxetine hemihydrobromide solid dispersion

| Subject | Instantaneous irritation | Delayed irritation (min) | Bitterness | Grittiness |
|---|---|---|---|---|
| Subject 1 | + | 1-15 | acceptable | No |
| Subject 2 | + | 1-15 | acceptable | No |
| Subject 3 | + | 1-15 | acceptable | No |
| Subject 4 | + | 1-15 | acceptable | No |
| Subject 5 | + | 1-15 | acceptable | No |
| Subject 6 | + | 1-15 | acceptable | No |
| Subject 7 | + | 1-15 | acceptable | No |
| Subject 8 | + | 1-15 | acceptable | No |
| Subject 9 | + | 1-15 | acceptable | No |
| Subject 10 | + | 1-15 | acceptable | No |

Comparative Example 1: Comparison of Taste of Different Salts

The vortioxetine lactate salt, vortioxetine hydrobromide and vortioxetine hemihydrobromide equivalent to 5 mg of vortioxetine respectively over 100 mesh powders were put directly in front of the upper part of the tongue for one minute. There were 10 subjects in each salt-type group, and each subject randomly tried each salt-type 3 times. After trying one salt-type taste, rinsed your mouth, and try another salt-type after there was no irritation. After trying the taste, record the bitterness level and tongue irritation, spit it out a few seconds later, rinse your mouth, record the time for the irritation to subside, eat 1-1.5 hours later, and record the irritation again. The following table 54 showed the comparison of the salt-type taste of different vortioxetine in 30 attempts by 10 subjects.

TABLE 54

Comparison of taste of different vortioxetine salt type by 10 subjects for 30 attempts (unit: times)

| | Number of subjects who felt different levels of bitterness | | | Number of subjects experiencing different irritation | | |
|---|---|---|---|---|---|---|
| Salt type | Extremely bitter | Slightly bitter | Not bitter | unbearable | Slightly irritating, tolerable | Basically no irritation |
| lactate salt | 29 | 1 | 0 | 27[(1)] | 3[(2)] | 0 |
| Monosalt hydrobromate | 28 | 2 | 0 | 28[(1)] | 2[(2)] | 0 |
| hemihydrobromide | 12 | 18 | 0 | 12[(1)] | 17[(2)] | 1 |

Note:
[(1)]Because the irritation was so strong that it was almost unbearable, and it couldn't subside even after mouthwashes for many times. The subside time was more than 1 hour, and the irritation could not be subsided after eating.
[(2)]There was no irritation after gargling.

Comparative Example 2: Comparison of Taste of Solid Dispersions in this Invention and Commercially Available Drug Product The solid dispersion equivalent to 10 mg vortioxetine prepared in Example 9b, vortioxetine hemihydrobromide powder equivalent to 10 mg vortioxetine, and the powder compressed by vortioxetine hydrobromide marketed drug product equivalent to 10 mg of vortioxetine hydrobromide passed through 100 mesh sieve, then they were put directly in front of the upper part of the tongue for one minute. There were 20 subjects in each powder group. After trying one powder taste, rinsed your mouth, and try another powder after there was no irritation. After trying the taste, record the bitterness level and tongue irritation, spit it out a few seconds later, rinse your mouth, record the time for the irritation to subside, eat 1-1.5 hours later, and record the irritation again. The following table 55 showed the comparison of taste of the different vortioxetine powder by 20 subjects.

TABLE 55

Comparison of taste of different vortioxetine powder by 20 subjects

| | Number of subjects who felt different levels of bitterness | | | Number of subjects experiencing different irritation | | |
|---|---|---|---|---|---|---|
| Powder | Extremely bitter | Slightly bitter | Not bitter | unbearable | Slightly irritating, tolerable | Basically no irritation |
| Vortioxetine hemihydrobromide powder | 9 | 11 | 0 | 2(1) | 12(2) | 6 |
| Solid dispersion prepared from Example 9b | 2 | 18 | 0 | 1(1) | 6(2) | 13 |
| Pressed powder from marketed drug product | 20 | 0 | 0 | 20(1) | 0 | 0 |

Note:

(1)Because the irritation was so strong that it was almost unbearable, and it couldn't subside even after mouthwashes for many times. The subside time was more than 2 hours, and the irritation could not be subsided after eating.

(2)There was no irritation after gargling.

The invention claimed is:

1. An orally dispersible taste masking composition, comprising vortioxetine hemihydrobromide and one or more pharmaceutically acceptable taste masking excipients at a weight ratio of 1:0.1-1:5, wherein the one or more taste masking excipients comprise one or more alkaline excipients selected from the group consisting of trisodium phosphate, disodium hydrogen phosphate, dipotassium hydrogen phosphate, potassium carbonate, sodium carbonate, sodium bicarbonate, potassium citrate, sodium acetate, calcium hydroxide, and meglumine, and wherein the vortioxetine hemihydrobromide and the one or more alkaline excipients are at a weight ratio of 1:0.01-1:0.3.

2. The orally dispersible taste masking composition according to claim 1, further comprising granules in which the vortioxetine hemihydrobromide is coated and/or imbedded with the one or more taste masking excipients.

3. The orally dispersible taste masking composition according to claim 1, further comprising a solid dispersion in which the vortioxetine hemihydrobromide is dispersed in the one or more taste masking excipients.

4. The orally dispersible taste masking composition according to claim 2, further comprising a solid dispersion in which the granules are dispersed in the one or more taste masking excipients.

5. The orally dispersible taste masking composition according to claim 3, further comprising granules in which the solid dispersion is coated and/or imbedded with the one or more taste masking excipients.

6. The orally dispersible taste masking composition according to claim 1, wherein the orally dispersible taste masking composition has a crystalline form, and wherein the crystalline form has characteristic peaks at 4.2±0.2° and 17.4±0.2° when Cu-Kα radiation is used and the X-ray powder diffraction pattern is expressed at 2θ angles.

7. The orally dispersible taste masking composition according to claim 1, further comprising a filler, a flavoring agent, a release regulator agent, a plasticizer, an anticaking agent, and/or a disintegrant agent.

8. The orally dispersible taste masking composition according to claim 3, wherein the one or more pharmaceutically acceptable taste masking excipients further comprise polyacrylic resin IV, wherein the orally dispersible taste masking composition has a crystalline form, and wherein the crystalline form has characteristic peaks at 4.2±0.2°, 14.5±0.2°, 17.4±0.2°, and 22.6±0.2° when Cu-Kα radiation is used and the X-ray powder diffraction pattern is expressed at 2θ angles.

9. A method for treating a depression disorder in a subject, comprising administering to the subject an effective amount of the orally dispersible taste masking composition according to claim 1.

10. The orally dispersible taste masking composition according to claim 1, wherein the one or more pharmaceutically acceptable taste masking excipients further comprise one or more selected from the group consisting of cellulose acetate, ethyl cellulose, hydroxypropyl cellulose, methacrylic acid copolymer, chitosan, copovidone, and polyvinyl alcohol.

* * * * *